(12) United States Patent
Saha et al.

(10) Patent No.: US 8,541,240 B2
(45) Date of Patent: Sep. 24, 2013

(54) COLORIMETRIC AND FLUORIMETRIC FLUORIDE SENSING

(75) Inventors: Sourav Saha, Tallahassee, FL (US); Samit Guha, Tallahassee, FL (US)

(73) Assignee: Florida State University Research Foundation, Inc., Tallahassee, FL (US)

(*) Notice: Subject to any disclaimer, the term of this patent is extended or adjusted under 35 U.S.C. 154(b) by 133 days.

(21) Appl. No.: 13/149,398

(22) Filed: May 31, 2011

(65) Prior Publication Data

US 2011/0294229 A1 Dec. 1, 2011

Related U.S. Application Data

(60) Provisional application No. 61/349,280, filed on May 28, 2010.

(51) Int. Cl.
*G01N 33/00* (2006.01)
*G01N 21/77* (2006.01)
*G01N 21/78* (2006.01)
*C07D 471/06* (2006.01)

(52) U.S. Cl.
USPC ........... 436/124; 436/164; 436/166; 436/172; 436/96; 436/501; 546/66

(58) Field of Classification Search
USPC ................. 436/124, 125, 164, 166, 172, 173, 436/91, 93, 96, 501; 546/66
See application file for complete search history.

(56) References Cited

U.S. PATENT DOCUMENTS

| | | | |
|---|---|---|---|
| 6,482,949 B1 | 11/2002 | Sessler et al. | |
| 7,622,075 B2 | 11/2009 | Meyerhoff et al. | |
| 7,718,804 B2 | 5/2010 | Geddes et al. | |
| 2004/0018631 A1 | 1/2004 | Ward et al. | |
| 2010/0285602 A1 | 11/2010 | Aldridge | |

FOREIGN PATENT DOCUMENTS

| | | |
|---|---|---|
| WO | 2004104578 A1 | 12/2004 |
| WO | 2009066115 A1 | 5/2009 |

OTHER PUBLICATIONS

Sakai et al. Chemical Communications, vol. 46, May 14, 2010, pp. 4225-4237.*
Alabugin, I.V., et al., "Electronic Basis of Improper Hydrogen Bonding: A Subtle Balance of Hyperconjugation and Rehybridization," 2003, JACS, 125/19:5973-5987.
Alkorta, I., et al., "Interaction of Anions with Perfluoro Aromatic Compounds," 2002, JAMCS, 124:8593-8598.
Andric, G., et al., "Spectrometry of Naphthalene Diimides and Their Anion Radicals," 2004, Aust J Chem, 57:1011-1019.
Arranz, P., et al., "Binding and Removal of Sulfate, Phosphate, Arsentate, Tetrachloromercurate, and Chromate in Aqueous Solution by Means of an Activated Carbon Functionalized with a Pyrimidine-Based Anion Receptor (HL). Crystal Structures of H3L(HgCl4)-H2O and [H3L(HgBr4)] H2O Showing Anion-Pi Interactions," 2010, Inorg Chem, 49:9321-9332.
Ayoob, S., et al., "Fluoride in Drinking Water: A Review on the Status and Stress Effects," 2006, Crit Rvws Environ Sci Tech, 36:433-487.
Bassin, E.B., et al., "Age-Specific Fluoride Exposure in Drinking Water and Osteosarcoma (United States)," 2006, Cancer Causes Control, 17:421-428.
Beer, P.D., et al., "Anion Recognition and Sensing: The State of the Art and Future Perspectives," 2001, Angew Chem Int Ed, 40:486-516.
Berryman, O.B., et al., "Experimental Evidence for Interactions Between Anions and Electron-Deficient Aromatic Rings," 2009, Chem Commun, 3143-3153.
Bhosale, S.V., et al., "A Core-Substituted Naphthalene Diimide Fluoride Sensor," Org. Lett,. 2009, 11/23:5418-5421.
Bhosale, S.V., et al., "Chemistry of Naphthalene Diimides," Chem. Soc. Rev., 2008, 37:331-342.
Black, R.M., et al., "The Interaction of Sarin and Soman with Plasma Proteins: The Identification of a Novel Phosphonylation site," 1999, Arch Toxicol, 73:123-126.
Caltagirone, C., et al., "Anion Receptor Chemistry: Highlights from 2007," 2009, Chem Soc Rev, 38:520-563.
Caltagirone, C., et al., "Anion Binding vs. Sulfonamide Deprotonation in Functionalised Ureas," 2008, Chem Commun, 61-63.
Cametti, M., et al., "Recognition and Sensing of Fluoride Anion," 2009, Chem Commun, 2809-2829.
Chifotides, H.T., et al., "The Pi-Accepting Arene HAT(CN)6 as a Halide Receptor Through Charge Transfer: Multisite Anion Interactions and Self-Assemply in Solution and the Solid State," 2010, Angew Chem Int Ed, 49:7202-7207.
Dawson, R.E., et al., "Experimental Evidence for the Functional Relevance of Anion-Pi Interactions," 2010, Nat Chem, 2:533-538.
Gale, P.A., "Synthetic Indole, Carbazole, Biindole and Indolocarbazole-Based Receptors: Applications in Anion Complexation and Sensing," 2008, Chem Commun, 4525-4540.
Gorteau, V., et al., "Rigid-Rod Anion—Pi Slides for Multiion Hopping Across Lipid Bilayers," 2007, Org Biomol Chem, 5:3000-3012.
Gorteau, V., et al., "Rigid Oligonaphthalenediimide Rods as Transmembrane Anion-Pi Slides," 2006, J Am Chem Soc, 128:14788-14789.
Guha, S., et al., "Fluoride Ion Sensing by an Anion-π Interaction," 2010, JACS, 132:17674-17677.
Hamuro, Y., et al., "Novel Folding Patterns in a Family of Oligoanthranilamedes: Non-Peptide Oligomers That Form Extended Helical Secondary Structures," 1997, JACS, 119:10587-10593.
Hay, B.P., et al., "Anion-Arene Adducts: C—H Hydrogen Bonding, Anion-Pi Interaction, and Carbon Bonding Motifs," 2008, Chem Commun, 2417-2428.

(Continued)

*Primary Examiner* — Maureen Wallenhorst
(74) *Attorney, Agent, or Firm* — Senniger Powers LLP

(57) ABSTRACT

The present invention generally relates to fluoride receptor reagent compounds that are derived from one or more N-aryl or heteroaryl substituted 1,4,5,8-naphthalenetetracarboxydiimide (NDI) units. The invention also relates to associated methods for the detection of fluoride in a composition. π-electron orbitals present in the NDI unit of the reagents form a complex with fluoride anions. It is believed that the anion-π interaction results in a charge transfer process between the fluoride anion and the NDI unit, resulting in a number of measurable effects (e.g., colorimetric response).

13 Claims, 27 Drawing Sheets

(56) References Cited

OTHER PUBLICATIONS

Hay, B.P., et al., "Structural Design Criteria for Anion Hosts: Strategies for Achieving Anion Shape Recognition through the Complementary Placement of Urea Donor Groups," 2005, JACS, 127:1810-1819.
Jiang, X., et al., "Reactivity-Based Fluoride Detection: Evolving Design Principles for Spring-Loaded Turn-On Fluorescent Probes," 2007, Organic Letters, 9/18:3579-3582.
Kang, S.O., et al., "New Polyamide Cryptand for Anion Binding," 2003, JACS, 125:10152-10153.
Katz, H.E., et al., "A Soluble and Air-Stable Organic Semiconductor with High Electron Mobility," 2000, Nature, 404:478-481.
Kauffman, J.M., "Water Fluoridation: A Review of Recent Research and Actions," 2005, JAPS, 10/2:38-44.
Lokey, R.S., et al., "Synthetic Molecules that Fold Into a Pleated Secondary Structure in Solution," 1995, Nature, 375:303-305.
Mareda, J., et al., "Anion-Pi Slides for Transmembrane Transport," 2009, Chem Eur J, 15:28-37.
Mascal, M., et al., "Fluoride-Selective Host Based on Anion-Pi Interactions, Ion Pairing, and Hydrogen Bonding: Synthesis and Fluoride-Ion Sandwich Complex," 2007, Angew Chem Int Ed, 46:8782-8784.
Mascal, M., "Precedent and Theory Unite in the Hypothesis of a Highly Selective Fluoride Receptor," 2006, Angew Chem Int Ed, 45:2890-2893.
Needham, R., "Fluoride Detection with the Naked Eye," 2006, Highlights in Chemical Technology, RCS Publishing, 1 page.
Peng, X., et al., "Colorimetric and Ratiometric Fluorescence Sensing of Fluoride: Tuning Selectivity in Proton Transfer," 2005, JOC, 70:10524-10531.
Quinonero, D., et al., "Anion-Pi Interactions: Do They Exist," 2002, Angew Chem Int Ed, 41/18:3389-3392.
Reed, A.E., et al., "Natural Localized Molecular Orbitals," 1985, J Chem Phys, 83:1736-1740.
Rosokha, Y.S., et al., "Halide Recognition Through Diagnostic 'Anion-Pi' Interactions: Molecular Complexes of Cl-, Br-, and I- with Olefinic and Aromatic Pi Receptors," 2004, Angew Chem Int Ed, 43:4650-4652.
Sakai, N., et al., "Three-Component Zipper Assembly of Photoactive Cascade Architectures with Blue, Red and Colorless Naphthalenediimide Donors and Acceptors," 2008, Org Biomol Chem, 6:3970-3976.
Schottel, B.L., et al., "Anion-Pi Interactions," 2008, Chem Soc Ref, 37:68-83.
Suda, Y. et al., "Immobilization and Clustering of Structurally Defined Oligosaccharides for Sugar Chips: An Improved Method for Surface Plasmon Resonance Analysis of Protein-Carbohydrate Interactions," 2006, Bioconjugate Chem, 17:1125-1135.
Sun, H., et al., "Anhydrous Tetrabutylammonium Fluoride," 2005, JACS, 127:2050-2051.
Takeuchi, M., et al., "Allosteric Fluoride Anion Recognition by a Doubly Strapped Porphyrin," 2001, Angew Chem Int Ed, 40/18:3372-3376.
Towers, M.D.K.N., et al., "Addition of 2-[(Trimethylsilyloxy)]Furan to 2-Acetyl-1,4-Benzoquinone Using Chiral Non-Racemic Copper(II)-Pybox Catalysts," 2003, Arkivoc, i:43-55.
Tripier, R., et al., "Towards Fluoride Sensing with Positively Charged Lanthanide Complexes," 2010, Eur J Inorg Chem, 2735-2745.
Trivedi, D.R., et al., "Crystal Engineering Approach to Design Colorimetric Indicator Array to Discriminate Positional Isomers of Aromatic Organic Molecules," 2009, Chem Asian J, 4:254-261.
Wade, C.R., et al., "Fluoride Ion Complexation and Sensing Using Organoboron Compounds," 2010, Chem Rev, 110:3958-3984.
Yamaguchi, S., "Colorimetric Fluoride Ion Sensing by Boron-Containing Pi-Electron Systems," 2001, JAGS, 123/46:11372-11375.
Yoo, J., et al., "Selective Sensing of Anions with Calix[4]pyrroles Strapped with Chromogenic Dipyrrolyquinoxalines," 2009, JOC, 74:1065-1069.
Zhao, H., et al., "A Bidentate Lewis Acid with a Telluronium Ion as an Anion-Binding Site," 2010, Nat Chem, 2:984-990.

* cited by examiner (a)

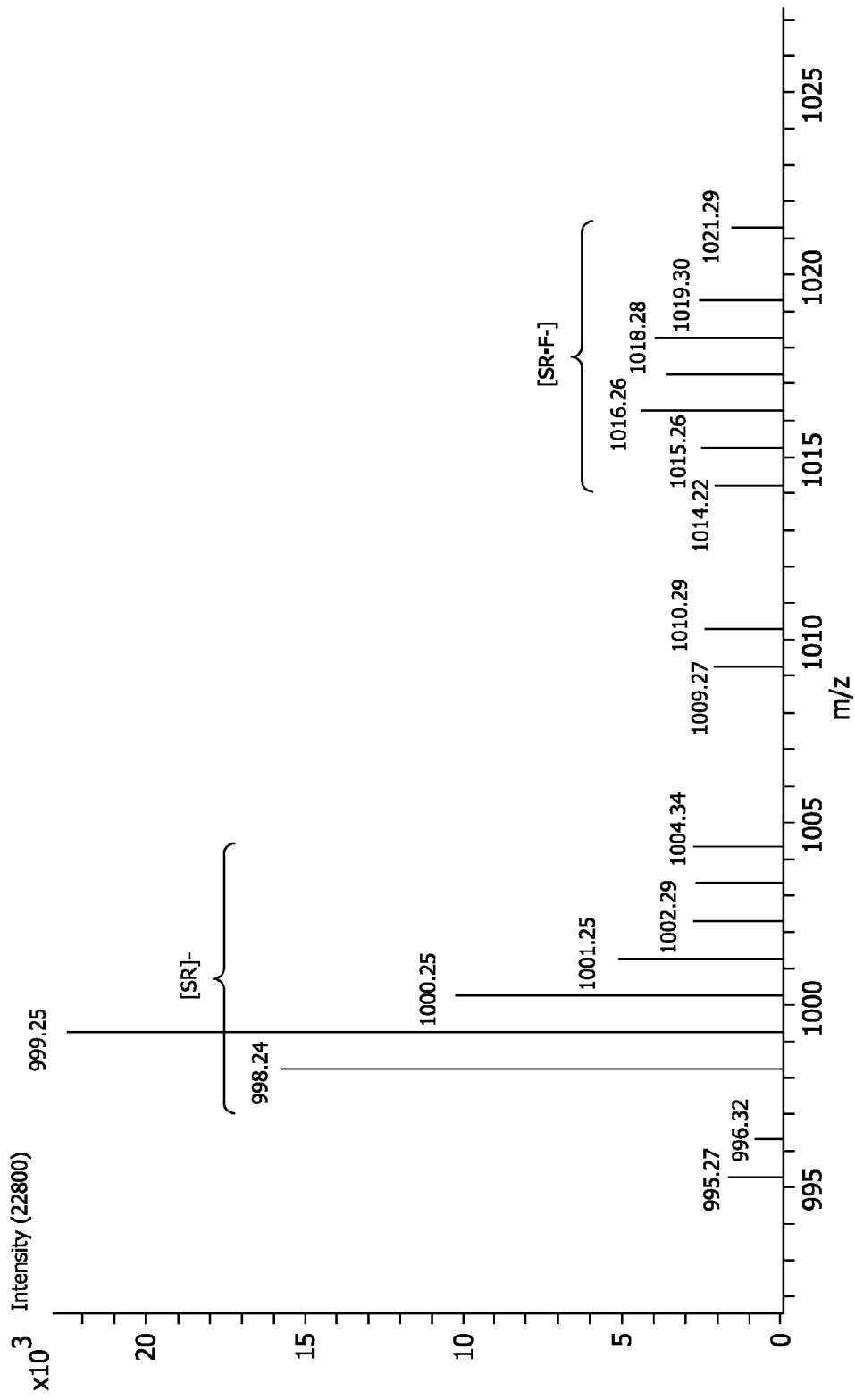

US 8,541,240 B2

COLORIMETRIC AND FLUORIMETRIC FLUORIDE SENSING

This application claims the benefit of U.S. provisional application Ser. No. 61/349,280, filed May 28, 2010, the entire contents of which is incorporated herein by reference.

FIELD OF THE INVENTION

The present invention generally relates to fluoride receptor reagent compounds and an associated method for the detection of fluoride in a composition.

BACKGROUND OF THE INVENTION

Fluoride is a biologically relevant anion. Insufficient dietary intake of fluoride results in poor dental health, osteosclerosis, and osteoporosis. On the other hand, excess fluoride intake is known to cause fluorosis, osteosarcoma, and arthritis. Alzheimer's disease is also believed to be associated with uptake of toxic aluminum fluoride through drinking water. Because heretofore there has been no simple and inexpensive way of detecting fluoride in water, a person may consume an undetermined amount of fluoride every day, which may enhance the risk for severe health conditions during the latter stages of life.

Water fluoridation, which involves the addition of $F^-$ to tap water, has been a common practice in the United States since the 1950s. Tap water fluoridation, however, has recently come under increased scrutiny. P. Connet, *Fluoride*, 2007, 40, 155-158; (b) R. J. Carton, *Fluoride*, 2006, 39, 163-172. The EPA recommends a minimum $F^-$ concentration in drinking water of 0.7 ppm, a level sufficient to provide benefits to dental and skeletal health. However, concentrations over 2 ppm are considered a risk to human health, and higher doses are known to cause the debilitating conditions listed above. Accordingly, proper maintenance of such a narrow $F^-$ concentration tolerance demands highly sensitive and selective detection techniques.

Generally, the sensing and detection of anions using non-covalent interaction, such as anion-π interaction, electrostatic and hydrogen bonding interaction, is an emerging area of current research. For example, it is known that a number of hydrogen bond (H-bond) donating receptors are able to bind $F^-$ anions via H-bond formation. Previous studies have described $F^-$ sensors using compounds based on urea, thiourea, amide, sulfonamide, pyrole, and indole, among others, which utilize this technique. Colorimetric sensing of fluoride is particularly desirable, and has previously been studied as a possible detection method for the nerve gas Sarin (GB) (isopropyl methylphosphonofluoridate), which loses a fluoride anion during hydrolysis. R. M. Black, J. M. Harrison, R. W. Read *Arch Toxicol* 1999, 73, 123-126.

Because of the non-chromogenic nature of most Y—H . . . X— H-bonds, however, hydrogen bond donating receptors either rely on adjacent chromophore units or deprotonation of acidic protons followed by electron delocalization to display colorimetric response. As a result, the fluoride detection mechanism is usually not reversible, and prevents the compounds from being easily reused. Furthermore, compounds using this mechanism rarely discriminate between strongly basic anions (e.g., $F^-$, acetate anion ($AcO^-$), and $H_2PO_4^-$), and often show poor selectivity and sensitivity for the $F^-$ anion as a result.

Comparatively, anion-π interaction mechanisms have received less research attention.

Maeda has reported a metal complex that showed a high association constant, $K_a$ for $F^-$ dissolved in dichloromethane ($>3 \times 10^5$ $M^{-1}$). This result was ascribed not only to the acidity of the NH peripheral group, but also to the anion-π interaction between the $F^-$ and the closest electron deficient fluorinated phenyl ring. Mascal has proposed novel cylindrophane-type receptors based on π-electron deficient rings, which demonstrate a high level of selectivity for $F^-$, both in the gas phase and in aqueous solvent model. See M. Mascal *Angew. Chem. Int. Ed.* 2006, 45, 2890-2893.

1,4,5,8-naphthalenediimides (NDIs) have attracted much attention due to their tendency to form n-type (over p-type) semiconductor materials, which are often used in applications such as electron donor-acceptor dyes and molecular machines. S. V. Bhosale, C. H. Jani, S. J. Langford *Chem. Soc. Rev.*, 2008, 37, 331-342. (b) H. E. Katz, A. J. Lovinger, C. Kloc, T. Siegrist, W. Li, Y.-Y. Lin, A. Dodabalapur, *Nature*, 2000, 404, 478-481. (c) N. Sakai, R. S. K. Kishore, S. Matile *Org. Biomol. Chem.*, 2008, 6, 3970-3976. However, the ability of NDI to interact with anions is relatively less explored.

Recently, Matile and coworkers have reported a synthetic ion channel based on NDI rods as transmembrane anion-π-slides. V. Gorteau, G. Bollot, J. Mareda, A. P.-Velasco, S. Matile *J. Am. Chem. Soc.* 2006, 128, 14788-14789 (b) J. Mareda, S. Matile *Chem. Eur. J.* 2009, 15, 28-37 (c) V. Gorteau, G. Bollot, J. Mareda, Stefan Matile *Org. Biomol. Chem.*, 2007, 5, 3000-3012. A core-substituted NDI based fluoride sensor has also been reported, in this case having a two-stage deprotonation process leading to a colorimetric response. S. V. Bhosale, S. V. Bhosale, M. B. Kalyankar, S. J. Langford *Org. Lett.* 2009, 11, 5418-5421.

Iverson and others demonstrated that charge transfer and π-π-stacking interactions, which occur between a colorless NDI unit and electron rich aromatic rings, produce donor-acceptor charge transfer complexes having a colorimetric response. However, no research has previously investigated the effect of anion-π interaction between NDI units and $F^-$ anions.

A need persists in the art for a method of fluoride anion detection that has good sensitivity, shows high selectivity for fluoride, and is economical for widespread use.

SUMMARY OF THE INVENTION

Briefly, the present invention is directed to a method for detecting fluoride anion ($F^-$).

In one embodiment, the invention is directed to a method for detecting fluoride anion ($F^-$) in a material comprising:

contacting the material with a fluoride receptor reagent to form a complex involving anion-π interactions, wherein the fluoride receptor reagent comprises an N-aryl or heteroaryl derivative of 1,4,5,8-naphthalenediimide (NDI) having the formula (I):

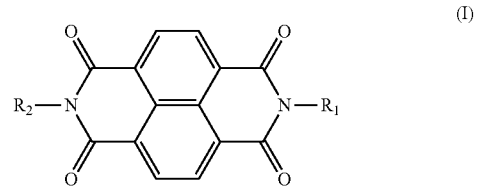

wherein $R_1$ comprises a substituted or unsubstituted aryl or heteroaryl moiety; and $R_2$ is independently a substituted or unsubstituted aryl or heteroaryl moiety, or $R_2$ comprises a second NDI moiety comprising a second NDI unit and having the formula:

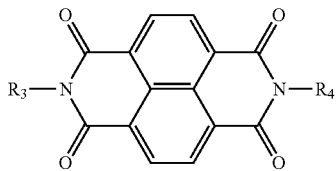

wherein $R_3$ is a linking group connecting the second NDI unit to the nitrogen atom of formula (I) and comprising a substituted or unsubstituted aryl or heteroaryl moiety; and $R_4$ is independently a substituted or unsubstituted aryl or heteroaryl moiety.

In another embodiment, the present invention is directed to a fluoride receptor reagent comprising an N-aryl or heteroaryl derivative of 1,4,5,8-naphthalenediimide (NDI) having the formula (I):

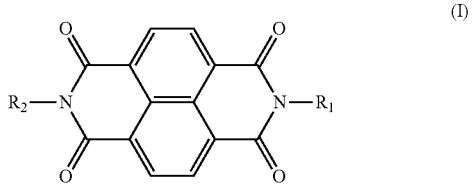

wherein $R_1$ comprises a substituted or unsubstituted aryl or heteroaryl moiety; and $R_2$ is independently a substituted or unsubstituted aryl or heteroaryl moiety, or $R_2$ comprises a second NDI moiety comprising a second NDI unit and having the formula:

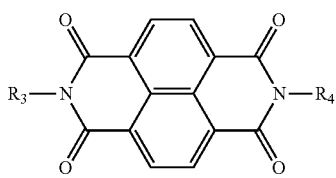

wherein $R_3$ is a linking group connecting the second NDI unit to the nitrogen atom of formula (I) and comprising a substituted or unsubstituted aryl or heteroaryl moiety; and $R_4$ is independently a substituted or unsubstituted aryl or heteroaryl moiety.

Other objects and features will be in part apparent and in part pointed out hereinafter.

BRIEF DESCRIPTION OF THE DRAWINGS

FIG. 9A shows data representing the presence and isotope distribution patterns of species [N1]$^-$ and [N1.F$^-$], while FIG. 9B depicts similar data for the species [N1.N1]$^-$ and [N1.F$^-$.N1]. FIG. 9C depicts data for the [N1]$^{2-}$ dianion in the presence of excess F$^-$.

FIGS. 9D and 9E are representations of the data collected using the ESI-MS procedure set forth in Example 10 for reagents SR and LR, respectively. More particularly, FIG. 9D shows data representing the presence and isotope distribution patterns of species [SR]$^-$ and [S.F$^-$], while FIG. 9E depicts similar data for the species [LR]$^-$ and [LR.F$^-$].

FIG. 9F shows data representing the presence and isotope distribution patterns of species [SR.2F$^-$], while FIG. 9G depicts similar data for the species [LR.2F$^-$].

FIG. 11 is a representation of the data collected using the spectroelectrochemistry procedure set forth in Example 13 for reagent N1. More particularly, panel (a) depicts the spectroscopic changes of N1 (0.5 mM in 0.1 M $Bu_4NPF_6$/DMF) at $E_{ap}=-450$ mV versus Ag/AgCl (3 N aq. NaCl), and shows the formation of the $N1.^-$ radical anion. The panel (a) inset also depicts a cyclic voltammogram of N1, which shows distinct one-electron reductions of N1 to the $N1.^-$ radical anion, and from the $N1.^-$ radical anion to the $N1^{2-}$ dianion. Panel (b) depicts the spectroscopic changes of N1 at $E_{ap}=-900$ mV versus Ag/AgCl (3 N aq. NaCl), and shows the formation of the $N1^{2-}$ dianion under the conditions set forth in Example 13.

Figure 12:
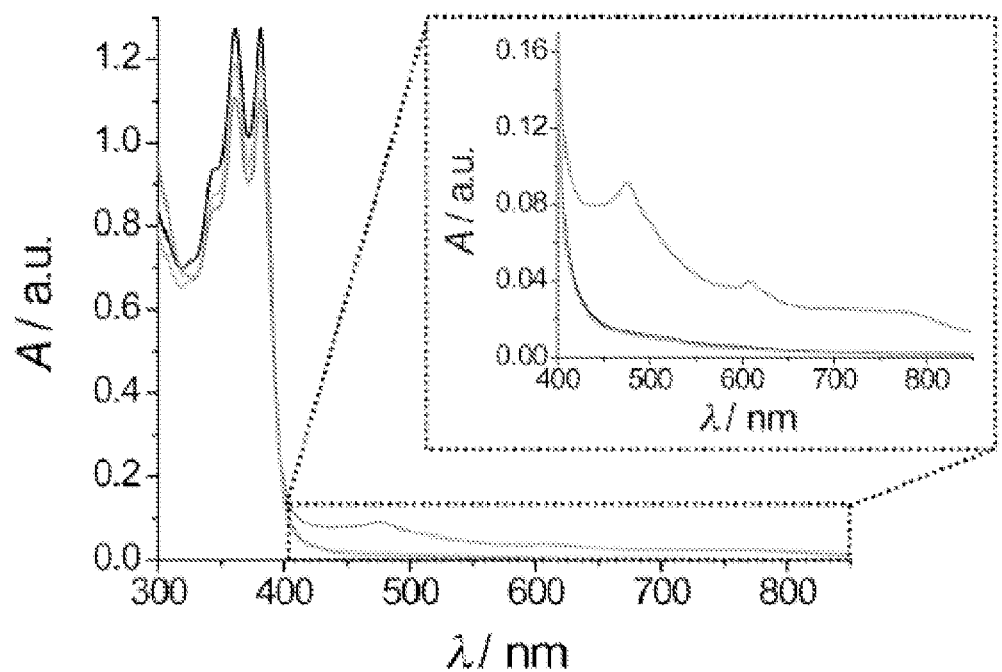

FIG. 12 is a representation of the UV/Visible light spectroscopy data collected using the experimental procedure set forth in Example 15, wherein the fluoride concentration in toothpaste was tested using reagent SR.

Figure 13:
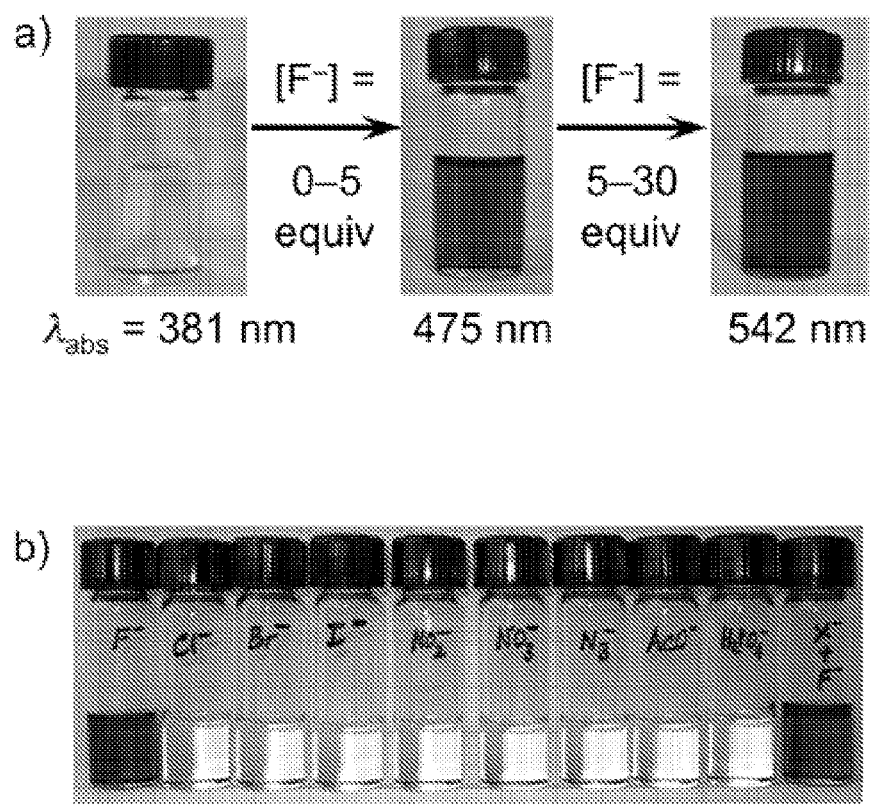

FIG. 13 is a representation of the colorimetric changes of reagent N1 in the presence of fluoride anions. More particularly, panel (a) depicts changes from colorless, to orange, to pink in response to increasing concentrations of fluoride anion. Panel (b) depicts the lack of a color change in response to solutions comprising other anions in DMSO.

Figure 14:
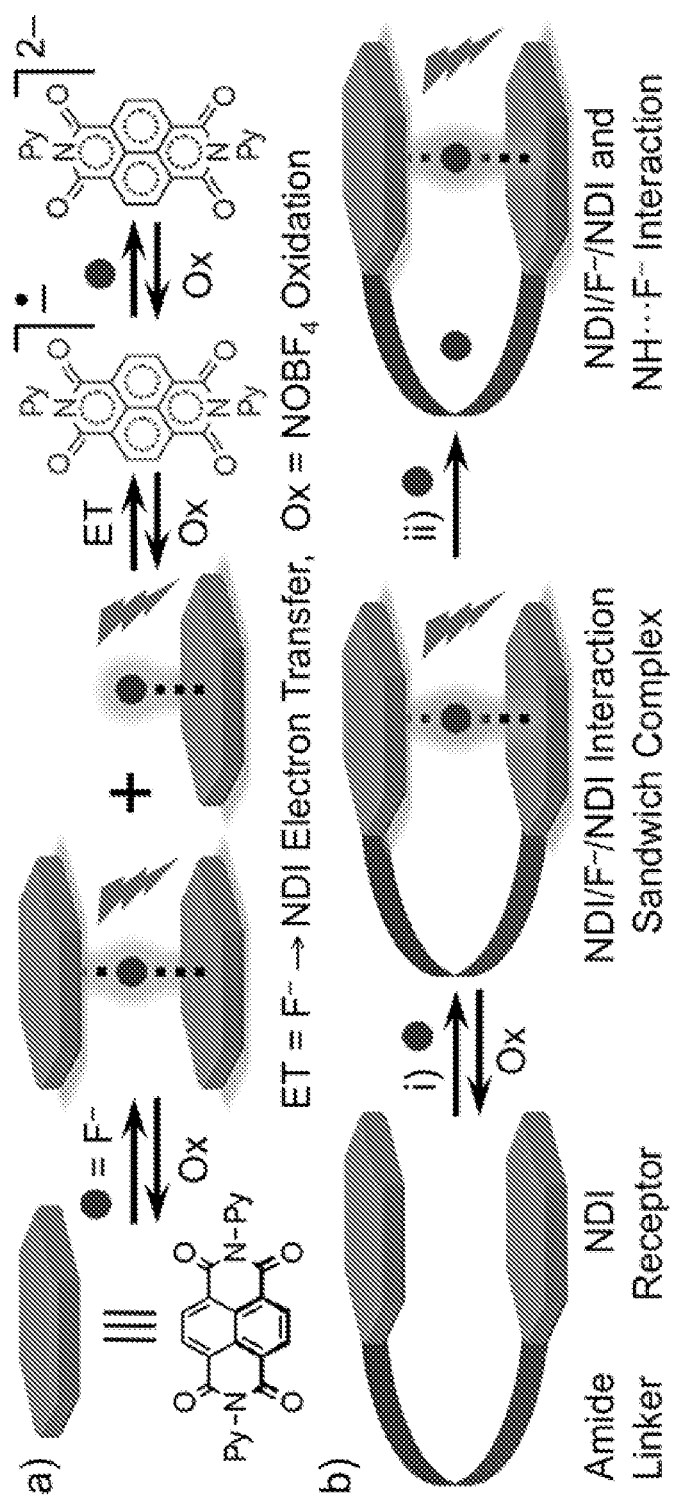

FIG. 14 is a graphical illustration of the reactions between fluoride anions and the fluoride receptor reagents of the present invention. More particularly, panel (a) is a graphical illustration of the anion-π and ET interactions between $F^-$ and the N1 receptor, generating fluorochromogenic response via an $F^- \rightarrow$NDI ET event. Panel (b) is a graphical illustration of the stepwise $F^-$ recognition by species SR through (i) π-anion-π and (ii) H-bonding interactions.

Figure 15:
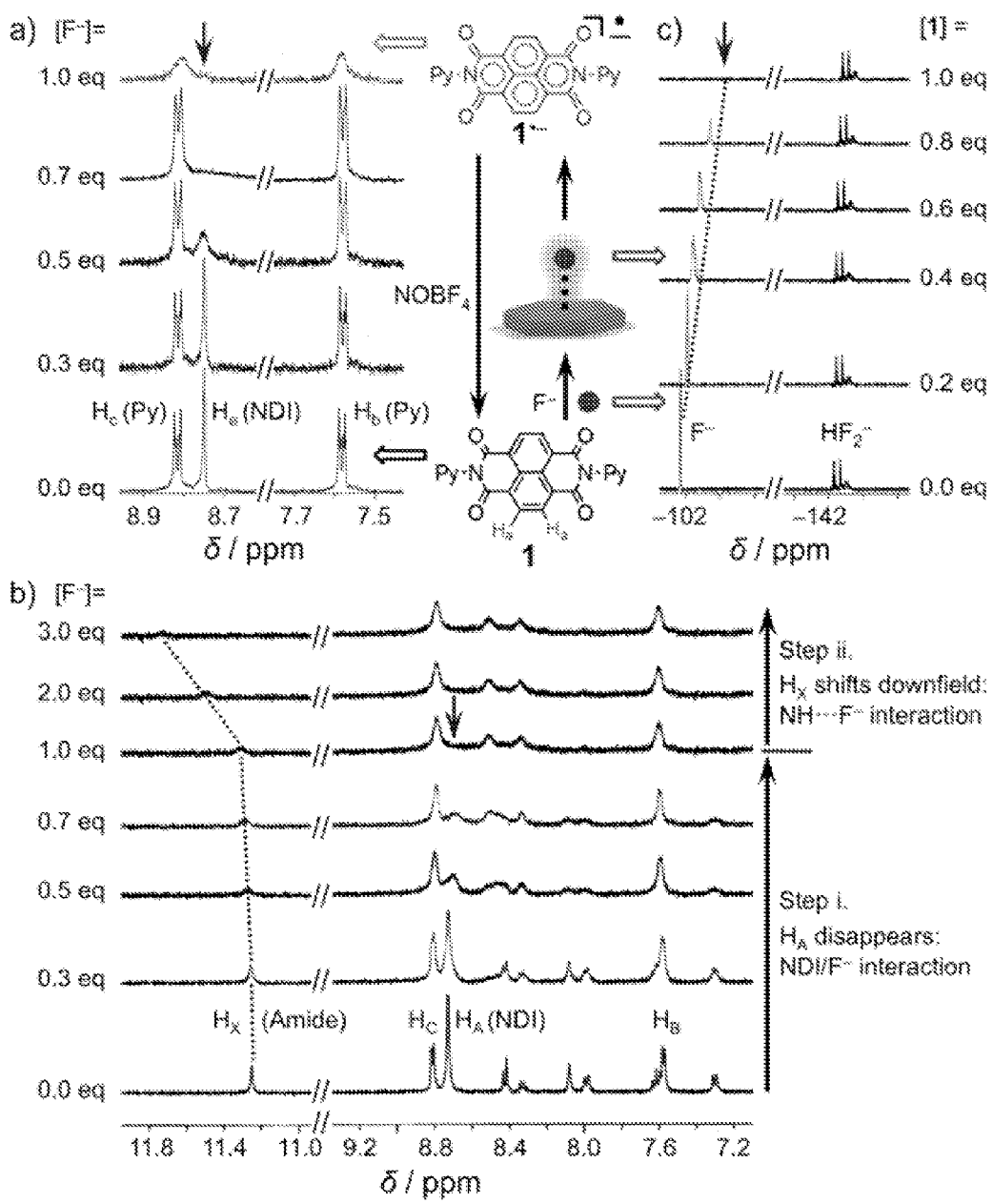

FIG. 15 is a representation of the data collected using nuclear magnetic resonance experimental procedures described in Examples 6 and 9, which involve $^1$H NMR and $^{19}$F NMR, respectively. Panels (a) and (b) disclose $^1$H NMR results for reagents N1 and SR, respectively, while panel (c) discloses $^{19}$F NMR results for reagent N1.

Figure 16:
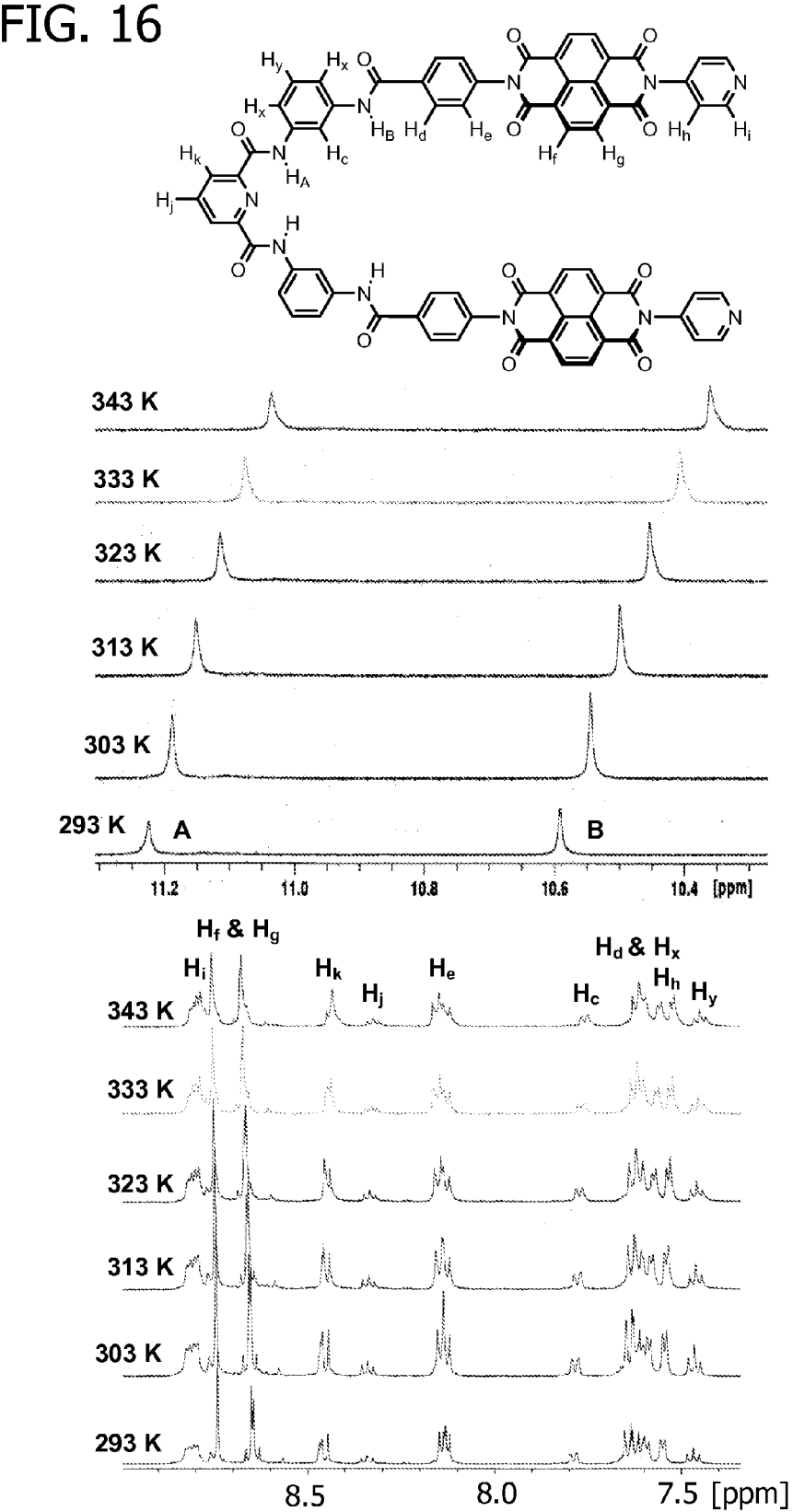
Figure 17:
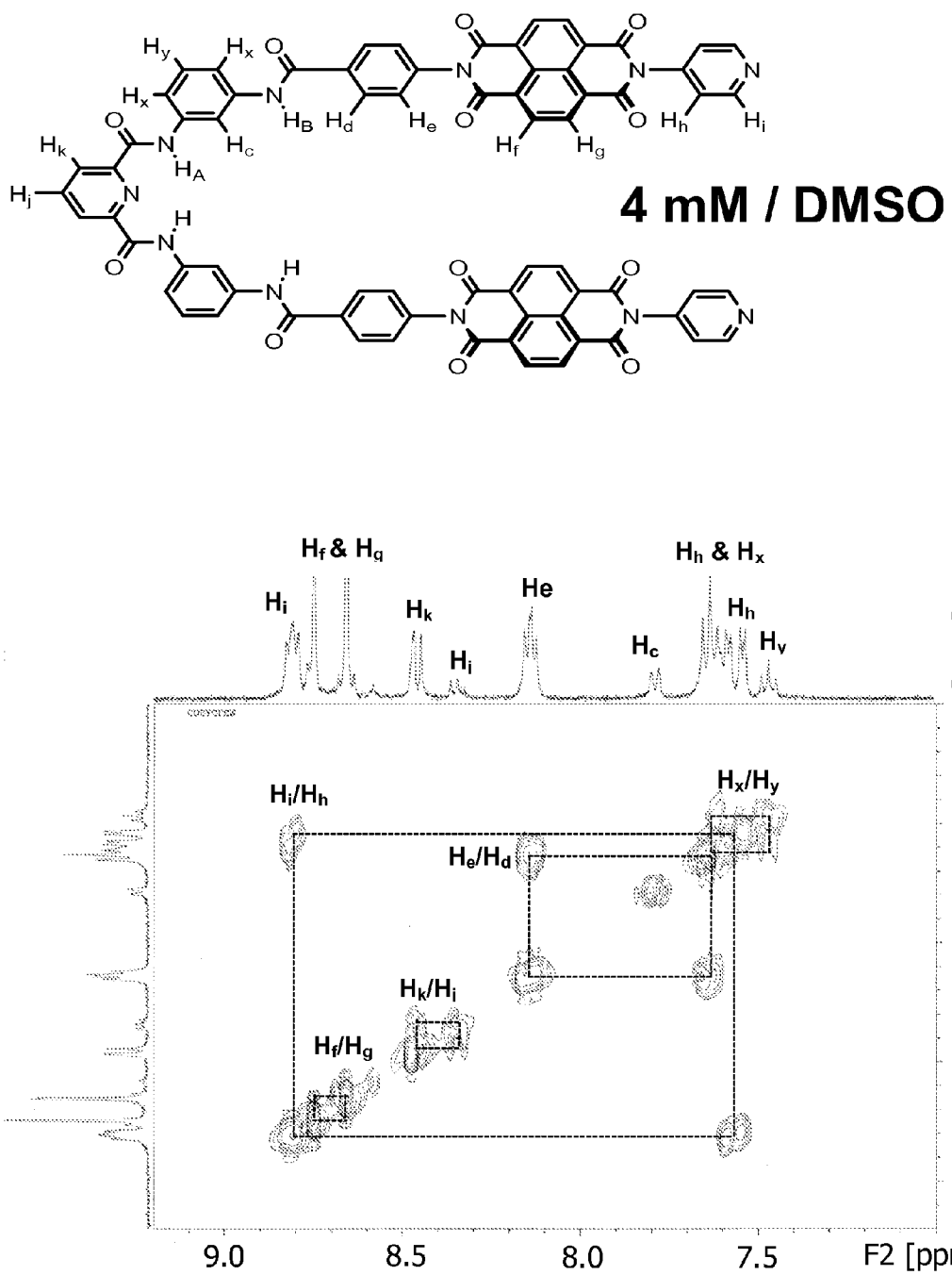
Figure 18:
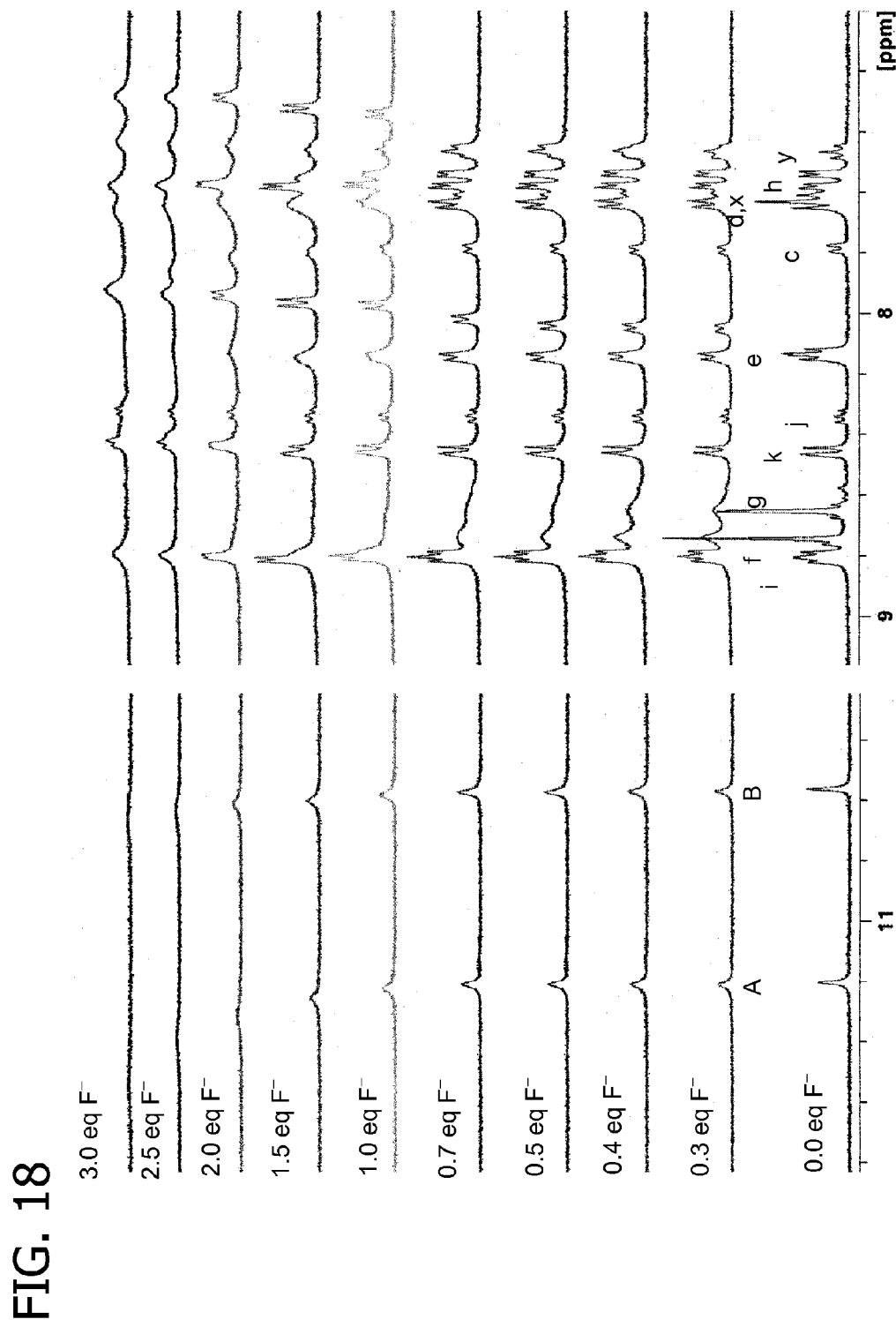

FIGS. 16-18 are representations of the data collected using the solution-state $^1$H NMR study set forth in Example 5 for reagent LR.

DETAILED DESCRIPTION OF THE EMBODIMENTS OF THE INVENTION

It has been discovered that certain 1,4,5,8-naphthalenediimide-based compounds address the deficiencies in the prior art by providing a novel method of fluoride anion detection and fluoride receptor reagents for use in the method. The present invention provides a highly selective and sensitive fluoride anion sensor that enables visual and quantitative detection of fluoride anion from mM to nM concentrations.

In part, the present invention relates to π-anion-π interactions involving fluoride anion and fluoride receptor reagents, which include compounds comprising one or more N-aryl or heteroaryl substituted 1,4,5,8-naphthalenetetracarboxydiimide (NDI) units. It has been discovered that these interactions are able to generate concentration-dependent vibrant colors and fluorescence amplifications, thereby providing a means for detecting the presence and concentration of $F^-$ anions. Without being bound to any particular theory, it is believed that the chromogenic sensing mechanism of these compounds relies on a novel anion-π interaction involving electron-rich fluoride anions and N-aryl or heteroaryl NDI derivatives that possess positive quadrupole moments.

As further detailed in the examples presented below, this interaction has been extensively investigated through the use of nuclear magnetic resonance (NMR), electron paramagnetic resonance (EPR), ultraviolet/visible spectroscopy (UV/Vis), fluorescence spectroscopy, spectroelectrochemistry (SEC), electrospray ionization mass spectroscopy (ESI-MS), and isothermal titration calorimetry (ITC) experimental techniques. It is believed that the interactions between $F^-$ anions and the novel fluoride receptor reagents described herein involve an electron transfer process from the electron-rich $F^-$ anion to the electron-deficient NDI receptors. Although the neutral NDI receptor units are colorless, this electron transfer event is believed to generate orange $NDI.^-$ radical anions and pink $NDI^{2-}$ dianion, resulting in a gradual color change that is proportionate to the initial concentration of $F^-$ ions.

Accordingly, the fluoride receptor reagents of the present invention may be exploited for the detection of various levels of $F^-$ ion concentrations in drinking water, consumer products, and/or in bone and muscle tissues for early detection and prevention of $F^-$ ion-related diseases.

A. Fluoride Receptor Reagents

The fluoride receptor reagents of the present invention generally include compounds comprising N-aryl or heteroaryl substituted 1,4,5,8-naphthalenetetracarboxydiimide (NDI) units. As discussed above, it has been discovered that the π-electron orbitals present in the NDI units form a complex with fluoride anions. It is believed that the anion-π interaction results in a charge transfer process between the fluoride anion and the NDI unit, resulting in a number of measurable effects (e.g., colorimetric response).

In view of the mechanism outlined above, the method of the present invention can be practiced with any N-aryl or heteroaryl derivative of 1,4,5,8-naphthalenetetracarboxydiimide. Put another way, any electron deficient aryl or heteroaryl derivative of 1,4,5,8-naphthalenetetracarboxydiimide (e.g., p-benzoic acid derivatives) will produce similar colorimetric and spectroscopic changes in the presence of $F^-$ anions.

Generally, the fluoride receptor reagents of the present invention comprise compounds having the following formula (I):

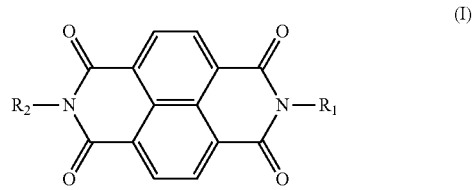

wherein $R_1$ comprises a substituted or unsubstituted aryl or heteroaryl moiety; and $R_2$ is independently a substituted or unsubstituted aryl or heteroaryl moiety. Furthermore, in preferred embodiments described in greater detail below, the fluoride receptor reagents comprise two or more overlapping NDI units, such that $R_2$ alternatively comprises a second NDI moiety comprising a second NDI unit and having the formula:

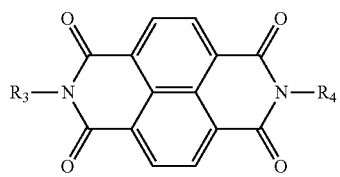

wherein R₃ is a linking group connecting the second NDI unit to the nitrogen atom of formula (I) and comprising a substituted or unsubstituted aryl or heteroaryl moiety; and R₄ is independently a substituted or unsubstituted aryl or heteroaryl moiety. A heteroaryl moiety includes at least one hetero atom (e.g., sulfur, oxygen, and/or nitrogen). Substituents on the aryl or heteroaryl-comprising moieties $R_1$, $R_2$, $R_3$ and $R_4$ may independently be selected, without limitation, from halo (e.g., F, Cl, Br and I), —OH, =O, —C(O)OH, —C(O)OR₇, —C(O)NR₈R₉, —CH₂NR₈R₉, nitro (—NO₃), sulfonate (—SO₉⁻) hydrocarbyl and substituted hydrocarbyl for example, alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl and heteroarylalkyl, in each case optionally substituted. $R_7$, $R_8$, and $R_9$ are each independently hydrocarbyl or substituted hydrocarbyl.

For example, in one embodiment, the fluoride receptor reagent comprises a compound of the formula (N1):

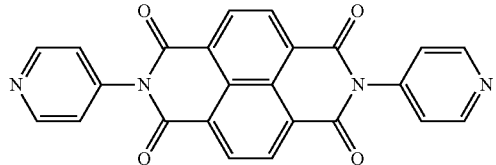

(N1)

This compound is sometimes hereinafter referred to as "reagent N1," or simply "N1".

In further examples, the fluoride receptor reagent comprises a compound of the structures (I-A) through (I-E). For example, in one embodiment, the fluoride receptor reagent comprises a compound of formula (I-A):

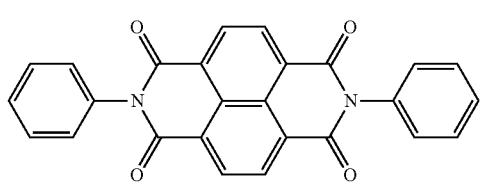

(I-A)

In another embodiment, the fluoride receptor reagent comprises a compound of formula (I-B):

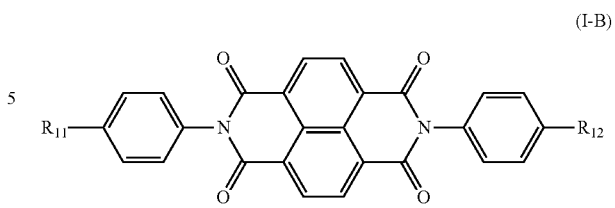

(I-B)

wherein $R_{11}$ and $R_{12}$ are each independently alkyl, alkyl ether, or nitro (NO₂) functional groups. In one embodiment, $R_{11}$ and $R_{12}$ are both methyl groups. In another embodiment, $R_{11}$ and $R_{12}$ are both methyl ether (—OCH₃) groups. In another embodiment, $R_{11}$ and $R_{12}$ are both nitro (NO₂) groups.

In another embodiment, the fluoride receptor reagent comprises a compound of formula (I-C):

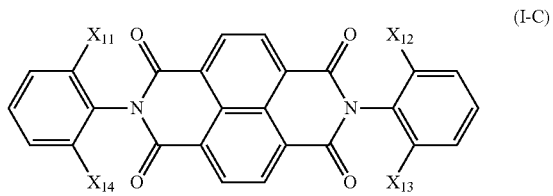

(I-C)

wherein $X_{11}$, $X_{12}$, $X_{13}$, and $X_{14}$ are each independently halo (e.g., F, Cl, Br and I). In one embodiment, $X_{11}$, $X_{12}$, $X_{13}$, and $X_{14}$ are each fluorine. In another embodiment, $X_{11}$, $X_{12}$, $X_{13}$, and $X_{14}$ are each chlorine. In another embodiment, $X_{11}$, $X_{12}$, $X_{13}$, and $X_{14}$ are each bromine.

In another embodiment, the fluoride receptor reagent comprises a compound of formula (I-D):

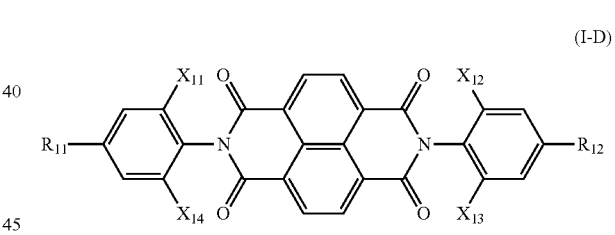

(I-D)

wherein $X_{11}$, $X_{12}$, $X_{13}$, and $X_{14}$ are each independently halo, as described above, and $R_{11}$ and $R_{12}$ are each independently alkyl, alkyl ether, or nitro functional groups, as described above. In one embodiment, $X_{11}$, $X_{12}$, $X_{13}$, and $X_{14}$ are each iodine, and $R_{11}$ and $R_{12}$ are both methyl groups. In another embodiment, $X_{11}$, $X_{12}$, $X_{13}$, and $X_{14}$ are each iodine, and $R_{11}$ and $R_{12}$ are both nitro (NO₂) groups.

In another embodiment, the fluoride receptor reagent comprises a compound of formula (I-E):

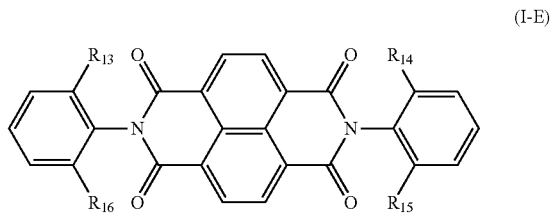

(I-E)

wherein $R_{13}$, $R_{14}$, $R_{15}$, and $R_{16}$ are each independently alkyl or alkyl ether groups. In one embodiment, $R_{13}$, $R_{14}$, $R_{15}$, and $R_{16}$ are each methyl groups. In another embodiment, $R_{13}$, $R_{14}$, $R_{15}$, and $R_{16}$ are each ethyl groups. In another embodiment, $R_{13}$, $R_{14}$, $R_{15}$, and $R_{16}$ are each isopropyl groups.

Each of the specific embodiments outlined above is symmetric with respect to the choice of substituents (e.g., the moieties corresponding to $R_1$ and $R_2$ in formula (I)). It should be emphasized, however, that in each of the embodiments outlined above, the substituents may be selected independently. Accordingly, fluoride receptor reagents that comprise asymmetric compounds are within the scope of the present invention.

In contrast to the N-aryl or heteroaryl derivatives described above, N-alkyl derivatives of NDI are significantly less effective. For example, most N-alkyl derivatives do not show immediate color change, even in the presence of relatively high concentrations of fluoride. This is presumably because the NDI cores in N-alkyl derivatives are less electron deficient, and therefore provide weaker anion-π interaction with fluoride.

A.1. Preferred Reagents Having Multiple NDI Units

In preferred embodiments, the present invention is directed to fluoride receptor reagents having two or more overlapping NDI units, which are preferably connected via folded linkers. These compounds "preorganize" multiple NDI units into overlapping positions or "tweezers," and allow the F⁻ anion to complex with both NDI units simultaneously. The formation of a π-anion-π interaction improves the selectivity and sensitivity for the F⁻ anion significantly, because it allows a stronger fluoride complexation between the NDI units and nM binding ($K_d$) to be achieved.

Generally, the preferred fluoride receptor reagents of the present invention comprise compounds having the formula (II):

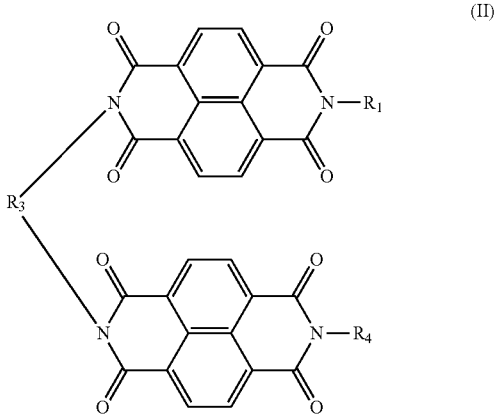

wherein $R_1$ and $R_4$ are each independently a substituted or unsubstituted aryl or heteroaryl moiety, as described above; and $R_3$ is a linking group comprising a substituted or unsubstituted aryl or heteroaryl moiety, as described above. For example, $R_1$, $R_3$ and $R_4$ may each independently comprise an aryl or heteroaryl moiety having generally from 4 to 18 carbon atoms, preferably from 4 to 10 carbon atoms.

In one embodiment, the $R_3$ linking group comprises a pyridyl moiety. It has been discovered that the presence of a central pyridine dicarboxamide moiety plays an important role in the formation of two five-member intramolecular hydrogen bonded rings, thereby causing the compound's internal cavity to become Lewis acidic. This structure causes the F⁻ anions to become more strongly complexed within the Lewis acid cavity through additional NH . . . F⁻ hydrogen bonding.

In view thereof, the two 1,4,5,8-naphthalenetetracarboxydiimide (NDI) units may be linked through a pyridyl linker, either directly bonded to the pyridyl moiety or through additional linking substituents, such as in the following formula (III):

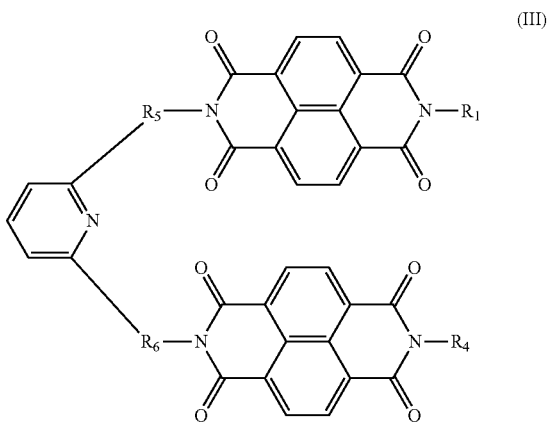

wherein $R_5$ and $R_6$ are each independently intermediate linking groups comprising a substituted or unsubstituted aryl or heteroaryl moiety, as described above. Preferably, the intermediate linking groups comprise 1 or more aryl moieties, such as 1, 2, 3, 4 or more aryl moieties having from about 4 to about 14 carbon atoms, preferably from 6 to 10, more preferably benzene rings. In some embodiments, the intermediate linking groups between the pyridyl linker and the two 1,4,5,8-naphthalenetetracarboxydiimide (NDI) units each comprise one or more benzene rings. In some embodiments, the one or more benzene rings of the intermediate linking groups are joined to each other and to the pyridyl linker via amide groups.

In one preferred embodiment, the fluoride receptor reagent comprises a compound of the formula (SR):

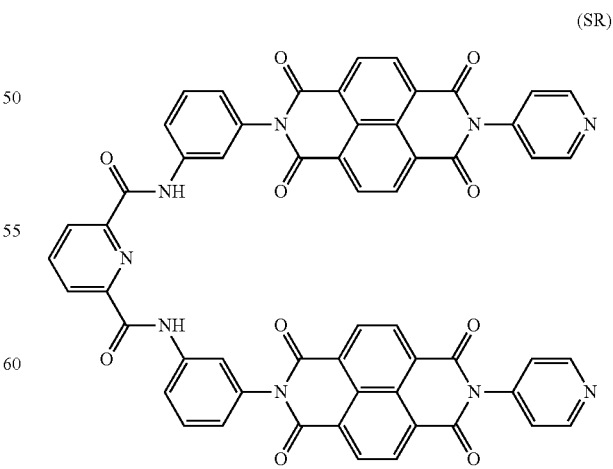

In another preferred embodiment, the fluoride receptor reagent comprises a compound of the formula (LR):

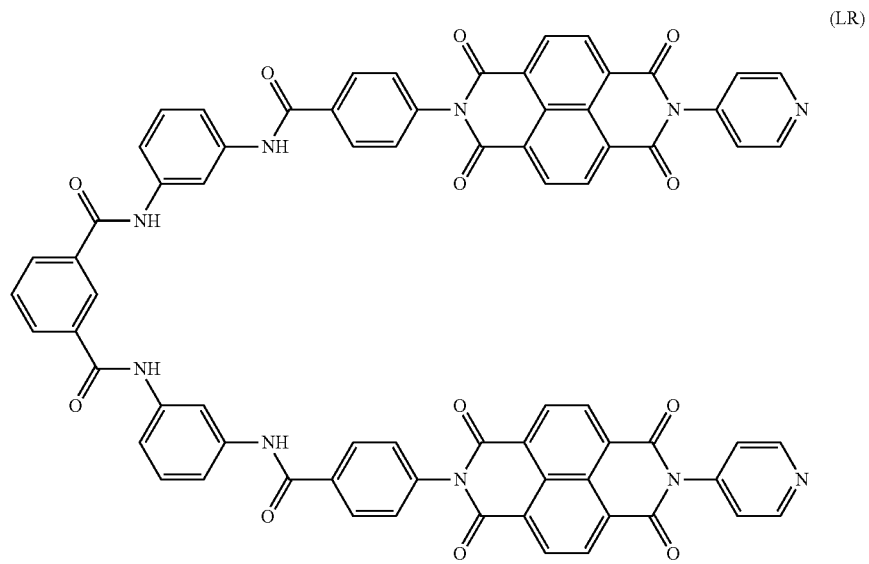 [SMILES: O=C(Nc1cccc(NC(=O)c2cccc(C(=O)Nc3cccc(NC(=O)c4ccc(N5C(=O)c6ccc7c8c(ccc(c68)C5=O)C(=O)N(c5ccncc5)C7=O)cc4)c3)c2)c1)c1ccc(N2C(=O)c3ccc4c5c(ccc(c35)C2=O)C(=O)N(c2ccncc2)C4=O)cc1]

(LR)

The compound of formula (SR) is sometimes hereinafter referred to as a "short receptor," or simply "SR", comprising a bisamide linking group connecting two NDI units. Similarly, the compound of formula (LR) is sometimes hereinafter referred to as a "long receptor," or simply "LR", comprising a tetraamide linking group between two NDI units.

With respect to these two compounds, the bifurcated intramolecular H-bonds involving the pivotal pyridine N atom and adjacent amide protons serve to render the bis- and tetraamide linkers folded conformations, thereby bringing the two ends of the receptor molecules into close proximity. Hartree-Fock global energy minimization shows that while the short linker SR brings two NDI units in parallel overlapping orientation, the longer linker LR projects two NDI at an angle. In addition to properly orienting NDI units, amide linkers SR and LR provide additional anion binding sites in their cavities via H-bonding interaction.

In further examples, the fluoride receptor reagent comprises a compound of the structures (III-A) through (III-K). For example, in one embodiment, the fluoride receptor reagent comprises a compound of formula (III-A):

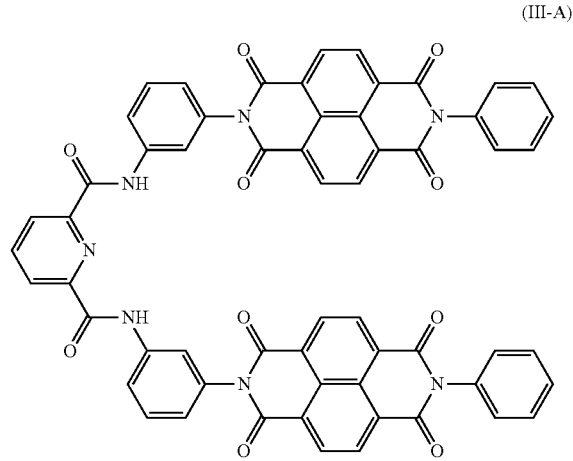 [SMILES: O=C(Nc1cccc(N2C(=O)c3ccc4c5c(ccc(c35)C2=O)C(=O)N(c2ccccc2)C4=O)c1)c1cccc(C(=O)Nc2cccc(N3C(=O)c4ccc5c6c(ccc(c46)C3=O)C(=O)N(c3ccccc3)C5=O)c2)n1]

(III-A)

In another embodiment, the fluoride receptor reagent comprises a compound of formula (III-B):

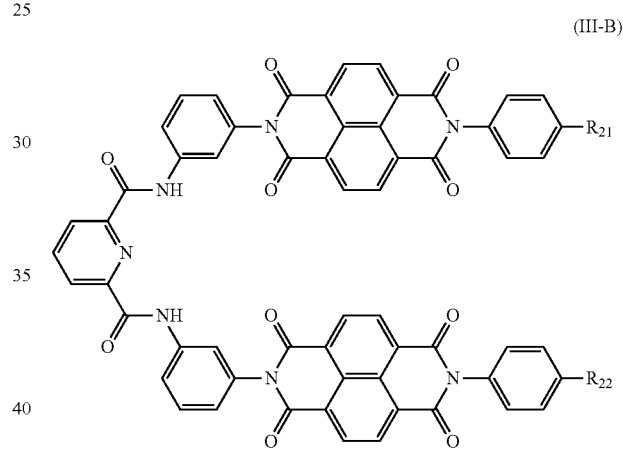

(III-B)

wherein $R_{21}$ and $R_{22}$ are each independently alkyl, alkyl ether, or nitro ($NO_2$) functional groups. In one embodiment, $R_{21}$ and $R_{22}$ are both methyl groups. In another embodiment, $R_{21}$ and $R_{22}$ are both methyl ether (—$OCH_3$) groups. In another embodiment, $R_{21}$ and $R_{22}$ are both nitro ($NO_2$) groups.

In another embodiment, the fluoride receptor reagent comprises a compound of formula (III-C):

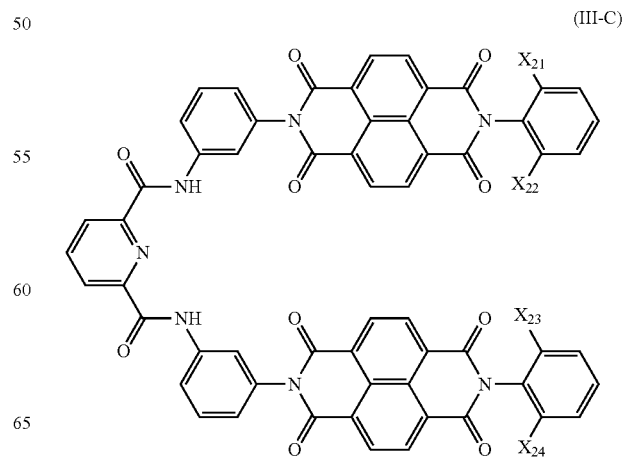

(III-C)

wherein $X_{21}$, $X_{22}$, $X_{23}$, and $X_{24}$ are each independently halo (e.g., F, Cl, Br and I). In one embodiment, $X_{21}$, $X_{22}$, $X_{23}$, and $X_{24}$ are each fluorine. In another embodiment, $X_{21}$, $X_{22}$, $X_{23}$, and $X_{24}$ are each chlorine. In another embodiment, $X_{21}$, $X_{22}$, $X_{23}$, and $X_{24}$ are each bromine.

In another embodiment, the fluoride receptor reagent comprises a compound of formula (III-D):

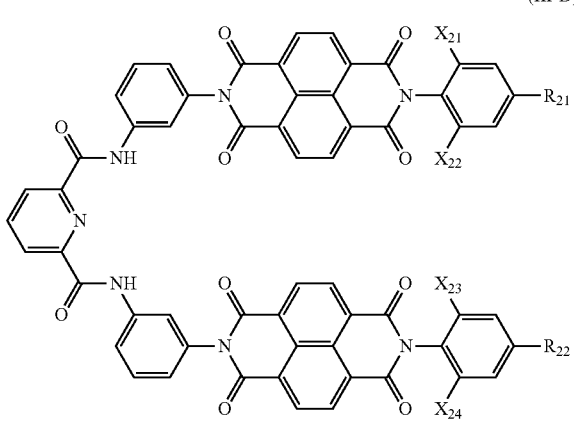

(III-D)

wherein $X_{21}$, $X_{22}$, $X_{23}$, and $X_{24}$ are each independently halo, as described above, and $R_{21}$ and $R_{22}$ are each independently alkyl, alkyl ether, or nitro functional groups, as described above. In one embodiment, $X_{21}$, $X_{22}$, $X_{23}$, and $X_{24}$ are each iodine, and $R_{21}$ and $R_{22}$ are both methyl groups. In another embodiment, $X_{21}$, $X_{22}$, $X_{23}$, and $X_{24}$ are each iodine, and $R_{21}$ and $R_{22}$ are both nitro ($NO_2$) groups.

In another embodiment, the fluoride receptor reagent comprises a compound of formula (III-E):

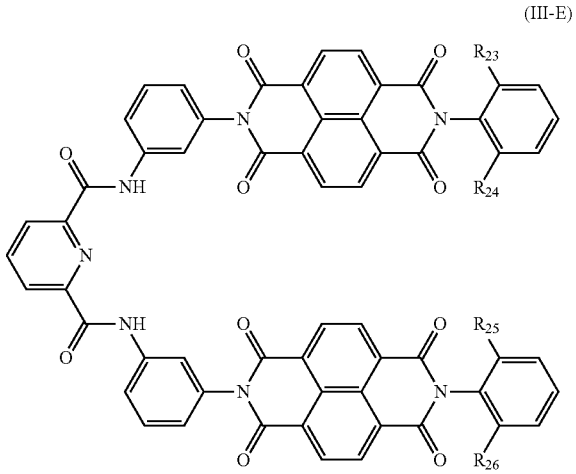

(III-E)

wherein $R_{23}$, $R_{24}$, $R_{25}$, and $R_{26}$ are each independently alkyl or alkyl ether groups. In one embodiment, $R_{23}$, $R_{24}$, $R_{25}$, and $R_{26}$ are each methyl groups. In another embodiment, $R_{23}$, $R_{24}$, $R_{25}$, and $R_{26}$ are each ethyl groups. In another embodiment, $R_{23}$, $R_{24}$, $R_{25}$, and $R_{26}$ are each isopropyl groups.

In another embodiment, the fluoride receptor reagent comprises a compound of formula (III-F):

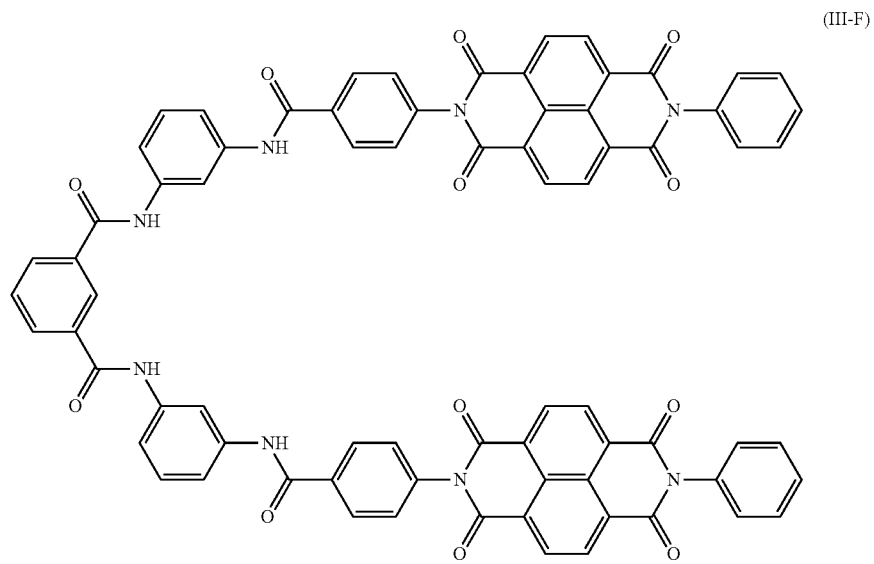

(III-F)

In another embodiment, the fluoride receptor reagent comprises a compound of formula (III-G):

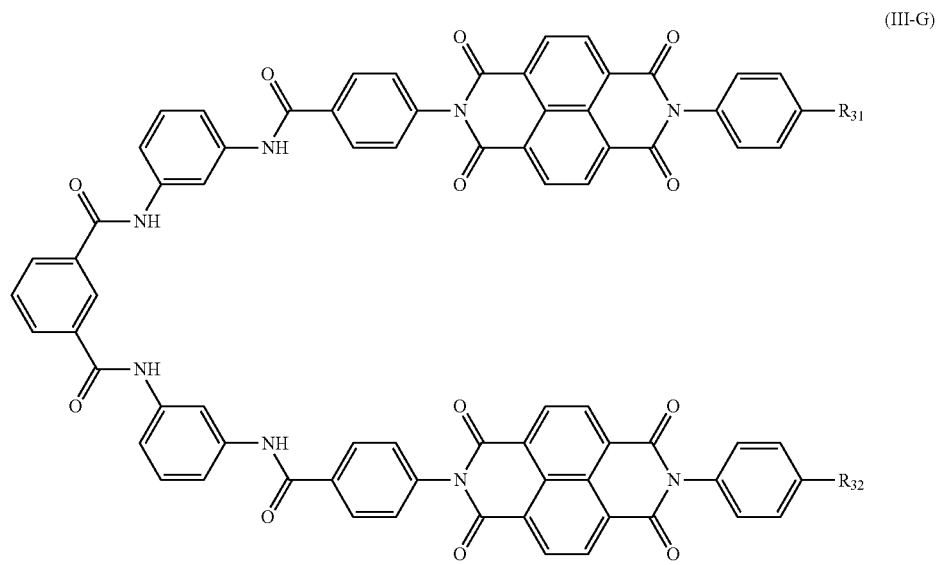

(III-G)

wherein $R_{31}$ and $R_{32}$ are each independently alkyl, alkyl ether, or nitro ($NO_2$) functional groups. In one embodiment, $R_{31}$ and $R_{32}$ are both methyl groups. In another embodiment, $R_{31}$ and $R_{32}$ are both methyl ether (—$OCH_3$) groups. In another embodiment, $R_{31}$ and $R_{32}$ are both nitro ($NO_2$) groups.

In another embodiment, the fluoride receptor reagent comprises a compound of formula (III-H):

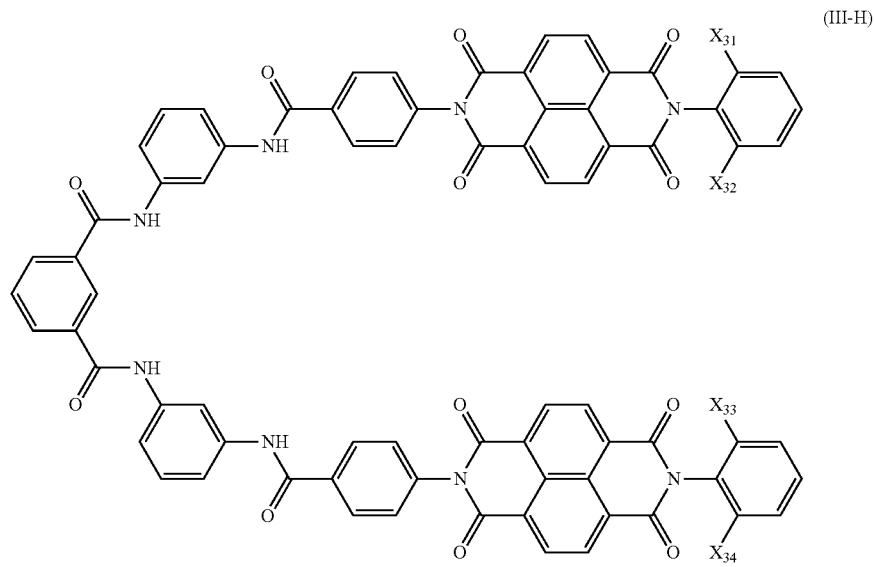

(III-H)

wherein $X_{31}$, $X_{32}$, $X_{33}$, and $X_{34}$ are each independently halo (e.g., F, Cl, Br and I). In one embodiment, $X_{31}$, $X_{32}$, $X_{33}$, and $X_{34}$ are each fluorine. In another embodiment, $X_{31}$, $X_{32}$, $X_{33}$, and $X_{34}$ are each chlorine. In another embodiment, $X_{31}$, $X_{32}$, $X_{33}$, and $X_{34}$ are each bromine.

In another embodiment, the fluoride receptor reagent comprises a compound of formula (III-J):

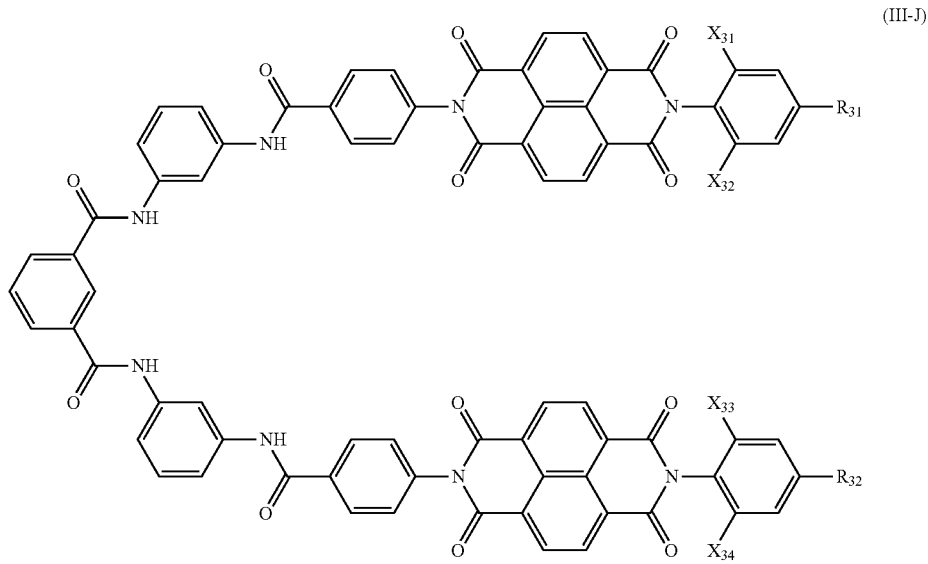

(III-J)

wherein $X_{31}$, $X_{32}$, $X_{33}$, and $X_{34}$ are each independently halo, as described above, and $R_{31}$ and $R_{32}$ are each independently alkyl, alkyl ether, or nitro functional groups, as described above. In one embodiment, $X_{31}$, $X_{32}$, $X_{33}$, and $X_{34}$ are each iodine, and $R_{31}$ and $R_{32}$ are both methyl groups. In another embodiment, $X_{31}$, $X_{32}$, $X_{33}$, and $X_{34}$ are each iodine, and $R_{31}$ and $R_{32}$ are both nitro ($NO_2$) groups.

In another embodiment, the fluoride receptor reagent comprises a compound of formula (III-K):

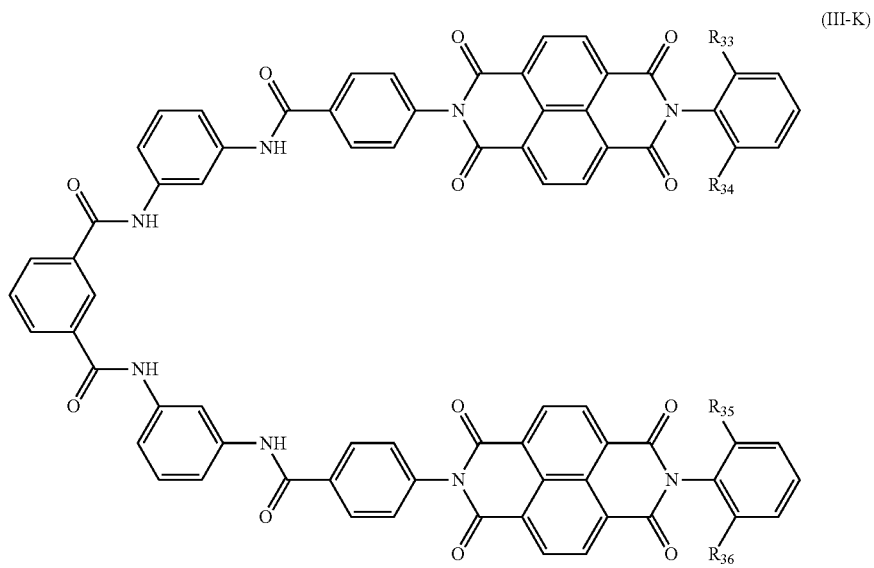

(III-K)

wherein $R_{33}$, $R_{34}$, $R_{35}$, and $R_{36}$ are each independently alkyl or alkyl ether groups. In one embodiment, $R_{33}$, $R_{34}$, $R_{35}$, and $R_{36}$ are each methyl groups. In another embodiment, $R_{33}$, $R_{34}$, $R_{35}$, and $R_{36}$ are each ethyl groups. In another embodiment, $R_{33}$, $R_{34}$, $R_{35}$, and $R_{36}$ are each isopropyl groups.

Each of the specific embodiments outlined above is symmetric with respect to the choice of substituents (e.g., the moieties corresponding to $R_1$ and $R_4$ in formula (III)). It should be emphasized, however, that in each of the embodiments outlined above, the substituents may be selected independently. Accordingly, fluoride receptor reagents that comprise asymmetric compounds are within the scope of the present invention.

A.2. Synthesis and Preparation

Generally, compounds having simple NDI-derivative moieties can be prepared using procedures known to those skilled in the art. For example, preparation of reagent N1, which is an N-heteroaryl derivative of 1,4,5,8-naphthalenetetracarboxydiimide, can be prepared by heating a 1:2 molar mixture of 1,4,5,8-naphthalene tetracarboxylic dianhydride (NTDA) and 4-amino pyridine under reflux in an appropriate solvent.

As described above, in preferred embodiments of the present invention, the fluoride receptor reagents have two or more overlapping NDI units, which are preferably connected via folded linkers.

As discussed above, the linking group is preferably prepared using starting compounds comprising a substituted or unsubstituted aryl or heteroaryl moiety. A heteroaryl moiety includes at least one hetero atom (e.g., sulfur, oxygen, and/or nitrogen). Substituents on the aryl or heteroaryl-comprising moieties $R_1$, $R_2$, $R_3$ and $R_4$ may independently be selected, without limitation, from halo (e.g., F, Cl, Br and I), —OH, =O, —C(O)OH, —C(O)O$R_7$, —C(O)N$R_8R_9$, —CH$_2$N$R_8R_9$, nitro (—NO$_3$), sulfonate (—SO$_3^-$) hydrocarbyl and substituted hydrocarbyl for example, alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl and heteroarylalkyl, in each case optionally substituted. $R_7$, $R_8$, and $R_9$ are each independently hydrocarbyl or substituted hydrocarbyl.

A detailed process for the preparation of certain preferred compounds is provided in Example 1. More generally, the preparation of suitable linking groups and fluoride receptor reagents can be accomplished using starting materials and processes generally known in the art of organic chemistry.

B. Methods of Detecting Fluoride

The fluoride receptor reagents of the present invention are able to signal the presence and concentration of fluoride anion via a number of independent detection methods. Generally, the anion-π interaction between fluoride anion and the receptor reagent compounds results in a charge transfer process that can be detected by the use of any of the following techniques: visual colorimetric response; ultraviolet/visible spectroscopy (UV/Vis); fluorescence spectroscopy; nuclear magnetic resonance (NMR); electron paramagnetic resonance (EPR); spectroelectrochemistry (SEC); electrospray ionization mass spectroscopy (ESI-MS); and/or isothermal titration calorimetry (ITC).

To determine the amount of fluoride present in a given material, the material to be tested can first be dissolved in an appropriate solvent. Generally, the receptor reagent compounds of the present invention are soluble in polar solvents. Because the reagent-fluoride complex is unstable in protic solvents, polar aprotic solvents are preferred. Non-limiting examples of preferred solvents include aqueous dimethyl sulfoxide (DMSO), dimethylformamide (DMF), dimethylacetamide (DMAc), acetonitrile (MeCN), acetone (Me$_2$CO), and tetrahydrofuran (THF). Although dry solvents are preferred, solvent solutions can generally contain up to 15% of H$_2$O by weight without substantially affecting the effectiveness of the reagents. Once prepared, the fluoride anion-containing solution is contacted with the fluoride receptor reagent.

B.1. Detection by Visible Colorimetric Response

The most pronounced effect exhibited by the fluoride receptor reagents in the presence of F$^-$ ion is a visible colorimetric response. In particular, a dramatic color change from colorless or very light yellow, to dark yellow, and finally to deep purple coloration has been observed.

When no F$^-$ ions are present, the fluoride receptor reagents of the present invention are either colorless or very light yellow. In the presence of about 3 molar equivalents of F$^-$, a dramatic color change occurs from yellow to dark yellow. Moreover, a level of approximately 30 equivalents of F$^-$ has been observed to cause purple coloration.

The intensity of the color change is directly proportional to the amount of F$^-$ ion present in the detection medium. This visible colorimetric change may be characterized in greater detail through the use of ultraviolet/visible light spectroscopy techniques, which are described below.

B.2. Detection by Ultraviolet/Visible Light Spectroscopy

The anion-π interaction between fluoride anion and the receptor reagent compounds can also be detected through the use of ultraviolet/visible light spectroscopy (UV/Vis). In accordance with the visible colorimetric response described above, UV/Vis shows similar two-step spectroscopic changes with increasing F$^-$ concentration. Detailed experimental results and analysis of UV/Vis data are provided in Example 4.

Briefly, the fluoride receptor reagents of the present invention display characteristic NDI absorption peaks at 343, 361, and 381 nm. Titration of the reagents with a fluoride-containing solution gradually bleached the original NDI absorption peaks and concurrently produced new peaks at 475, 605, 711, and 791 nm, corresponding with a visible orange color at approximately 5 molar equivalents of fluoride. These solutions display a clear isosbestic point at 394 nm. It is believed that these absorption peaks are caused by the presence of a NDI.$^-$ radical anion, produced by the charge transfer process as a result of the anion-π interaction.

Further titration of the receptor reagent solutions with F$^-$ anion caused the NDI.$^-$ absorption peaks to gradually disappear, concomitantly with the emergence of a new, broad absorption band at 542 nm. This corresponded with a visual color change from orange to pink at approximately 30 molar equivalents of fluoride. This is believed to correspond with the presence of electrochemically reduced NDI$^{2-}$ dianion, which occurs in the presence of excess F$^-$.

B.3. Detection by Fluorescence Spectroscopy

The anion-π interaction between fluoride anion and the receptor reagent compounds can also be detected through the use of fluorescence spectroscopy. This technique is complementary to the UV/Vis spectroscopy techniques described above; absorption spectroscopy measures transitions of electrons from the ground state to the excited state, while fluorescence deals with transitions of electrons from the excited state to the ground state.

The emissions spectra of the fluoride receptor reagents is observed to change significantly in the presence of fluoride. Specifically, as provided in more detail in Example 12, titration of a receptor reagent solution with 30 nM solution of F$^-$, probed by 381 nm excitation, displayed up to 4.5-fold amplification of original 430 nm fluorescence peak of the NDI unit, and further demonstrated up to 20-fold amplification of a new peak at 465 nm.

With respect to both fluorescence and UV/Vis spectroscopy, it is important to note that the type and magnitude of the observed emissions spectra are not affected by the presence of other anions in the solution. Indeed, as detailed in Examples 4 and 12, no noticeable changes in color or emmission spectra were observed when the titration solution instead contained Cl$^-$, Br$^-$ and/or I$^-$ anions, even at high concentrations up to 30 molar equivalents. These results confirm that the fluoride receptor reagents of the present invention exhibit excellent selectivity for F$^-$ over other halide ions.

B.4. Detection by Nuclear Magnetic Resonance

Nuclear magnetic resonance is an extremely powerful experimental technique, and has been used to observe the formation of the NDI/F$^-$ complex and associated charge transfer interaction.

Experiments conducted using $^1$H NMR are extensively discussed in Examples 5, 6, and 8. Similarly, experimental results of $^{19}$F NMR are disclosed in Example 9. Other active nuclei, particularly $^{13}$C, can also be used.

As detailed in the corresponding Examples, NMR experiments showed significant spectrographic changes during titration of the receptor reagents with a fluoride anion-containing solution. In contrast, no significant spectral changes were observed upon the addition of solutions containing Cl$^-$, Br$^-$ and/or I$^-$ in the absence of F$^-$.

B.5. Detection by Electron Paramagnetic Resonance

Electron paramagnetic resonance (EPR) spectroscopy is a technique for studying chemical species that have one or more unpaired electrons, particularly organic and/or inorganic free radicals. The basic physical concepts of EPR are analogous to those of nuclear magnetic resonance (NMR); the distinction is that EPR provides a measure of the spin of excited electrons, while NMR measures the spin of atomic nuclei.

Detailed results and EPR experimental data are disclosed in Example 14. Briefly, for a solution comprising a fluoride receptor reagent in the presence of 1 molar equivalent of $F^-$ ion, the EPR spectrum showed the characteristic signals of delocalized $NDI.^-$ radical anion (g=2.0030) with hyperfine structures. In contrast, a solution comprising a receptor reagent in the absence of $F^-$ ion did not show any characteristic EPR signals.

Perhaps surprisingly, a solution comprising a receptor reagent in the presence of large excess of $F^-$ ion also failed to show the characteristic EPR signals for the $NDI.^-$ radical. This is believed to be a result of the formation of $NDI^{2-}$ dianions in the presence of excess fluoride. Accordingly, EPR can be used to determine the precise level of $NDI.^-$ anion formation, and therefore can be used to determine the precise molar ratio of fluoride to receptor reagent present in a test solution.

B.6. Detection by Spectroelectrochemistry

Spectroelectrochemistry (SEC) combines the techniques of electrochemistry and spectroscopy. Generally, a compound is oxidized or reduced within a specially designed electrochemical cell. The kinetics and products of the reaction are simultaneously monitored using spectroscopic techniques. Detailed experimental results using this technique are provided in Example 13.

B.7. Detection by Electrospray Ionization Mass Spectrometry

Electrospray Ionization Mass Spectrometry (ESI-MS) is an experimental technique that creates ionized particles for detection using mass spectrometry. As expected based on results obtained using other experimental techniques, ESI-MS testing of reagents in the presence of a large excess of F-ion showed the presence of $NDI^{2-}$ dianions, but did not indicate the presence of any neutral NDI or $NDI.^-$ complexes.

Detailed experimental results using ESI-MS are provided in Example 10.

B.8. Detection by Isothermal Titration Calorimetry

With respect to the fluoride receptor reagents of the present invention, it has been discovered that isothermal titration calorimetry (ITC) presents a characteristic pattern for the fluoride receptor reagents in the presence of $F^-$ ion. This pattern is clearly distinguishable from other anions, including halide anions such as $Cl^-$, $Br^-$, and $I^-$. As a result, the characteristic ITC pattern can be used to detect $F^-$ even in the presence of a large excess of other halide anions.

The experimental results provided in Example 11 confirm that the fluoride receptor reagents bind $F^-$ much more strongly than other halide ions. Unlike other experimental methods, however, the weak interactions between the receptor reagents and other halide anions are detectable using ITC. Accordingly, using these characteristic ITC patterns, one could determine whether a given test solution contains $F^-$ only or, alternatively, whether the test solution contains is a mixture of $F^-$ with another halide anion.

C. Selectivity

The fluoride receptor reagents of the present invention exhibit good sensitivity to $F^-$ anions. Preferred fluoride receptor reagents, which comprise compounds in which two NDI units overlap with each other, exhibit sensitivity to $F^-$ concentrations as low as the nM range. On the other hand, the reagents demonstrate virtually no affinity for other anions, including other halide anions such as $Cl^-$, $Br^-$ and $I^-$.

In general, it is believed that the size of the anion and the Lewis acidic cavity size of the preferred fluoride receptor reagents work in tandem to determine binding selectivity. Without being bound to any particular theory, it is believed that $Cl^-$, $Br^-$, $I^-$, and other anions are too large to fit between the two aromatic π-π stacking units and in the "pocket," or interior portion, of the preferred receptor reagent compounds. In contrast, the smaller $F^-$ ions fit well between the two NDI moieties through anion-π interaction, and are further complexed within the Lewis acid cavity through NH . . . F— hydrogen bonding.

As described above, UV/Visible light spectroscopy, fluorescence spectroscopy, and NMR spectroscopy experiments indicate that the fluoride receptor reagents show high selectivity for $F^-$ as compared to other anions, such as $Cl^-$, $Br^-$, $I^-$, $NO_2^-$, $NO_3^-$, $N_3^-$, $PF_6^-$, acetate anion ($AcO^-$), and $H_2PO_4^-$. (See FIGS. 5c and 13).

For instance, Example 4c was conducted to investigate the selectivity and sensitivity of the fluoride receptor reagents with respect to $F^-$. A solution comprising reagent SR was titrated with $F^-$ in the presence of 30 molar equivalents of $Cl^-$. The results of the titration are shown in FIG. 4(e). Although reagent SR showed no optical response to the presence $Cl^-$ alone, it showed the characteristic two-step color change associated with $F^-$ even in the presence of $Cl^-$, demonstrating the desired selectivity for the $F^-$ ion.

Additionally, in Example 12, the effects of preorganization on the sensitivity of NDI receptors were probed by monitoring the $F^-$-induced fluorescence changes at the minimum receptor concentrations. The titration of reagent SR (1 nM in DMSO) with $F^-$ (30 nM), probed by 381 nm excitation, displayed a 4.5-fold amplification of the original 430 nm emission peak of the NDI unit and a 20-fold amplification of a new peak at 465 nm, as shown in FIG. 4(f). Reagent N1 (10 μM in DMSO) showed a similar fluorescence profile and 5.5-fold increase of the 465 nm emission peak (FIG. 4(f)), albeit at $10^4$ times higher concentrations than SR. The excellent nM sensitivity of SR vs. weaker μM sensitivity of N1 demonstrates that preorganization of two NDI units improves the $F^-$ affinity and sensitivity of the receptor reagents through stronger $NDI/F^-$ interactions.

D. Regeneration and Re-Use of the Fluoride Receptor Reagents

It has also been discovered that the complexation of fluoride anion with the receptor reagents of the present invention is a fully reversible process. The process can be reversed using a number of independent techniques.

For example, the colored fluoride-NDI complexes of the present invention are stable in most aprotic solvents. In contrast, the addition of a polar protic solvent (e.g., $H_2O$ or $CH_3OH$) results in disassociation of the fluoride anion, resulting in a reverse color change.

The complexation process can also be reversed through the use of an oxidizing agent (e.g., $NOBF_4$). It has been observed that the orange and pink solutions of the present invention become colorless after the addition of $NOBF_4$. Without being bound to any particular theory, NMR titration analysis indicates that $NOBF_4$ oxidizes the orange $NDI^-$ radical anion and pink $NDI^{2-}$ dianion to colorless NDI. (See generally Example 6).

Additionally, the process can be reversed by electrochemically regenerating the NDI units from the $NDI^-$ radical anion and $NDI^{2-}$ dianion, respectively.

After the color change has been reversed, further addition of F⁻ to the solution will cause the characteristic color changes to reappear (e.g., the solution will again become orange at relatively low F⁻ concentrations, and pink at higher F⁻ concentrations). This process can be repeated multiple times, as desired.

Following reversal of the color change, the fluoride receptor reagents may be optionally recovered from the mixture. In general, the fluoride receptor reagents can be recovered by evaporating the solution and rinsing the resulting precipitate thoroughly with water. A more purified reagent-containing precipitate can be obtained through the use of high performance liquid chromatography (HPLC). Similar techniques are used in the process for preparation of the fluoride receptor reagents, which is provided in more detail in Example 1.

Moreover, chemical (e.g., $NOBF_4$) and electrochemical methods can be used to regenerate the fluoride receptor reagents after NDI/F⁻ interaction, and these methods can accordingly be exploited to develop reusable commercial fluoride sensor devices.

Having described the invention in detail, it will be apparent that modifications and variations are possible without departing from the scope of the invention defined in the appended claims.

EXAMPLES

The following non-limiting examples are provided to further illustrate the present invention.

General Methods and Materials

Unless otherwise indicated, the following equipment was utilized in each of the following working examples, as appropriate.

Analytical thin layer chromatography (TLC) was performed on silica gel 60-F254 (MERCK) plates and detected under UV lamp and/or by developing with $I_2$. Column chromatography was performed on silica gel 60 (SORBTECH). $^1H$, $^{13}C$, and $^{19}F$ NMR spectra were recorded at 298 K in appropriate deuterated solvents using BRUKER AVANCE 400 MHz and BRUKER AVANCE 600 MHz spectrometers. High-Resolution Electrospray Ionization mass spectra (ESI-MS) were recorded on a JEOL ACCUTOF JMS-T100LC ESI mass spectrometer. FT-IR spectra were collected on a PERKINELMER PRECISELY SPECTRUM 100 FT-IR Spectrometer.

In some of the following examples, a control compound with the following structure was used:

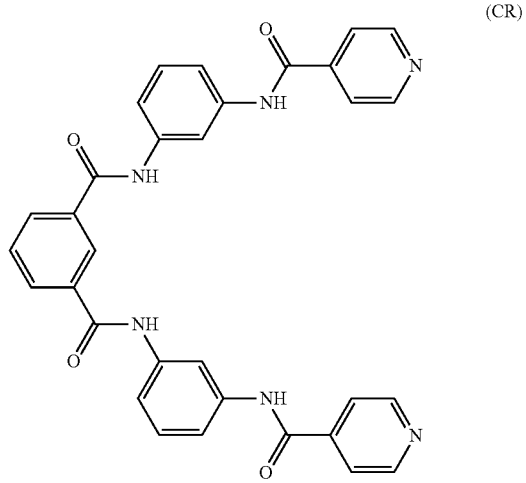 [SMILES: O=C(Nc1cccc(NC(=O)c2cccc(C(=O)Nc3cccc(NC(=O)c4ccncc4)c3)c2)c1)c1ccncc1]

(CR)

This compound is sometimes hereinafter referred to as "reagent CR", or simply as "CR". Reagent CR is similar to the fluoride receptor reagents of the present invention, but lacks any NDI functional groups.

Standard Process for Titration Examples

Unless otherwise indicated, the following procedure was used for all examples involving titration experiments. Generally, titrant solutions comprising the fluoride receptor reagents (e.g., reagents N1, SR, and LR) were maintained at a concentration of 10 μm. Titrand solutions containing fluoride anion were 30 times more concentrated (e.g., 300 μm) to minimize dilution effects during titration. Unless otherwise indicated, the solvent for all solutions was dimethyl sulfoxide (DMSO).

Example 1

Preparation of Fluoride Receptor Reagents

Starting materials and reagents were purchased from Sigma Aldrich and used as received. Pyridine-2,6-dicarbonyl dichloride and mono-(tert-butoxycarbonyl) protected m-phenylenediamine intermediate 4 were prepared using methods described in the literature and well known to practitioners skilled in the art. All reactions were performed under $N_2$ atmosphere using dry solvents unless otherwise specified.

Figure 1:
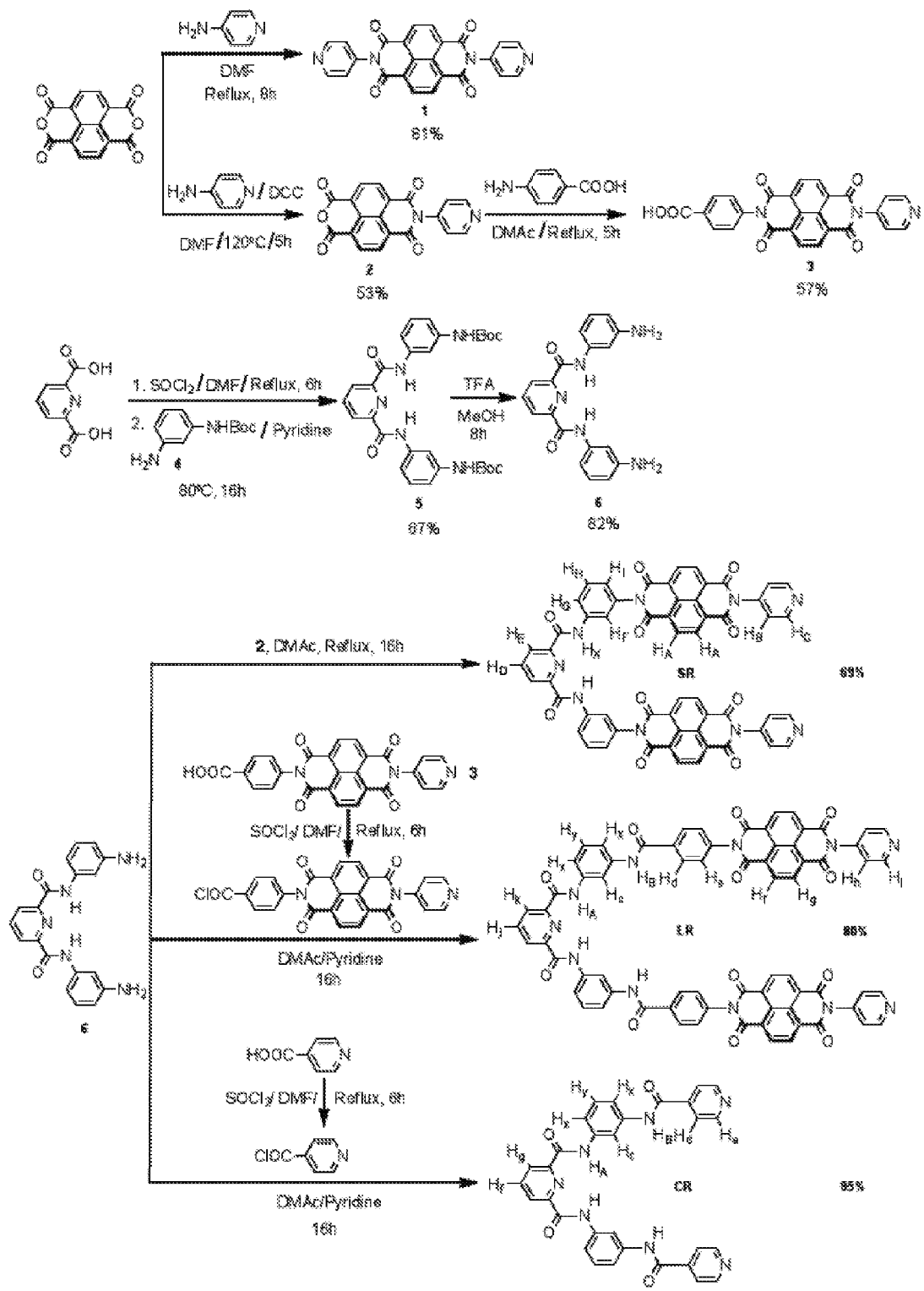
FIG. 1 is a schematic representation of the syntheses of fluoride receptor reagents N1, SR, and LR, and of control reagent CR.

A detailed schematic representation of the following process is illustrated in FIG. 1.

Reagent N1:

Naphthalenediimide (NDI) reagent N1 was prepared using methods described in the literature and well known to practitioners skilled in the art. Briefly, a mixture of 1,4,5,8-naphthalene tetracarboxylic dianhydride (NTDA) (0.8 g, 3 mmol) and 4-amino pyridine (0.56 g, 6 mmol) in dimethylformamide (DMF) (20 mL) was heated under reflux for 8 h. A crystalline solid precipitated on cooling and was collected by filtration. The crude product was purified by recrystallization from DMF to obtain compound N1 as an off-white crystalline solid in 81% yield (1.02 g, 2.43 mmol).

Intermediate 2:

A solution of NTDA (5.36 g, 20 mmol), 4-aminopyridine (1.2 g, 12.8 mmol) and dicyclohexylcarbodiimide (2.64 g, 12.8 mmol) in DMF (80 mL) was heated under reflux for 5 h. Upon cooling the reaction mixture to 25° C. dicyclohexylurea precipitated out, which was discarded by filtration. To the filtrate 2N HCl (200 mL) was added. The resulting yellow precipitate was filtered and washed thoroughly with $H_2O$ until the filtrate became neutral. The crude product was purified by column chromatography (SiO2, 9:1 $CH_2Cl_2/CH_3OH$) to obtain intermediate compound 2 as a pale yellow solid in 53% yield (3.65 g, 10.6 mmol).

Intermediate 3:

A mixture of intermediate compound 2 (1.17 g, 3.4 mmol) and p-amino benzoic acid (0.49 g, 3.6 mmol) in DMAc (36 mL) was heated under reflux for 5 h. H2O (40 mL) was added to the reaction mixture and stored in a refrigerator overnight. The resulting precipitate was filtered and washed with hot methanol and hot ethyl acetate to obtain intermediate compound 3 as a pale yellow solid in 57% yield (0.90 g, 1.94 mmol).

Intermediate 4:

One amine group of m-phenylenediamine (0.50 g, 4.62 mmol) was protected as NH(tert-butoxycarbonyl), following procedures described in the literature and well known to practitioners skilled in the art. See Suda, Y. et al., 17 *Bioconjugate Chem.* 1125, 1125-1135 (2006). This procedure obtained intermediate compound 4 as a white solid in 70% yield (0.67 g, 3.23 mmol).

Intermediate 5:

Pyridine-2,6-dicarboxylic acid (0.64 g, 3.83 mmol) was treated with $SOCl_2$ (10 mL) and catalytic DMF under refluxing condition for 6 h. Solvents were evaporated under vacuum. To completely remove all reagents, dry toluene was added to the resulting pale yellow solid and evaporated under vacuum. Pyridine-2,6-dicarboyl dichloride was obtained as a pale yellow solid in near quantitative yield (0.78 g, 3.83 mol).

A solution of pyridine-2,6-dicarbonyl dichloride (0.78 g, 3.83 mmol) in tetrahydrofuran (2 mL) was added dropwise to a solution of intermediate compound 4 (2 g, 9.57 mmol) in pyridine (40 mL). The reaction mixture was heated under reflux for 16 h. After cooling the reaction mixture to 25° C. ethyl acetate (100 ml) was added and extracted with $H_2O$ then brine solution. The combined organic layer was dried over anhydrous $Na_2SO_4$ and evaporated under vacuum to obtain intermediate compound 5 as white solid in 67% yield (1.4 g, 2.57 mmol).

Intermediate 6:

To a solution of intermediate compound 5 (1.1 g, 2 mmol) in methanol (5 mL) trifluoroacetic acid (20 mL) was added and the reaction mixture was stirred at 25° C. for 8 h. After removing solvents $H_2O$ was added to the solid and pH was adjusted to 8 with 30% aqueous $NH_3$ solution. The aqueous layer was then extracted with ethyl acetate. The ethyl acetate layer was collected and dried over anhydrous $Na_2SO_4$. Solvent was evaporated under vacuum to obtain diamine intermediate 6 as a white solid in 82% yield (0.57 g, 1.64 mmol).

Reagent SR:

A mixture of intermediate compound 2 (1.17 g, 3.4 mmol) and intermediate compound 6 (0.59 g, 1.7 mmol) in dimethyl acetate (DMAc) (12 mL) was heated under reflux for 16 h. After cooling the reaction mixture to 25° C., $H_2O$ (40 mL) was added and the solution was placed in a refrigerator overnight. Filtration and washing of the resulting precipitate with cold methanol afforded reagent SR as an off-white solid in 69% yield (1.17 g, 1.17 mmol).

Reagent LR:

Carboxylic acid 3 (1.62 g, 3.5 mmol) was treated with $SOCl_2$ (20 mL) and catalytic amount of DMF under refluxing conditions for 6 h. Removal of solvents under vacuum afforded the corresponding acid chloride (1.64 g, 3.4 mmol), which was used for amide coupling reaction with intermediate compound 6. A mixture of the acid chloride of intermediate compound 3 (1.64 g, 3.4 mmol), intermediate compound 6 (0.59 g, 1.7 mmol) and pyridine (3 mL) in DMAc (12 mL) was heated under reflux for 16 h. After cooling the reaction mixture to 25° C., $H_2O$ (40 mL) was added and the solution was placed in a refrigerator overnight. The resulting precipitate was filtered and washed with cold methanol to obtain reagent LR as beige solid in 80% yield (1.68 g, 1.36 mmol).

Reagent CR:

Pyridine-4-carboxylic acid (0.90 g, 7.3 mmol) was treated with $SOCl_2$ (20 mL) and catalytic amount of DMF under refluxing conditions for 6 h. Removal of solvents under vacuum afforded the corresponding acid chloride (1.03 g, 7.28 mmol), which was used for amide coupling reaction with intermediate compound 6. A mixture of intermediate compound 6 (1.18 g, 3.40 mmol), pyridine-4-carbonyl chloride (1.03 g, 7.28 mmol) and pyridine (3 mL) in DMAc (12 mL) was heated under reflux for 16 h. $H_2O$ (40 mL) was added to the reaction mixture and the solution was placed in a refrigerator overnight. The resulting precipitate was filtered and washed with cold water. The crude material was purified by column chromatography (SiO2, 8:1 $CH_2Cl_2/CH_3OH$) to obtain reagent CR as an off white solid in 85% yield (1.61 g, 2.89 mmol).

Example 2

Calculation of the Energy Minimized Structures of NDI/Fluoride Complex, SR and LR B3LYP/6-31+G** energy minimization and Natural Bond Orbital (NBO) calculations were conducted using Gaussian 03 Software. These calculations were conducted to determine the shape of the [napthalenediimide.fluoride] complex, as well as the shape of fluoride reagent receptors SR and LR.

Figure 2:
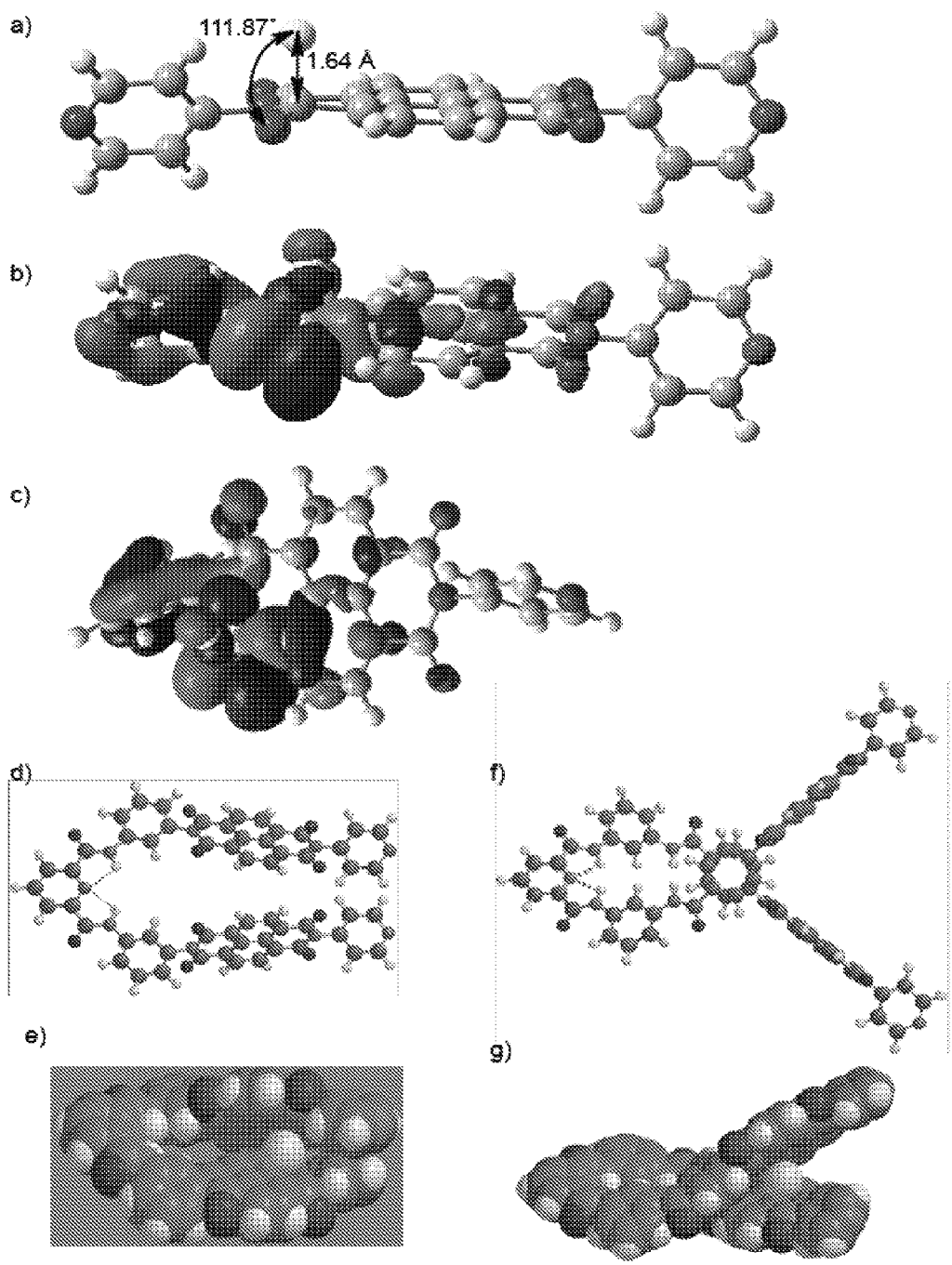
FIG. 2 is a schematic representation of the energy minimized structures of reagents N1, SR, and LR, obtained using the procedure described in Example 2. More particularly, panel (a) depicts a model of an energy minimized structure of the [N1.F$^-$] complex. Panels (b) and (c) provide a side view and a top view, respectively, of that structure. Similarly, panel (d) depicts a model of an energy minimized structure for species SR, panel (e) depicts the [SR.F$^-$] complex, panel (f) depits species LR, and panel (g) depicts the [LR.F$^-$] complex.

The results of these calculations are generally disclosed in FIG. 2. Panel (a) represents the B3LYP/6-31+G** energy minimized structure of the [N1.F$^-$] complex, showing the interaction between lone-pair electrons of F$^-$ in its 2p orbital and the π*-orbitals of NDI; panels (b) and (c) show side and top views of N1, respectively. Energy minimized structures of SR, [SR.F$^-$], LR, and [LR.F$^-$] are shown in panels (d), (e), (f), and (g), respectively. The models were obtained from semi-empirical AM1 Global followed by Hartree-Fock 3-21G Global energy minimization using SPARTAN 2008 software.

B3LYP/6-31+G** energy minimization of the [NDI.F$^-$] complex shows that F— is preferentially located on top of an imide ring carrying two electron withdrawing C=O bonds. It is notable, however, that no covalent C—F bond is formed. The calculated energy of the NDI/F— interaction in the gas phase is approximately 45 kcal/mol, which is stronger than F—H . . . F$^-$ H-bonding (ca. 40 kcal/mol) but weaker than a covalent C—F bond (ca. 110 kcal/mol). The closest distance from F$^-$ ion to NDI involves the carbonyl C (1.64 Å) in the imide ring. The O=C . . . F angle was calculated to be 111.87°. For comparison, a typical C—F covalent bond length is much shorter at 1.30-1.34 Å. NBO calculations also show that there is Δq=0.27 electron transfer from the F$^-$ lone pair located in its 2p orbital to π*-orbitals of NDI, leaving 0.73 electrons on the F$^-$ ion in a NDI.F$^-$ complex.

Semi-empirical AM1 Global calculations were also conducted for reagents SR and LR. Hartree-Fock 3-21G Global energy minimization, conducted using SPARTAN 2008 software, indicates that both receptors have a folded configuration. See FIG. 2, panels (d)-(g).

As shown in the figures, it is believed that intramolecular bifurcated hydrogen bonds between the central pyridine N atom and the two adjacent amide protons serve to bring the two ends of each molecules into close proximity. While the short bisamide linker in reagent SR brings the two NDI units into a perfectly overlapping parallel orientation, the longer tetraamide linker in reagent LR projects the two NDI units at an angle. These structural differences explain the greater selectivity and sensitivity of reagent SR for F$^-$ ion, versus reagent N1, as observed from UV/Visible spectroscopy and fluorescence experiments.

Example 3

Visual Color Changes During F$^-$ Titration of Fluoride Receptor Reagents

Several experiments were conducted to observe the visible color changes that occur when NDI-based receptor reagents N1, SR, and LR were titrated with solutions containing F$^-$ ions. Titrations were carried out using F$^-$ in a number of solvents, including aqueous dimethyl sulfoxide (DMSO), dimethylformamide (DMF), dimethylacetamide (DMAc), acetonitrile, acetone, and tetrahydrofuran, with each solution containing up to 15% of $H_2O$. Otherwise, the titrations followed the standard titration procedure outlined above.

For each of reagents N1, SR, and LR, the titrated solution immediately changed color in a distinct two-step pattern, shown in more detail in FIG. 13. Generally, the colorless NDI solutions turned orange at lower $F^-$ equiv. ($\leq 5$ equiv), and then turned pink at higher $F^-$ equiv. (>5 equiv).

In contrast, titrations with $Cl^-$, $Br^-$, $I^-$, $NO_2^-$, $NO_3^-$, $N_3^-$, acetate anion ($CH_3$—C(=O)—$O^-$), and $H_2PO_4^-$ did not affect the initially colorless solutions of the tested NDI-based receptor reagents, even at concentrations up to 30 equiv. This result confirms the selectivity of the tested NDI-based receptor reagents for the fluoride anion.

Titrations were also conducted using the NDI-free CR compound as a receptor reagent. Because this compound does not possess any NDI units, it serves as a useful control against which to compare the other fluoride receptor reagents. In accordance with the titration procedure applied to the other reagents above, the CR reagent did not change color in response to any anion.

Example 4

UV/Visible Light Spectroscopy

UV/Visible spectroscopy experiments were conducted to quantify $F^-$-induced colorimetric transitions of NDI receptors with respect to various reagents. Fluoride reagent receptors N1, SR, and LR display characteristic NDI absorption peaks at 343, 361, and 381 nm.

As indicated above, UV/Visible light (UV/Vis) spectra were recorded on a PerkinElmer Lambda-25 UV/Vis spectrophotometer. For each experiment, receptor N1, SR, and CR concentrations were maintained at 10 μM. Titration of the $F^-$ ion was conducted using the standard titration procedure outlined above.

A. Reagent N1

Titration of reagent N1 with 0-5 molar equivalents of $F^-$ ion gradually bleached NDI absorption peaks and concurrently produced new peaks at 475, 605, 711, and 791 nm, establishing a clear isosbestic point at 394 nm, as the solution turned orange.

Figure 3:
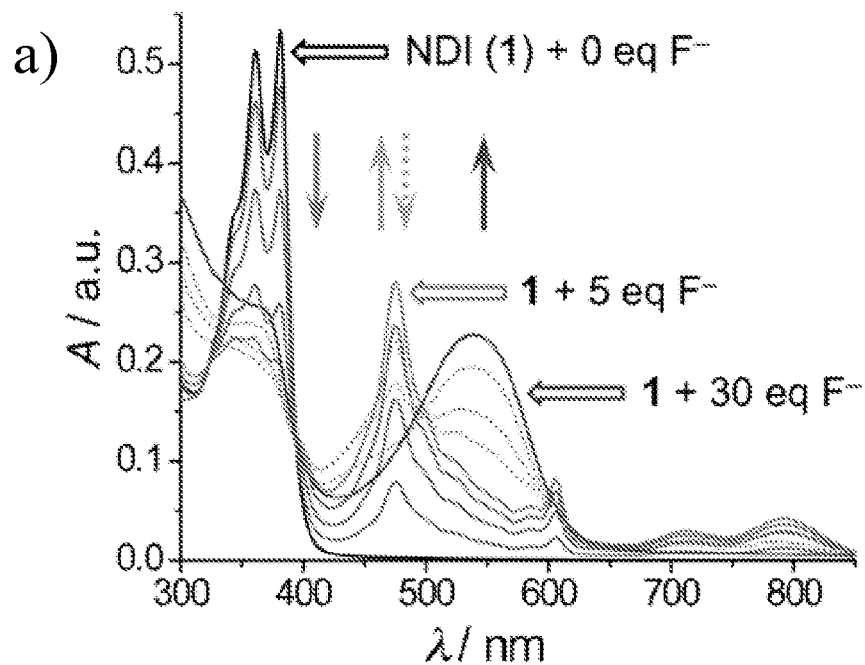
FIG. 3 is a representation of the UV/Visible light spectroscopy data obtained using the procedure set forth in Example 4 for reagent N1. Panel (a) discloses the spectroscopy data obtained upon exposure of N1 to F$^-$ anion, while panel (b) discloses the spectroscopy data obtained from electrochemical reduction of reagent N1 at −450 mV vs. Ag/AgCl in DMF.
Figure 3:
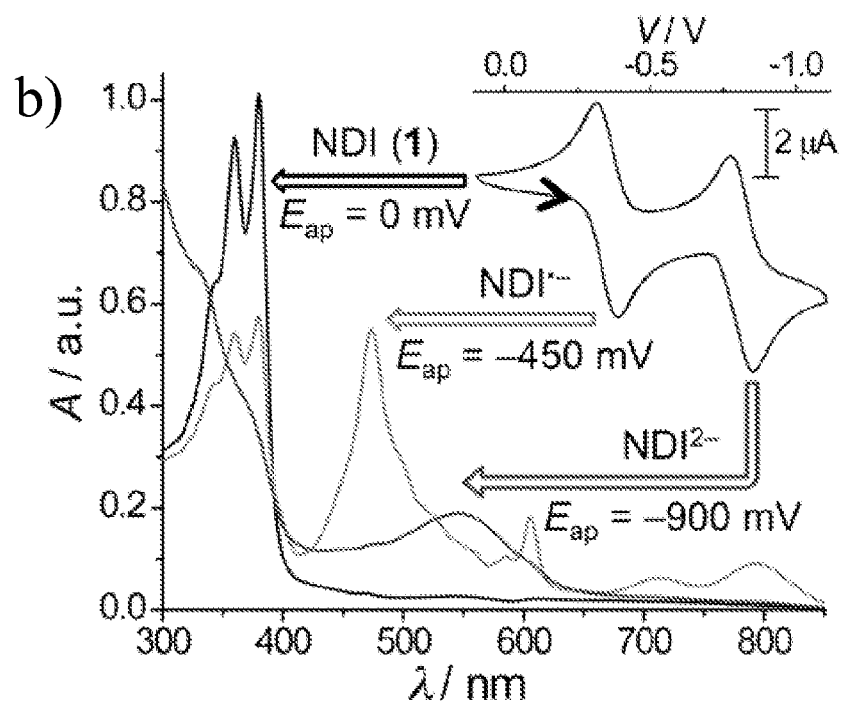

As shown in FIG. 3, panel (c), the absorption spectrum of orange species generated by $F^-$ matches exactly with that of a $NDI.^-$ radical anion produced in the absence of $F^-$ by electrochemical reduction of reagent N1 at –450 mV vs. Ag/AgCl in DMF, shown in panel (d). The inset of FIG. 3, shown to the upper left of panel (d), shows a cyclic voltammogram of N1 (vs. Ag/AgCl in 0.1 M $TBAPF_6$/DMF) in the absence of $F^-$.

Manifestations of identical spectroscopic changes with the same isosbestic point (394 nm) during $F^-$ titration (FIG. 3(c)) and during spectroelectrochemistry of reagent N1 in the absence of $F^-$ strongly suggest that a $F^- \rightarrow NDI$ ET event takes place in $NDI/F^-$ complex. (See Example 13.) Nucleophilic attack of $F^-$ on NDI forming a covalent C—F bond is believed to produce spectroscopic transitions different from spectroelectrochemistry. The EPR spectrum of $F^-$-induced orange solution of reagent N1 further confirms the formation of a delocalized $NDI.^-$ radical anion (g=2.0030). (See Example 14.)

As illustrated in FIG. 14, these results indicate that at first $F^-$ binds with NDI through anion-π and CT interactions that facilitate $F^- \rightarrow NDI$ electron transfer and generate $NDI.^-$.

As the solution of reagent N1 turned from orange to pink, which occurred as the titration progressed from about 5 to about 30 molar equivalents of $F^-$ ion, the $NDI.^-$ absorption peaks gradually disappeared concomitantly with the emergence of a broad absorption band at 542 nm. This transition at higher $F^-$ equiv. can be attributed to one of the following possibilities: a) $NDI.^-$ is further reduced to $NDI^{2-}$ dianion by another $F^-$ ($E_{1/2}$=–2.87 V) or b) $NDI.^-$ is attacked by $F^-$ ion forming a C—F bond, which would be an extremely high-energy process.

Strong similarities between absorption spectra of pink solution of reagent N1 produced by excess $F^-$ (FIG. 3(c)) and electrochemically generated $NDI^{2-}$ at –900 mV versus Ag/AgCl and DMF in the absence of $F^-$ (FIG. 3(d)) strongly support the first scenario. Higher relative intensity of 542 nm band of a quickly generated $F^-$ ion-induced pink solution than that of a slowly (diffusion controlled) electrochemically reduced $NDI^{2-}$ dianion may be attributed to a possible degradation of NDI unit during prolonged reductions. Consistent with the formation of $NDI^{2-}$ by excess $F^-$, the pink solution of reagent N1 became EPR silent (see Example 14, FIG. 10) and its ESI-MS revealed $[N1]^{2-}$ at m/z 210.40, but no signal corresponding to any $[N1/F^-]^{n-}$ species was found at this stage (see Example 10, FIG. 9A). Oxidation of orange ($N1.^-$) and pink ($N1^{2-}$) solutions with $NOBF_4$ decolorized them. Because of strong absorptions of $NOBF_4$ in 350-400 nm regions, regeneration of N1 could not be confirmed by UV/Vis spectroscopy. However, $^1H$ NMR spectroscopy confirmed complete recovery of N1 after $NOBF_4$ oxidation (see generally Example 4).

Spectroscopic changes shown by N1 during $F^-$ titration (FIG. 3(c)) and spectroelectrochemistry studies without $F^-$ (see Example 13) support the chain of events described in Scheme 1a: A strong $NDI/F^-$ interaction leading to $F^- \rightarrow NDI$ ET generates $NDI.^-$, which is further reduced to $NDI^{2-}$ by another $F^-$ ion. It is conceivable that $F^- \rightarrow NDI$ ET process in $NDI/F^-$ complexes that forms $NDI.^-$ and $NDI^{2-}$ may in turn produce an unstable transient F. radical. Whether it ultimately reacts with solvent molecules, counter ions, or homo-couple to emanate $F_2$ gas remains unclear after careful analyses of $NDI/F^-$ mixtures.

B. Reagents SR and LR

Figure 5:
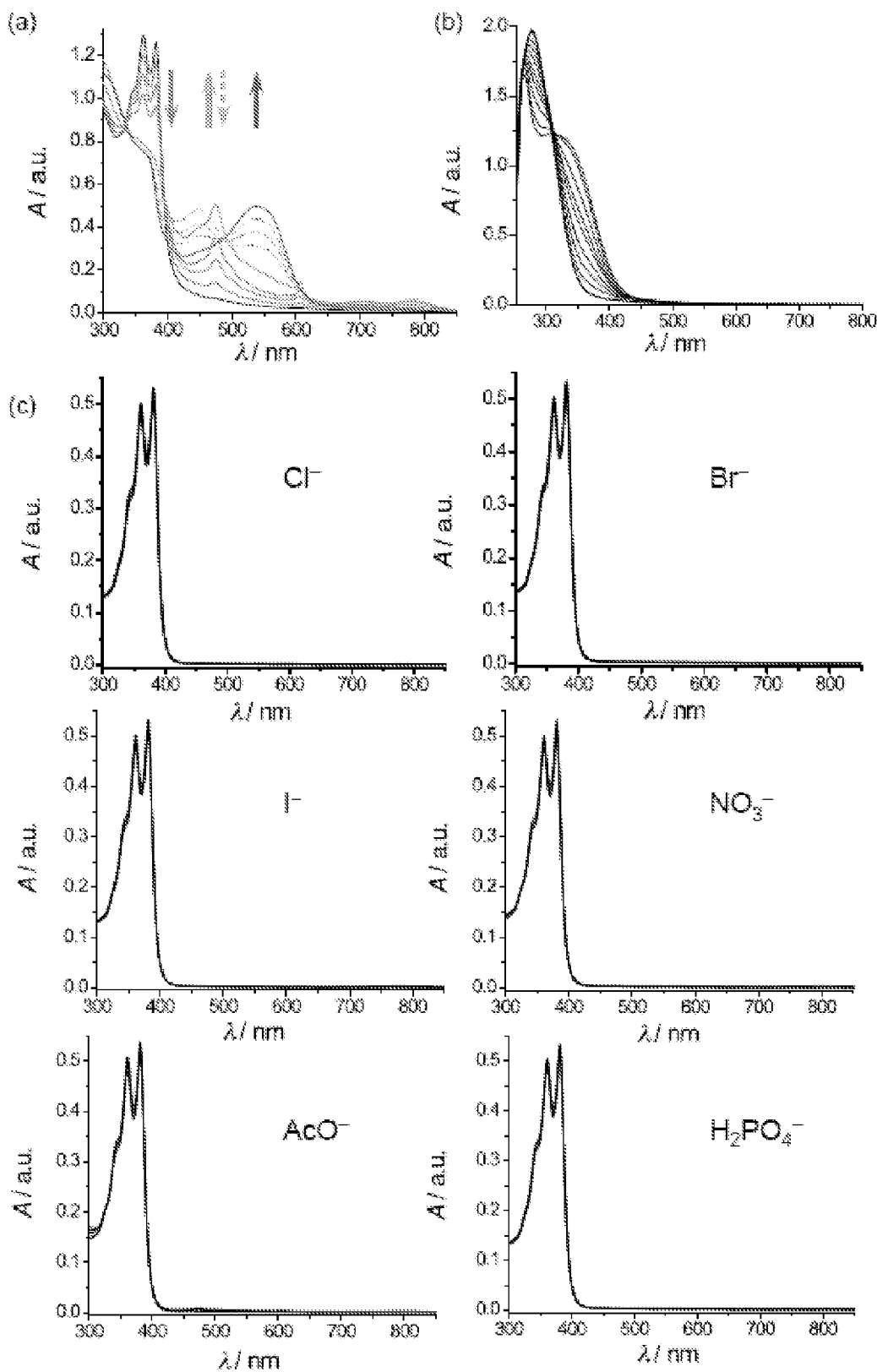
FIG. 5 is a representation of the UV/Visible light spectroscopy data obtained using the procedure set forth in Example 4 for reagents SR, CR, and N1, shown in panels (a), (b), and (c), respectively.

Following the same experimental procedure outlined above, preorganized NDI receptor reagents SR and LR displayed similar two-step spectroscopic changes with $F^-$. Characteristic results for reagent SR are shown in FIG. 5, panel (a).

In addition to binding a $F^-$ ion between two terminal NDI units, thereby forming $NDI/F^-/NDI$ sandwich complex, receptors SR and LR can potentially bind a second $F^-$ ion in the amide cavities via H-bonding interaction (FIG. 14). This interaction, however, did not produce an additional optical signal that was detectable during this experiment.

For comparison, a solution comprising control receptor CR, which does not comprise any NDI moieties, was titrated with fluoride anion. As shown in FIG. 5, panel (b), there was virtually no colorimetric response caused by increasing fluoride concentration.

C. Titrations with Other Halides

To investigate the selectivity and sensitivity of the fluoride receptor reagents with respect to $F^-$, reagent SR was titrated with $F^-$ in the presence of 30 molar equivalents of $Cl^-$. The results of this titration are shown in FIG. 4(e). Although reagent SR showed no optical response to the presence $Cl^-$ alone, it showed the characteristic two-step color change associated with $F^-$ even in the presence of $Cl^-$, demonstrating the desired selectivity for the $F^-$ ion.

Similarly, FIG. 5, panel (c) is a representation of the data obtained when receptor reagent N1 was titrated with various other halides, including $Cl^-$, $Br^-$, $I^-$, $NO_3^-$, acetate anion ($AcO^-$), and $H_2PO_4^-$. As with reagent SR, above, reagent N1 did not show any optical response to the presence of anions other than $F^-$.

Example 5

Solution-State $^1$H Nuclear Magnetic Resonance Study

In order to more fully examine the solution state conformation of reagent LS, various 1D and 2D NMR spectroscopy (COSY) experiments were performed.

The 400 MHz $^1$H NMR spectra in DMSO-d6 is extremely well resolved, with sharp resonances. The 400 MHz $^1$HNMR spectra, which discloses the presence of only a single set of resonances for the m-phenylenediamine, p-aminobenzoic acid, 4-amino pyridine and naphthalene diimide residues in polar aprotic solvent (dimethyl sulfoxide, DMSO-d6), suggests that reagent LS is highly symmetric in nature. These results further support the conclusion reached by the calculations conducted in Example 2, above.

The temperature dependence of the amide protons of reagent LS was studied in DMSO-d6 over the temperature range of 293-343 K using a TXI probe. The NH group closest to the pyridine dicarboxamide moiety exhibited relatively low values of temperature coefficients (dδ/dT −3.5 ppb/K), indicating the presence of intramolecularly hydrogen-bonded NH groups (FIG. 16). This observation was also supported by relatively down-field chemical shift (11.2 ppm) values for this NH group, compared to other NH protons (10.5 ppm). However, relatively high temperature coefficients for the amide NH groups of the m-phenylenediamine moiety (dδ/dT −4.5 ppb/K) indicate that there is almost no possibility for the formation of any intramolecular hydrogen bonds with this NH group, and in polar aprotic solvents such as DMSO-d6, it is more accurately interpreted as a solvent-exposed NH group (FIG. 16). Additionally, complete spectral assignments were made using 2D NMR spectroscopy (COSY) (FIG. 17).

$^1$H NMR titration of reagent LS with nBu$_4$NF.3H$_2$O indicates the presence F$^-$ binding. This indicates a two step mechanism: first, π-anion-π interaction takes place at concentrations up to one equivalent of F$^-$, after which the NH . . . F$^-$ hydrogen bonding interaction occurs. Different patterns were observed in the titration range of 0-1 and 1-3 equivalents of F$^-$, respectively (FIG. 18). The peaks corresponding to NDI broaden and disappear after the addition of one equivalent of F$^-$, and no significant change in the δ values corresponding to the NH was been observed.

More than 1 equivalent of F$^-$ causes significant down-field shift of the NH peak, which broadens and almost disappears after addition of three equivalents of F$^-$ ion. This is likely due to the strong hydrogen bonding with F$^-$, and may indicate that some deprotonation takes place.

In contrast, no significant spectral changes were observed upon the addition of Cl$^-$, Br$^-$ and I$^-$. No disappearance of the NH peaks took place in the presence these ions, which are significantly less basic than F$^-$. This is likely due to the fact that, among halide anions, F$^-$ usually forms the strongest hydrogen-bond with an NH group.

Example 6

$^1$H Nuclear Magnetic Resonance Spectroscopy During F$^-$ Titration $^1$H Nuclear Magnetic Resonance (NMR) was conducted during titration of F$^-$ anions into a solution comprising a fluoride receptor reagent. The results of these tests provide better insight into the nature of the NDI/F$^-$ interaction. Titration of the F$^-$ ion was conducted using the standard titration procedure outlined above, with the exception that the fluoride receptor reagents (N1, LR, SR) were maintained at a concentration of 0.4 mM in DMSO solution.

A. Reagent N1

As shown in FIG. 15, panel (a), the $^1$H NMR spectrum of receptor N1 reveals a singlet at 8.75 ppm corresponding to four identical NDI core protons (H$_A$) and two doublets at 7.58 and 8.81 ppm corresponding to H$_B$ and H$_C$ of the pyridine ring, respectively. During the titration of N1 with F$^-$ all signals became broad but none shifted at all, virtually ruling out the possibility of a CH . . . F$^-$ H-bond formation. Consistent with UV/Vis results, only H$_a$ signal gradually disappeared as F$^-$ reached 1 equiv., indicating the formation of NDI.$^-$ radical anion. EPR spectrum of this species (FIG. 10) confirmed the presence of NDI.$^-$ radical anion.

Subsequently, as described more fully in Example 7, NOBF$_4$ oxidation of the N1.$^-$ radical anion completely regenerated N1, and the original NMR spectrum reappeared, showing H$_a$ signal at 8.75 ppm. These results support our hypothesis that NDI/F$^-$ interaction facilitates an F$^-$→NDI electron transfer event that generates NDI.$^-$ radical anion (FIG. 14).

B. Reagent SR

As shown in FIG. 15, panel (b), for reagent SR, NDI core protons (H$_a$) and the bisamide linker (H$_x$) appeared at 8.73 and 11.25 ppm, respectively. During the titration of SR with F$^-$ ion H$_A$ signal gradually disappeared as the F$^-$ ion concentration reached 1 equiv., while H$_X$ signal shifted slightly downfield, indicating that at first F$^-$ binds with NDI units. NDI core protons in SR and LR (see FIG. 7(a)) did not split before disappearing, potentially indicating the formation of NDI/F$^-$/NDI sandwich complexes in which both NDI units interact evenly with F$^-$ ion. Significant downfield shift as well as broadening of H$_X$ signal occurred above 1 equiv. F$^-$ ion, which indicates subsequent NH . . . F$^-$ interaction and possible deprotonation of amide protons. These events suggest that in SR and LR, F$^-$ first binds between NDI units and then a second F$^-$ interacts with amide linkers (FIG. 14). ITC studies confirm stronger NDI/F$^-$ interaction than NH . . . F$^-$ interaction (See Table 1, which indicates that K$_a$(N1/F$^-$)>>K$_a$(CR/F$^-$)). Unexpectedly high F$^-$ affinity of NDI may be attributed to strong orbital and electronic interactions.

C. Reagent LR

Figure 7:
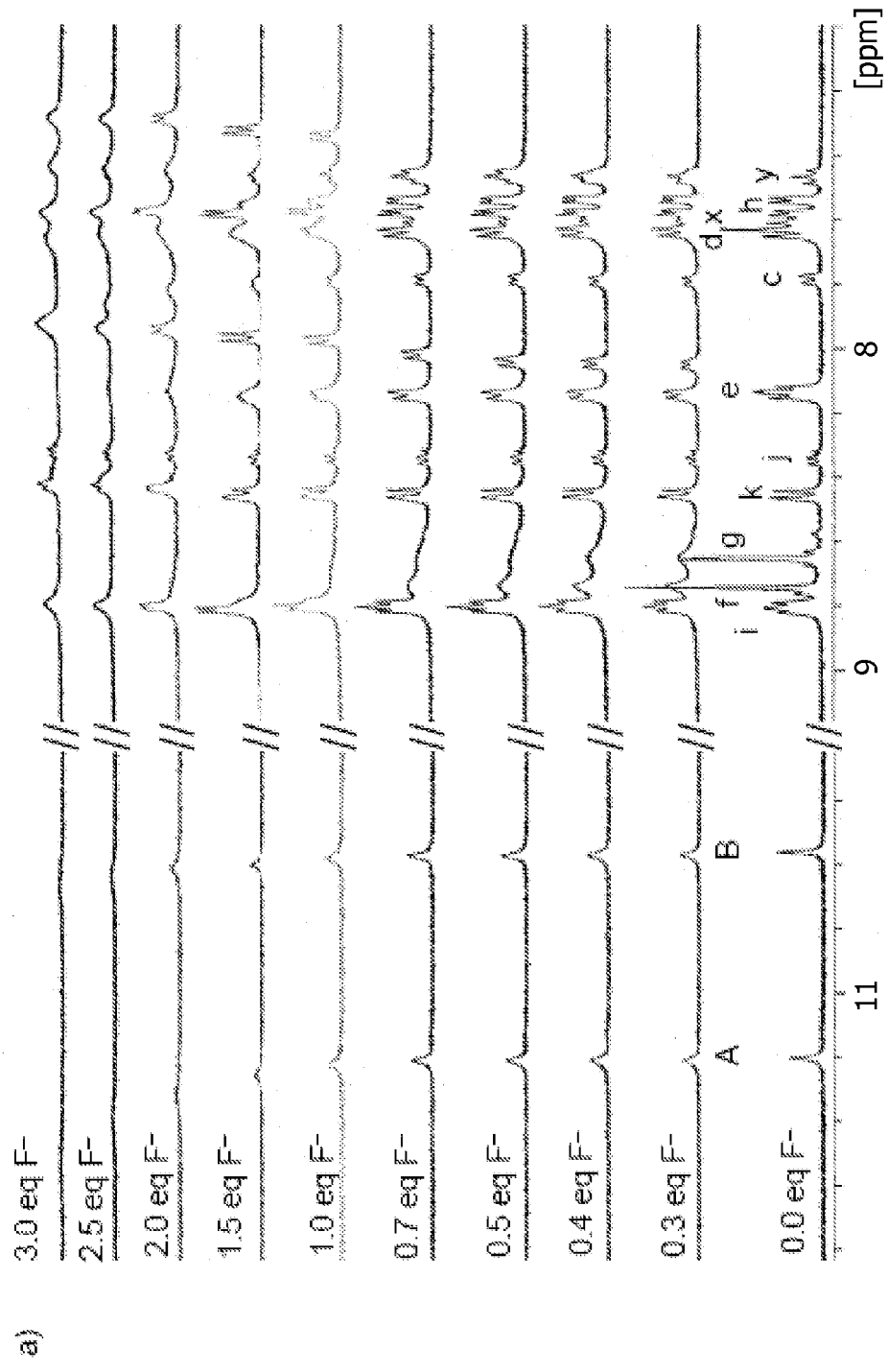
FIG. 7 is a representation of the data collected using nuclear magnetic resonance experimental procedures described in Examples 6 and 9, which involve $^1$H NMR and $^{19}$F NMR, respectively. Panels (a) and (b) disclose $^1$H NMR results for reagents LR and CR, respectively, while panel (c) discloses $^{19}$F NMR results for reagent LR.
Figure 7:
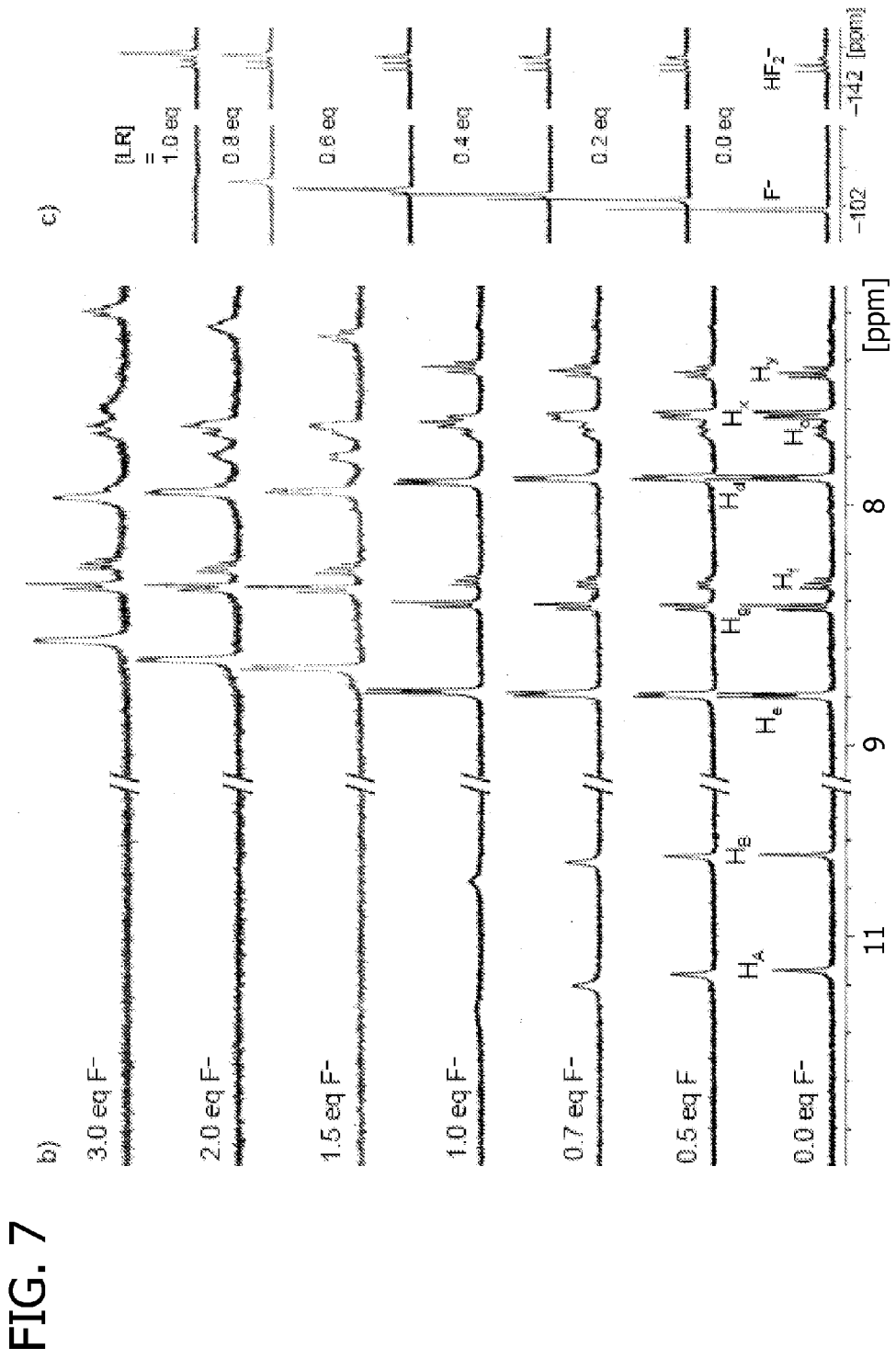

As shown in FIG. 7, panel (a), reagent LR displayed similar results as reagents N1 and SR. During the titration of LR with F$^-$ the NDI peaks at 8.65 and 8.74 ppm broadened at first and then completely disappeared at 1 molar equivalent of F$^-$ concentration due to the generation of paramagnetic NDI$^-$. radical anion character. See peaks H$_f$ and H$_g$, respectively.

Two amide peaks (H$_A$ and H$_B$) at 11.20 and 10.56 ppm shifted slightly downfield until F$^-$ concentration reached 1 equivalent. At above 1 equivalent of F$^-$ ion concentrations, however, they shifted significantly downfield and became broad. Therefore, LR, like SR, binds the first F$^-$ between two NDI units via anion-π interaction and then binds a second F$^-$ in the cavity of the tetraamide linker through hydrogen bonding interaction.

D. Control Reagent CR

As shown in FIG. 7, panel (b), control receptor CR did not significantly respond to the presence of fluoride anion, even at relatively high concentrations.

Example 7

Regeneration of Fluoride Receptor Reagents

The reversibility of the NDI/F— interaction was investigated by $^1$H NMR titration of N1 with TBAF, following the standard titration procedure outlined above. As described in Example 6, the addition of 1 molar equivalent of F⁻ to N1 made the $^1$H NMR signal of the NDI core protons ($H_A$, 8.75 ppm) disappear, as NDI was reduced to the NDI.⁻ radical anion.

Figure 6:
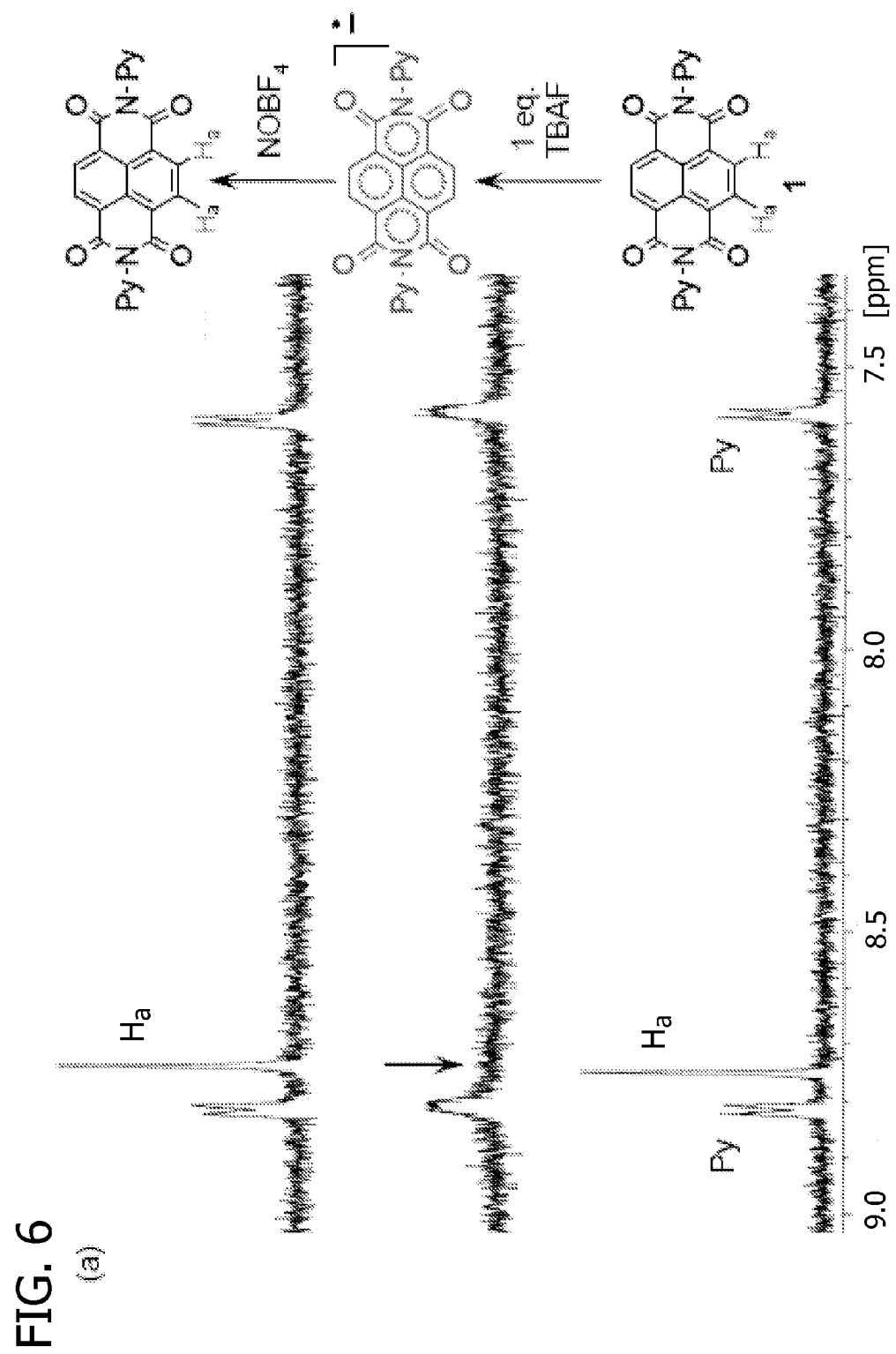
FIG. 6 is a representation of the data collected using the $^1$H NMR titration procedure set forth in Example 7 for reagents N1 and LR, shown in panels (a) and (b), respectively.
Figure 6:
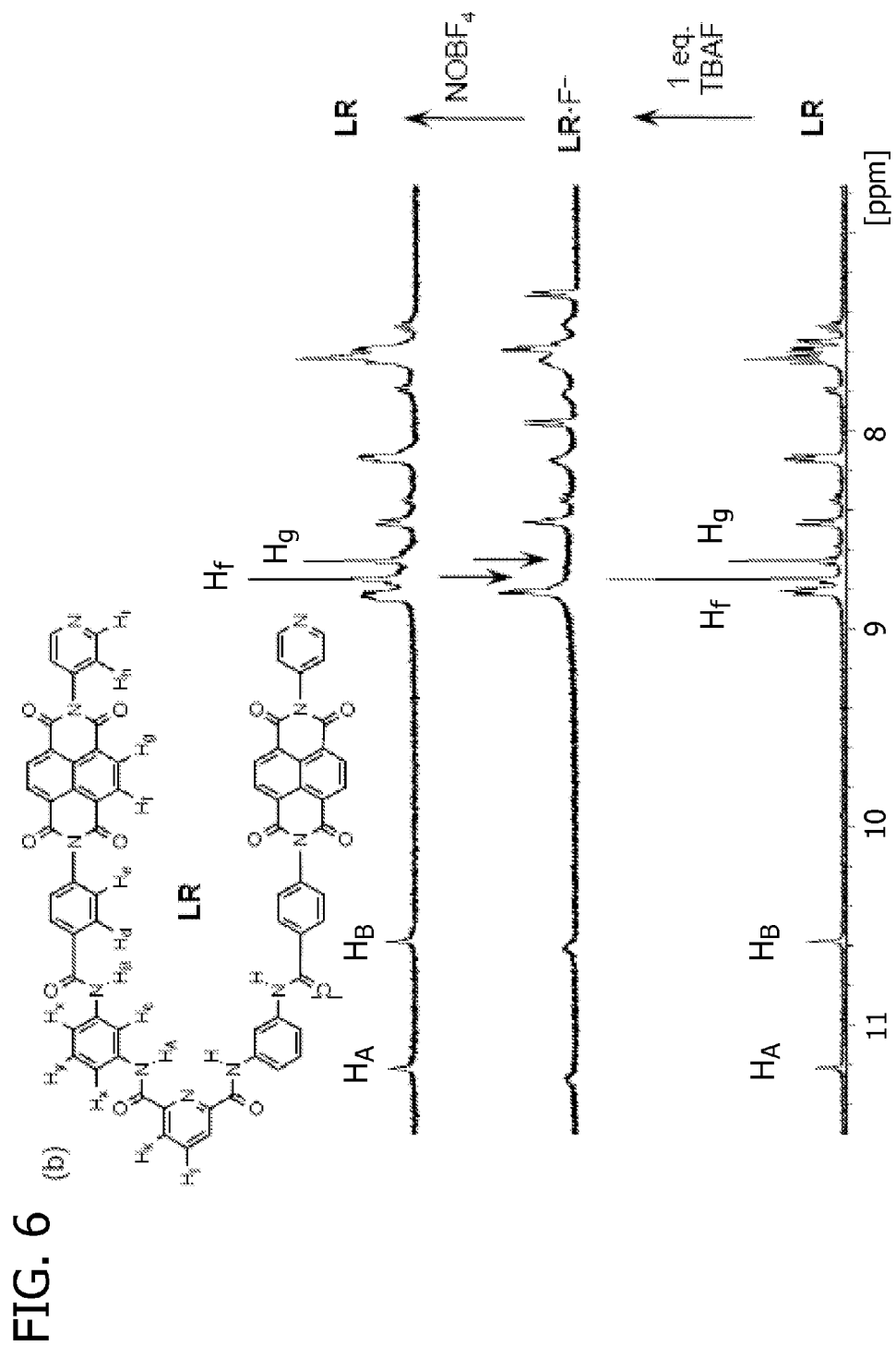

Subsequent addition of nitrosonium tetrafluoroborate ($NOBF_4$) decolorized the orange solution back to colorless and completely regenerated $H_A$ signal at 8.75 ppm, as indicated in FIG. 6, panel (a). The signal was completely regenerated upon the addition of 1 molar equivalent of $NOBF_4$ per NDI receptor unit.

The same experimental procedure was repeated with reagent LR. The results of this experiment are depicted in FIG. 6, panel (b), and indicate that receptor reagents with multiple NDI units (such as LR and SR) can also be regenerated via the addition of an oxidizing agent such as $NOBF_4$.

Therefore, the NDI/F-interaction is highly reversible. This is another indication that this interaction is indeed noncovalent in nature (e.g., no C—F bond was formed).

Example 8

$^1$H Nuclear Magnetic Resonance Spectroscopy During Titration with Other Halides To provide a comparison with the previous experiments, $^1$H Nuclear Magnetic Resonance (NMR) was conducted during titration of halides other than F⁻. The results of these tests provide better insight into the nature of the NDI/F⁻ interaction. Unless otherwise indicated, titration of the solution comprising the halide anions was conducted using the standard titration procedure outlined above.

Figure 8:
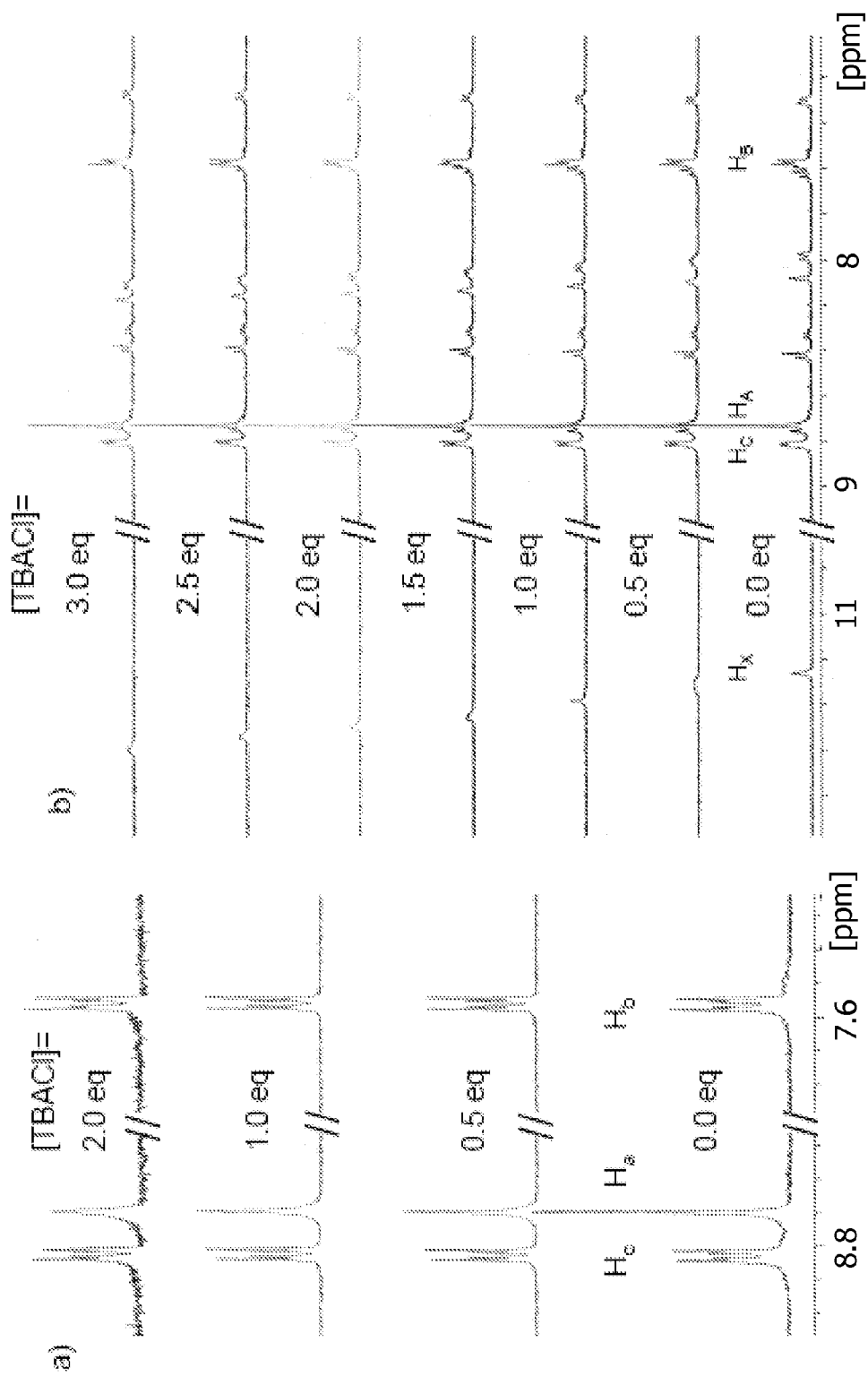
FIG. 8 is a representation of the data collected using the $^1$H NMR titration procedure set forth in Example 8 for reagents N1, SR, and LR, shown in panels (a), (b), and (c), respectively.
Figure 8:
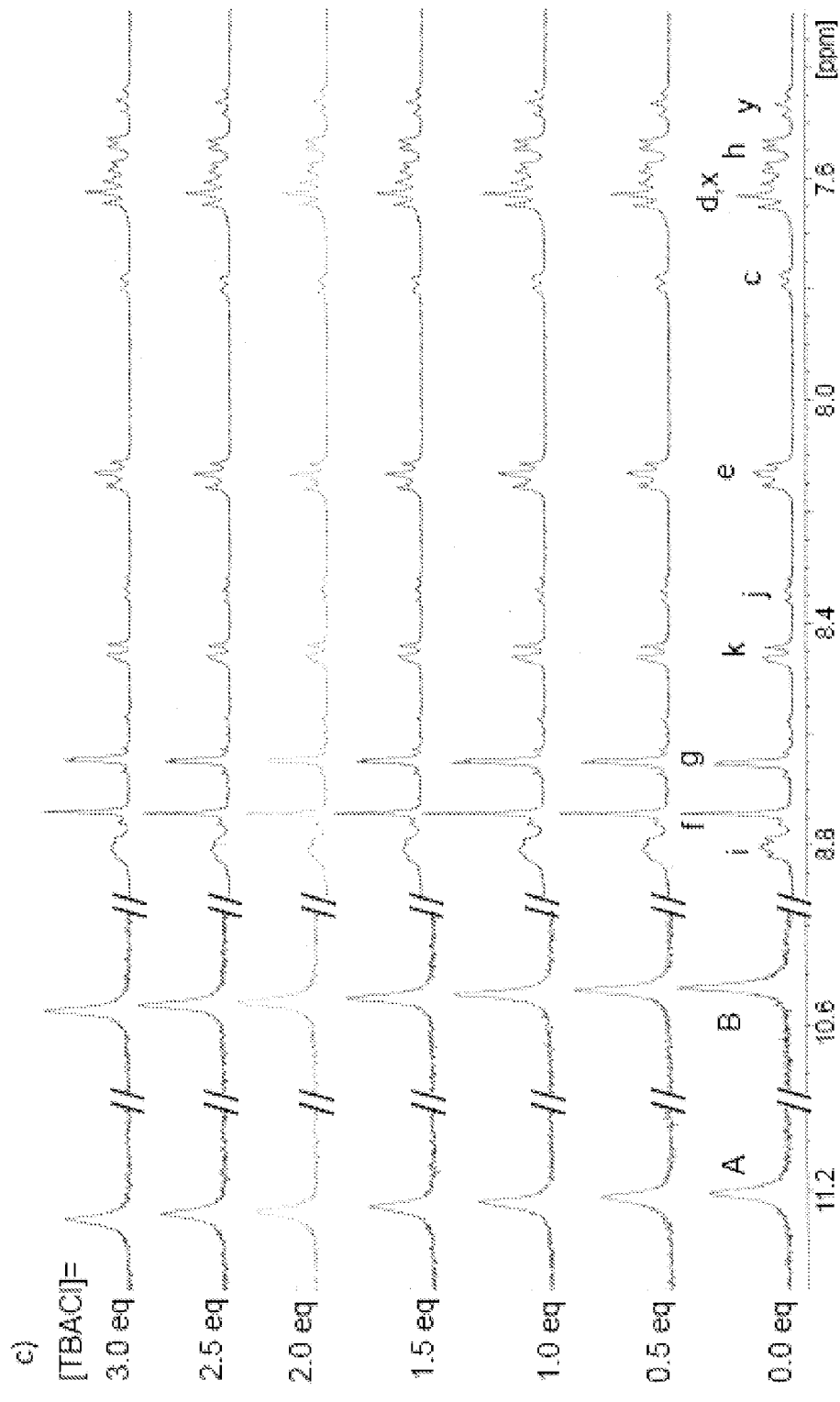

Reagent N1:

As shown in FIG. 8, panel (a), $^1$H NMR titrations of receptor N1 with Cl⁻ and other anions did not display any change, confirming that NDI/Cl⁻ anion-π interaction is weak. It can be attributed to little ionic character of NDI/Cl⁻ interaction compared to strong electronic interaction between NDI and F⁻.

Reagents SR and LR:

Titrations of receptors SR, and LR with Cl⁻, Br⁻, and I⁻, respectively, did not affect the NDI protons. Only amide protons of SR and LR shifted downfield in the presence of Cl⁻, showing that Cl⁻ preferentially binds inside the cavities of amide linkers via stronger N—H . . . Cl⁻ H-bonding interaction. The results of this titration for reagents SR and LR are displayed in FIG. 8 at panels (b) and (c), respectively.

Example 9

$^{19}$F Nuclear Magnetic Resonance Spectroscopy During F⁻ Titration

Fluoride anion recognition by NDI receptors was also observed from $^{19}$F NMR spectroscopy.

A solution containing reagent LS was titrated into the aqueous $nBu_4NF$ mixture. Titration of reagent LS was generally conducted in accordance with the standard titration procedure outlined above. Specifically, the $nBu_4NF$ concentration in the titrand was maintained at 4 mM in DMSO solvent. The concentration of reagent LR in the titrant was maintained at 30 times that amount (120 mM) to minimize dilution effects during titration.

A. Reagent N1

As shown in FIG. 15, panel (c), the $^{19}$F NMR spectrum of tetra-n-butylammonium fluoride ($TBAF.3H_2O$) in DMSO-$d_6$ shows a strong singlet at −102 ppm for F⁻ ion and a weak doublet at −142.5 ppm corresponding to $HF_2^-$. Titrations of TBAF with N1 caused an up-field shift of the −102 ppm signal (FIG. 15(c)), which indicates shielding of F⁻ ion by surrounding NDI receptors. The disappearance of the F⁻ signal at a 1:1 TBAF/N1 molar ratio may be attributed to an oxidation of F⁻ to F. as a result of F⁻→NDI ET process that produces NDI.⁻ radical anion. Although we previously discussed a possibility of C—F bond formation as one of the modes of NDI/F⁻ interaction, it could not be confirmed by any evidence, including $^{19}$F NMR, as no new signal corresponding to a covalent C—F bond was observed.

B. Reagent LS

As described above, a solution containing reagent LS was titrated into the aqueous $nBu_4NF$ mixture. As shown in FIG. 7, panel (c), the intensity of the peak at −102 ppm was observed to decrease with increasing concentration of reagent LS; after addition of one equivalent of LS, the peak at −102 ppm disappeared entirely. The intensity of the peak at −143.5 ppm, corresponding to $DF_2^-$, increased with increasing concentration of reagent LS and broadened, possibly as a result of unresolved coupling with both the amide and bifluoride deuterium atoms.

Example 10

Electrospray Ionization Mass Spectrometry (ESI-MS)

ESI-MS experiments were recorded on a JEOL AccuTOF JMS-T100LC mass spectrometer using negative ionization mode. The results of these experiments are generally shown in FIG. S2.

Figure 9A:
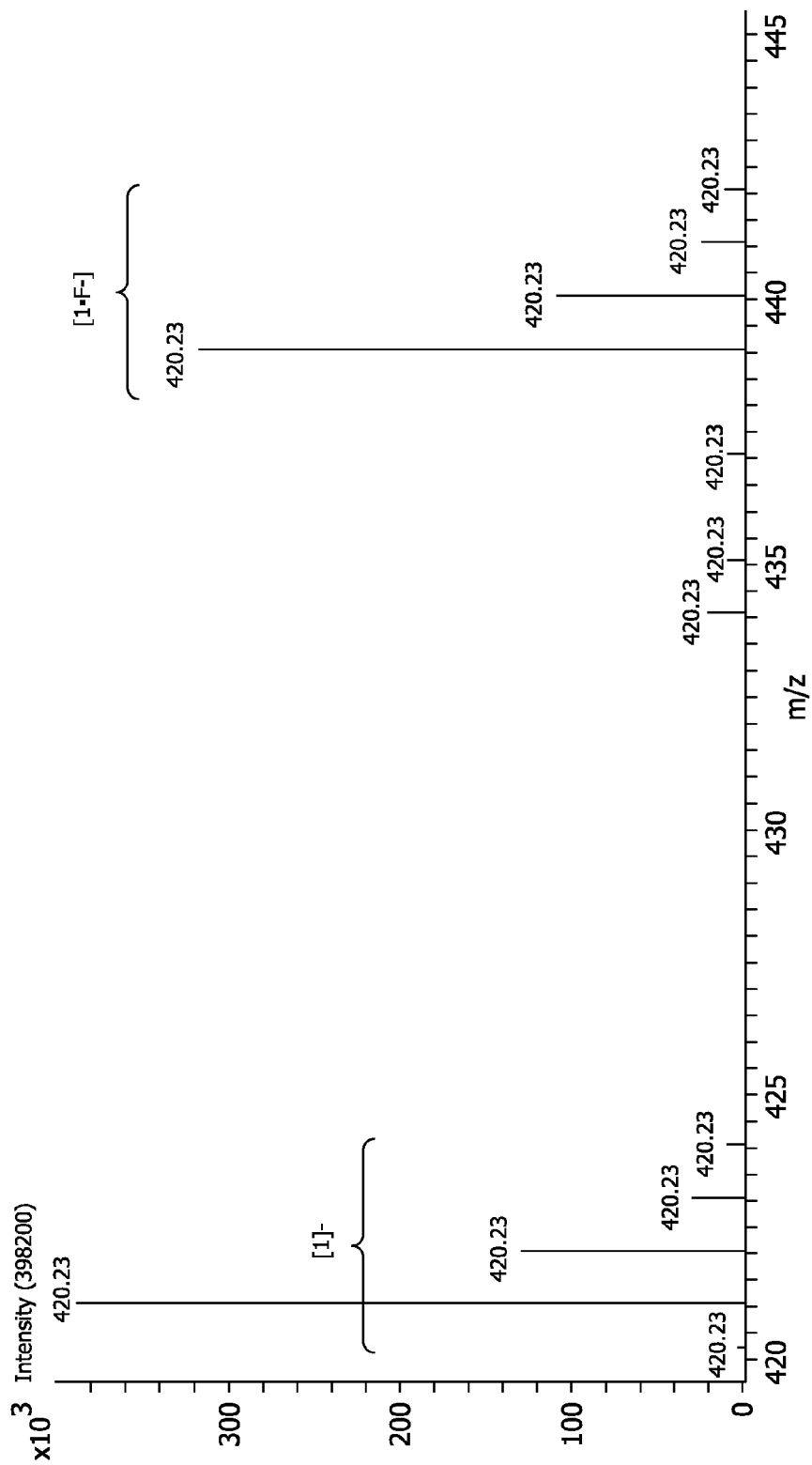
FIGS. 9A, 9B, and 9C are representations of the data collected using the Electrospray Ionization Mass Spectrometry (ESI-MS) procedure set forth in Example 10 for reagent N1. More particularly.
Figure 9B:
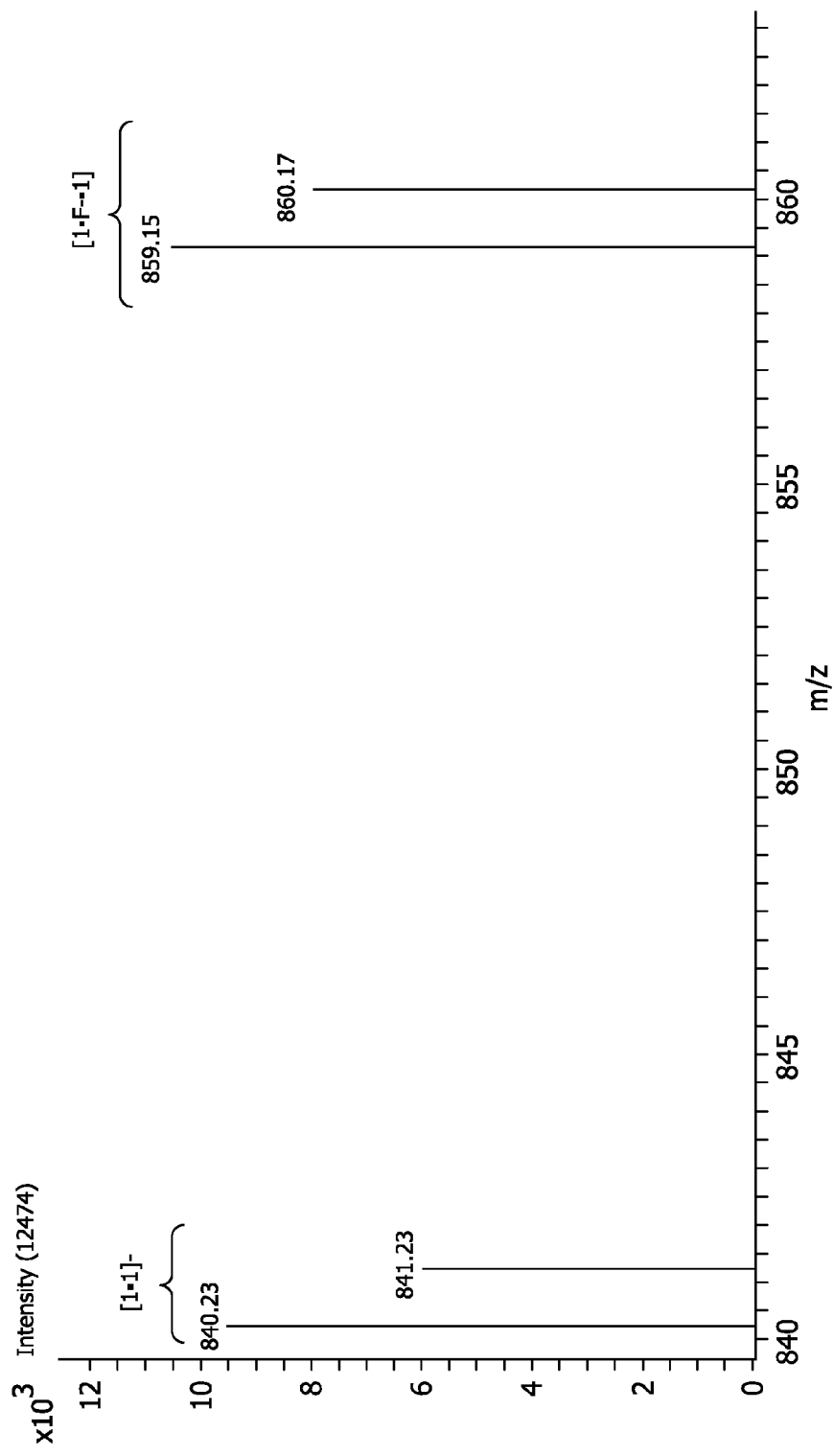

Generally, ESI-MS data were taken in the presence of ≤1 molar equivalent of F⁻, and show the isotope distribution patterns of receptors N1, SR, and LR, as well as the respective F⁻ complexes. FIG. 9A shows data regarding the presence and isotope distribution patterns of species [N1]⁻, [N1.F⁻], and [N₁.F⁻.N1] in panels (a) and (b). Similarly, FIG. 9B shows data regarding the presence and isotope distribution patterns of species [SR]⁻ and [SR.F⁻] in panel (d), and [LR]⁻ and [LR.F⁻] in panel (e), respectively.

Figure 9C:
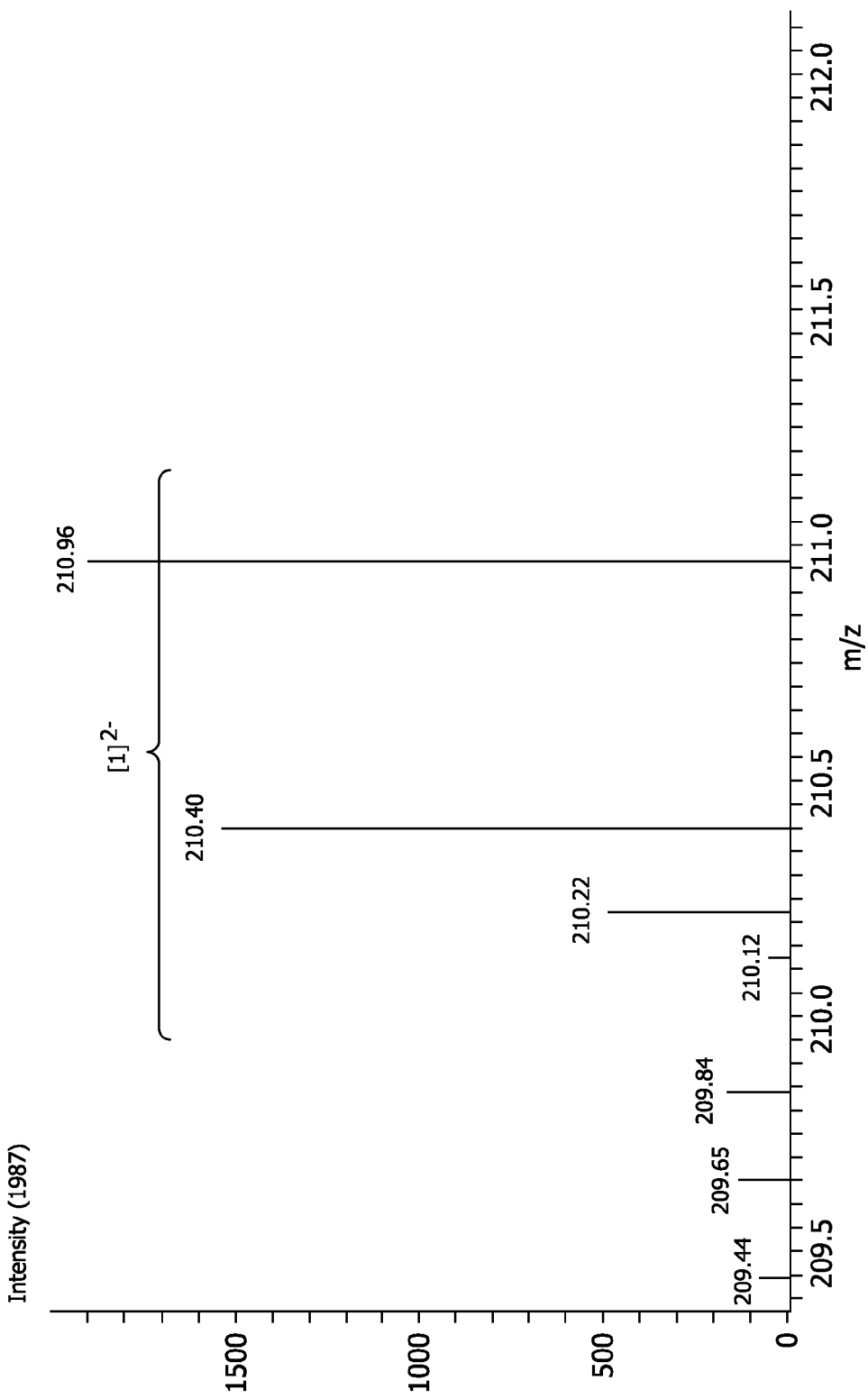
Figure 9E:
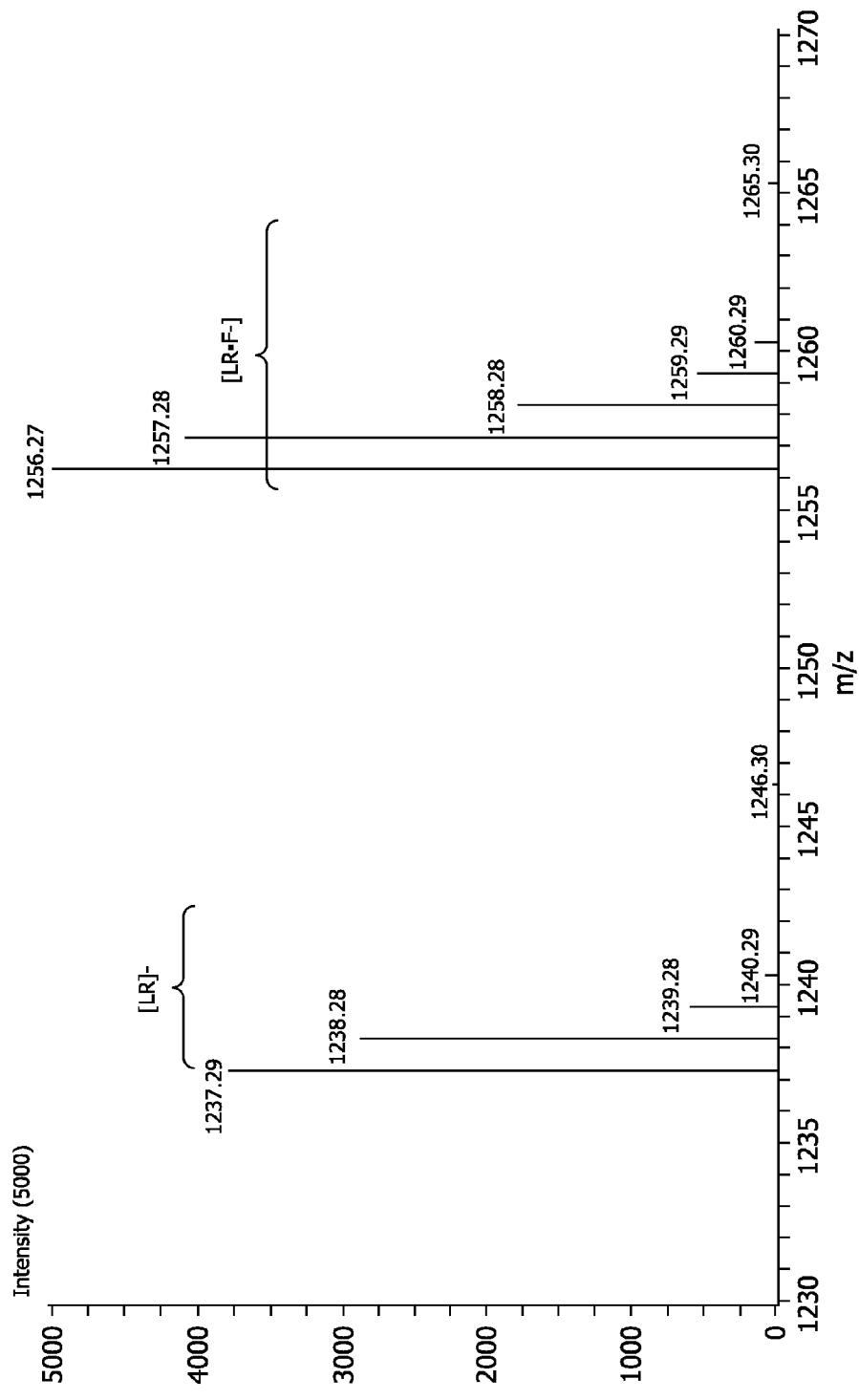
Figure 9F:
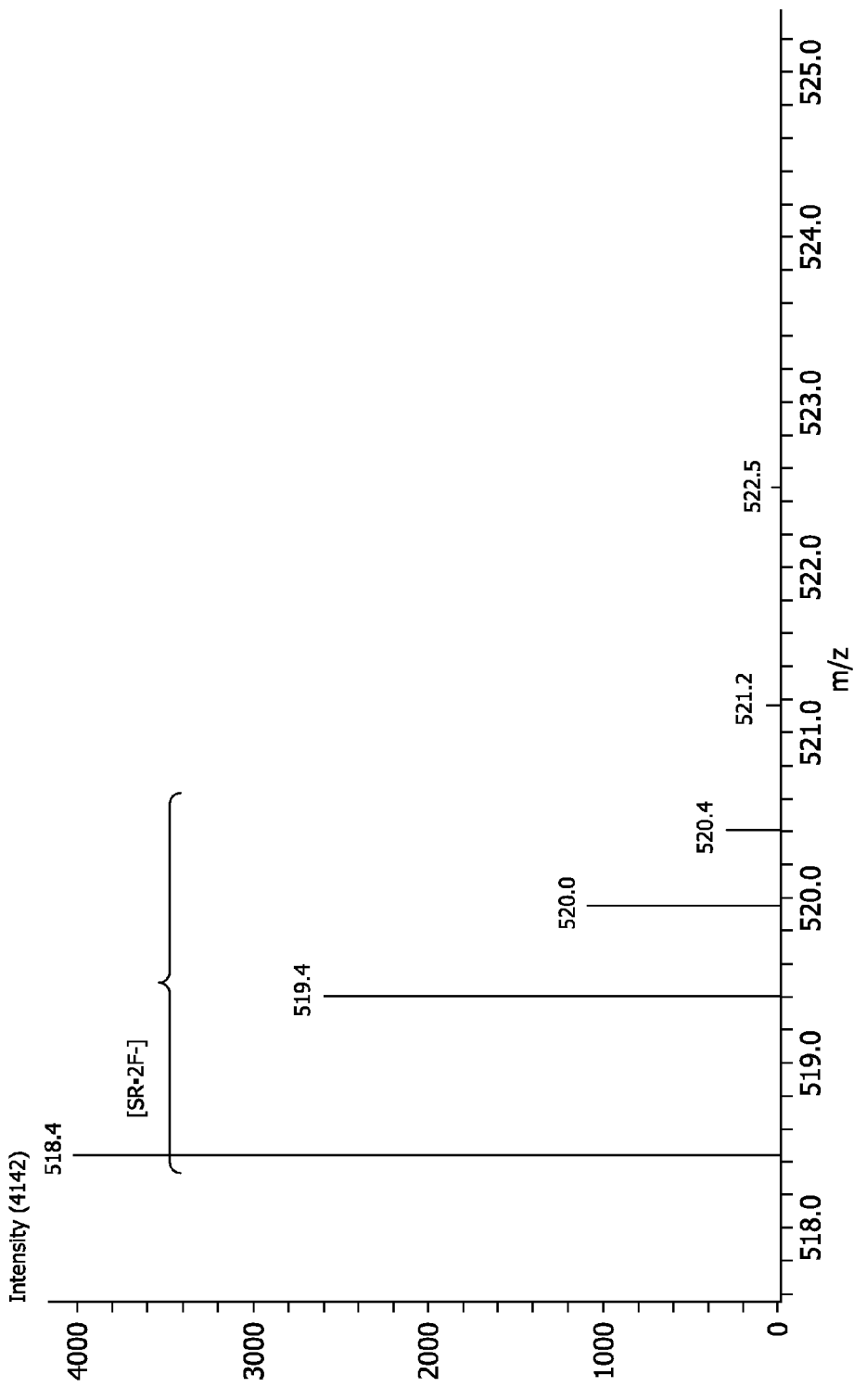
FIGS. 9F and 9G are representations of the data collected using the ESI-MS procedure set forth in Example 10 for reagents SR and LR, respectively, in the presence of 2 equivalents of F$^-$ anions. More particularly.
Figure 9G:
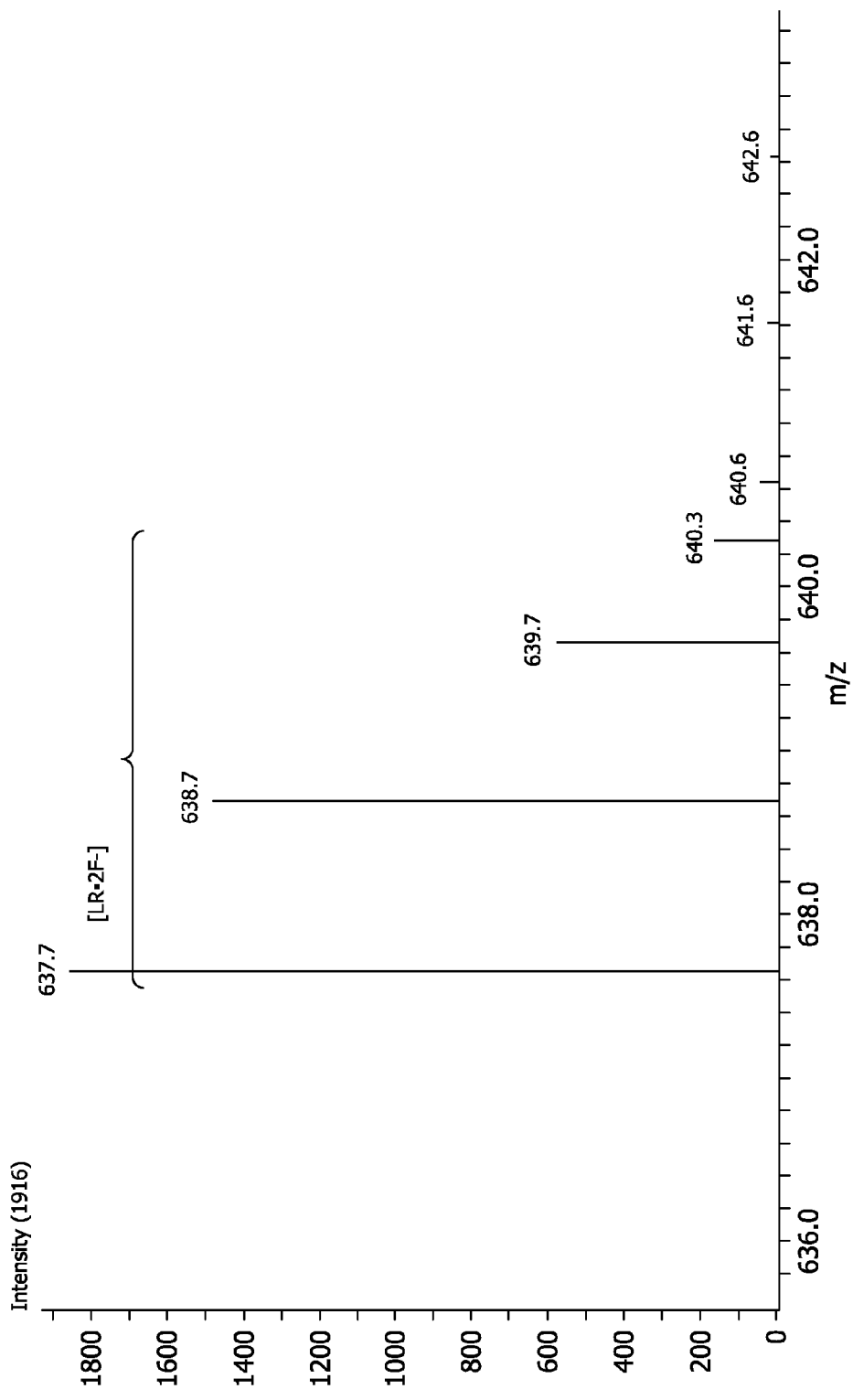

As shown in FIG. 9A, panel (c), ESI-MS in the presence of excess F⁻ reveals only [N1]²⁻ dianion at m/z 210.40, but does not show any signal representing $[N1/F_n]^{n-}$ (n≥1) complexes. As shown in FIG. 9C, ESI-MS of SR and LR in the presence of 2 equiv. of F⁻ revealed m/z 518.40 and 637.70 signals that represent [SR.2F⁻] and [LR.2F⁻] complexes, shown at panels (f) and (g), respectively.

Example 11

Isothermal Titration Calorimetry (ITC)

Isothermal titration calorimetry (ITC) studies were conducted on a MICROCAL VP-ITC ultra-sensitive isothermal titration microcalorimeter. The VP-ITC unit, with a precise temperature control set at 25.0±0.1° C., directly measured heat evolved or absorbed in solution as a result of infection of reactant. For control, a reference cell was filled with dimethyl sulfoxide (DMSO). Titrations were run at 25° C.

Before the experiment, all the samples were degassed at 25° C. for 10 minutes us the THERMOVAC (a vacuum thermostating system). Each of 40 injections of 6 μL of a halide solution was delivered into a solution (1 mM) of reagent LS over 12 seconds by a syringe spinning at 270 rpm, with a 240 second equilibration time between injections. The instrument was controlled by MICROCAL OBSERVER software comprising a 16-bit A/D converter board for data acquisition, and a second interface board for calorimetric control. Heats of dilution were taken into account using data from control experiments, in which DMSO was injected into reagent LS in DMSO solution.

From these experiments, it has been confirmed that a 1:1 and 1:3 (reagent LS:F⁻ anion) type of stoichiometry occurs during F⁻ titration. Initially, π-anion-π interaction takes place, at concentrations up to one molar equivalent of F⁻ ion. At concentrations greater than one equivalent of F⁻, the NH proton becomes directly involved in a second binding process through hydrogen bonding, a conclusion which is supported by the $^1$H NMR experiments described above. The association constants for these two processes have been determined as follows: $K_1 = 4.11\ 10^4\ M^{-1}$ and $K_2 = 2.69\ 10^4\ M^{-1}$. See Table 1.

Interestingly, however, the formation of a complex between reagent LR and other halides, such as Cl⁻, Br⁻ and I⁻, appear to endothermic with continuous decay and are primarily driven by entropy. In a solution with DMSO, the association constants for Cl⁻, Br⁻ and I⁻ have been determined to be $K_a = 319$, $K_a = 145$ and $K_a = 105$ respectively. These results indicate that F⁻ binds much more strongly with the instant fluoride receptor reagents than other halide ions. Even in presence of excess of Cl⁻ ion, LR binds F⁻ selectively (FIG. 7(b)). Using these characteristic ITC patterns, one could determine whether a given test solution contains F⁻ only or, alternatively, whether the test solution contains is a mixture of F⁻ with another halide anion.

In addition to the above species, the same experimental procedure was followed with control reagent CR. A summary of the experimental results is provided in Table 1.

TABLE 1

Association constants ($K_a$) and ΔG of N1, SR, LR, and CR for F⁻ and Cl⁻ recognition derived from ITC experiments (DMSO, 298 K).

| Receptor | X⁻ | $K_1\ M^{-1}$ | $\Delta G_1$ kcal $M^{-1}$ | $K_2\ M^{-1}$ | $\Delta G_2$ kcal $M^{-1}$ |
|---|---|---|---|---|---|
| N1 | F⁻ | $8.47 \times 10^3$ | −5.36 | | |
| N1 | Cl⁻ | 53 | −2.35 | | |
| LR | F⁻ | $4.11 \times 10^4$ | −6.29 | $2.69 \times 10^4$ | −6.04 |
| LR | Cl⁻ | 319 | −3.42 | | |
| SR | F⁻ | $9.03 \times 10^8$ | −12.20 | $4.42 \times 10^5$ | −7.70 |
| SR | Cl⁻ | $1.73 \times 10^3$ | −4.41 | | |
| CR | F⁻ | 259 | −3.28 | | |
| CR | Cl⁻ | 100 | −2.71 | | |

Example 12

Fluorescence Spectroscopy

Fluorescence spectroscopy was introduced to determine the sensitivity of NDI-based F⁻ ion sensors at very low concentrations. Fluorescence spectra were collected on a HORIBA JOBIN YVON FLUOROMAX-4 spectrofluorometer.

Titration of 1 nM solution of SR in DMSO with 30 nM solution of F⁻, probed by 381 nm excitation, displayed up to 4.5-fold amplification of original 430 nm fluorescence peak of the NDI unit and 20-fold amplification of a new peak at 465 nm. The nM level F⁻ ion sensitivity of SR ($K_a = 9.03 \times 10^8\ M^{-1}$, DMSO, 298 K) was also measured from ITC analysis (Table 1). Receptor N1 (10 μM in DMSO) showed a similar fluorescence profile and 5.5-fold enhancement of 465 nm emission peak at 30 equiv. of F⁻.

Figure 4:
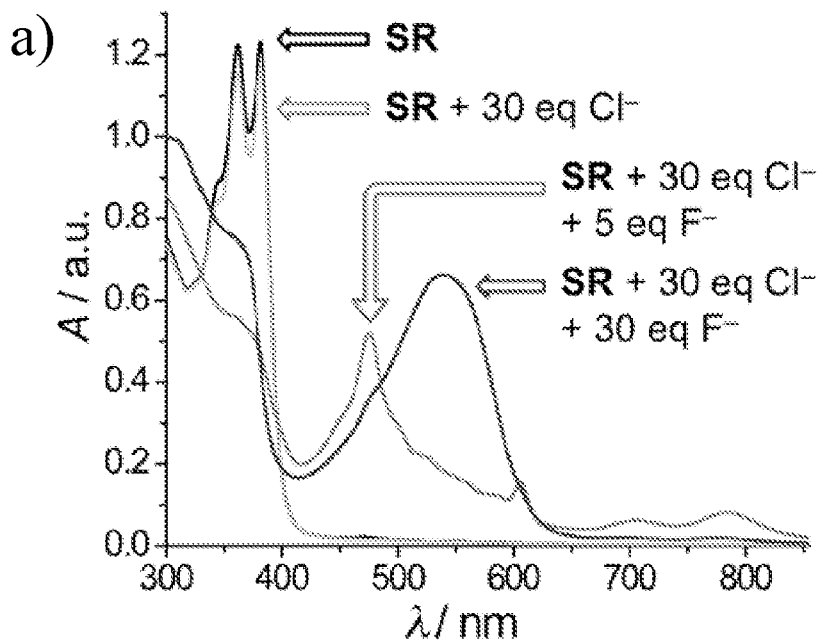
FIG. 4 is a representation of the UV/Visible light spectroscopy data and fluorescence spectroscopy data obtained using the procedures set forth in Examples 4 and 12, respectively, for reagent SR. Panel (a) discloses the spectroscopy data obtained from titration of SR with Cl$^-$ anion, while panel (b) discloses the spectroscopy data obtained from titration of SR with F$^-$ anion.
Figure 4:
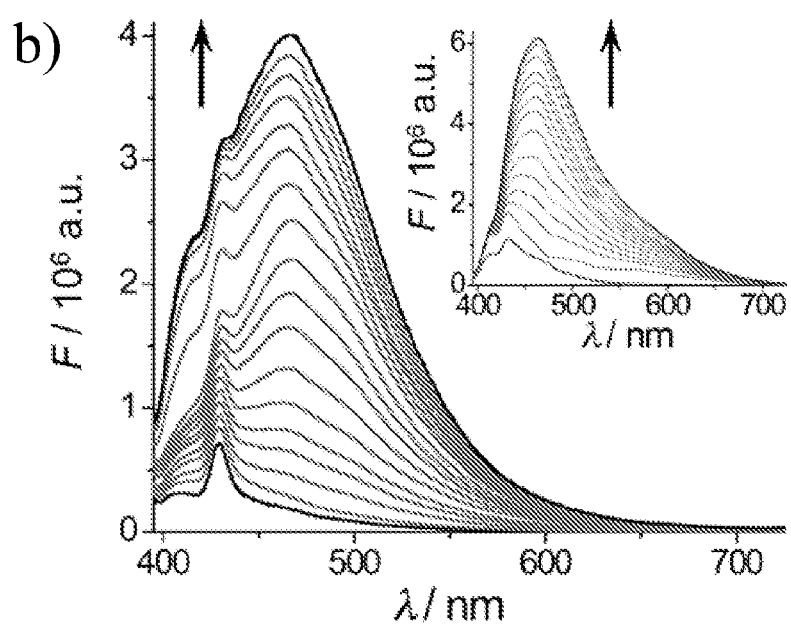

The results for reagent SR are illustrated in FIG. 4, panel (f). The results for reagent N1 are disclosed in the inset, at the top left of panel (f).

Such high degrees of F⁻ ion sensitivity of NDI-based receptors at very low concentrations bodes well for their potential applications as F⁻ ion sensors. Accordingly, this further confirms that F⁻ is interacting with NDI as well as NH groups, stabilizing the excited state of NDI and thus provoking fluorescence enhancement.

On the other hand, no noticeable changes in color or emission spectra were observed when the titration solution instead contained Cl⁻, Br⁻ and/or I⁻ anions, even at high concentrations up to 30 molar equivalents. These results indicate that receptors SR and LR exhibit excellent selectivity for F⁻ over other halide ions in DMSO.

Example 13

Electrochemistry and Spectroelectrochemistry

Figure 11:
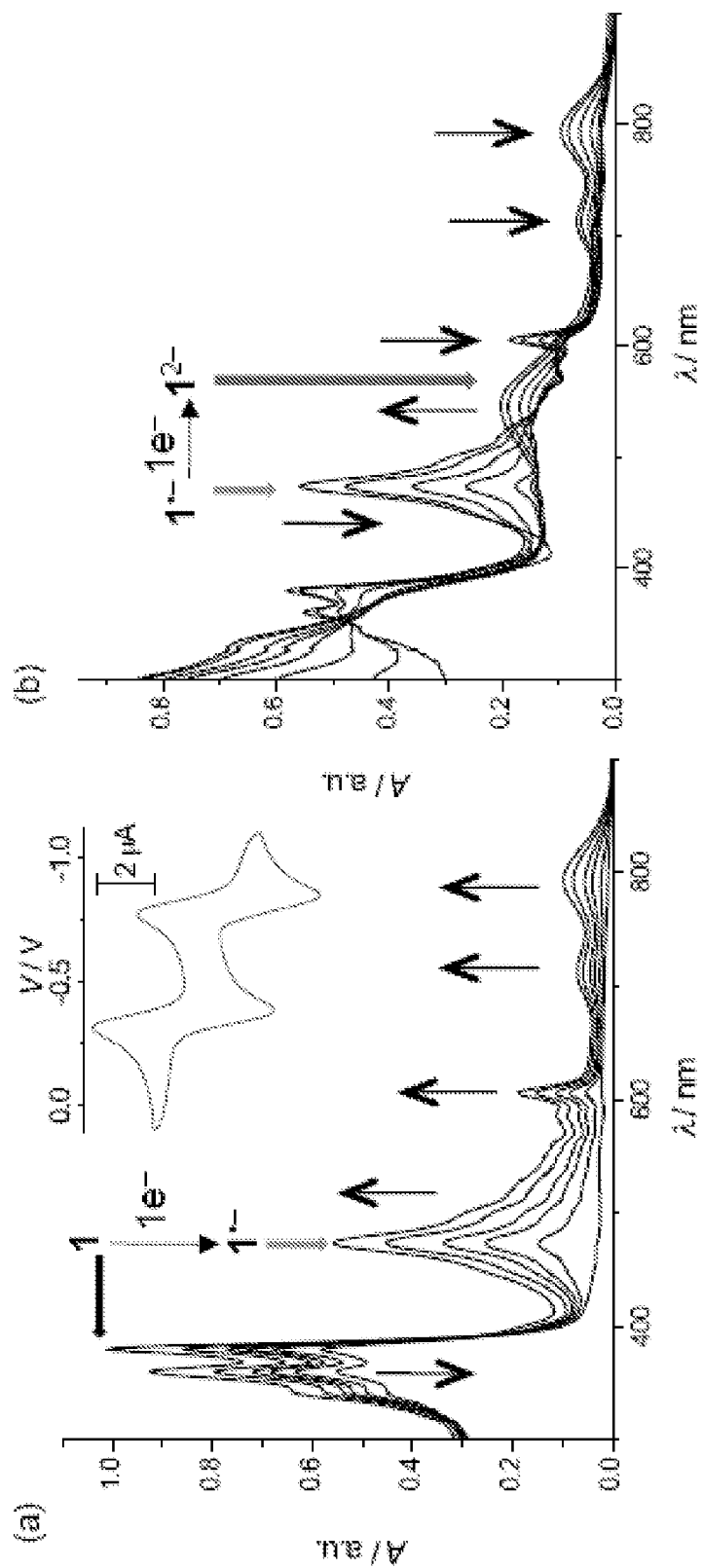

Cyclic voltammetry (CV) was conducted on a PRINCETON APPLIED RESEARCH (PAR) VERSASTAT-3-200 potentiostat/galvanostat instrument using a standard electrochemical cell, consisting of a Pt-disk working electrode, Pt-wire counter electrode, and Ag/AgCl (3 N aq. NaCl) reference electrode. CV was recorded at 1 mM of reagent N1 in 0.1 M TBAPF6/DMF supporting electrolyte solution at room temperature at 100 mV/s scan rate (FIG. 11). CV shows two step one-electron reduction of N1, first to N1.⁻ at $E_1$ ½=−342 mV and then to N1²⁻ at $E_2$ ½=−804 mV.

Spectroelectrochemistry was conducted in an Optically Transparent Thin Layer Electrochemical Cell (OTTLE) fitted with a Pt-gauge working electrode, Pt-wire counter electrode, and Ag/AgCl (3 N aq. NaCl) reference electrode using 0.5 mM of reagent N1 in 0.1 M TBAPF$_6$/DMF supporting electrolyte solution at room temperature. UV/Vis spectra were recorded at 2 min. intervals on a PERKINELMER LAMBDA-25 UV/Vis spectrophotometer while the applied potential was controlled by the PAR potentiostat, using Virtual Potentiostat software. For the N1.⁻ radical anion formation the applied potential (Eap) was held at −450 mV until the corresponding spectra reached the saturation point and did not show any difference between two consecutive spectra. The same was done for the detection of N1²⁻ by setting $E_{ap}$ at −900 mV.

FIG. 11 provides a schematic representation of the results of this procedure. As shown in panel (a), spectroscopic changes of compound N1 (0.5 mM in 0.1 M Bu$_4$NPF$_6$/DMF) at $E_{ap}$=−450 mV vs. Ag/AgCl (3 N aq. NaCl) show the formation of N1.⁻, while panel (b) at $E_{ap}$=−900 mV shows the formation of N1²⁻ at 25° C. The inset, shown at the upper right of panel (a), represents a cyclic voltammogram of N1 showing two one-electron reductions of NDI to NDI.⁻ radical anion and NDI²⁻ dianion.

Example 14

Electron Paramagnetic Resonance (EPR) Spectroscopy

EPR spectra were obtained from a BRUKER ELEXSYS-500 spectrometer using the following settings: X-band, microwave frequency 9.3902 GHz; microwave power 1 mw; and modulation amplitude 1 Gauss (G) at 298 K. The microwave frequency was measured with a built-in digital counter and the magnetic field was calibrated using 2,2-diphenyl-1-picrylhydrazyl (DPPH; g=2.0037). Modulation amplitude and microwave power were optimized for high signal-to-noise ratio and narrow peaks.

An orange solution of reagent N1 in the presence of 1 molar equivalent of F— ion in DMF was prepared. The EPR spectrum showed the characteristic signals of delocalized NDI.⁻ radical anion (g=2.0030) with hyperfine structures. As expected, the colorless solution of N1 in the absence of F⁻ ion, as well as the pink solution of N1 in the presence of large excess of F⁻ ion, did not show any EPR signals (see FIG. 10).

Figure 10:
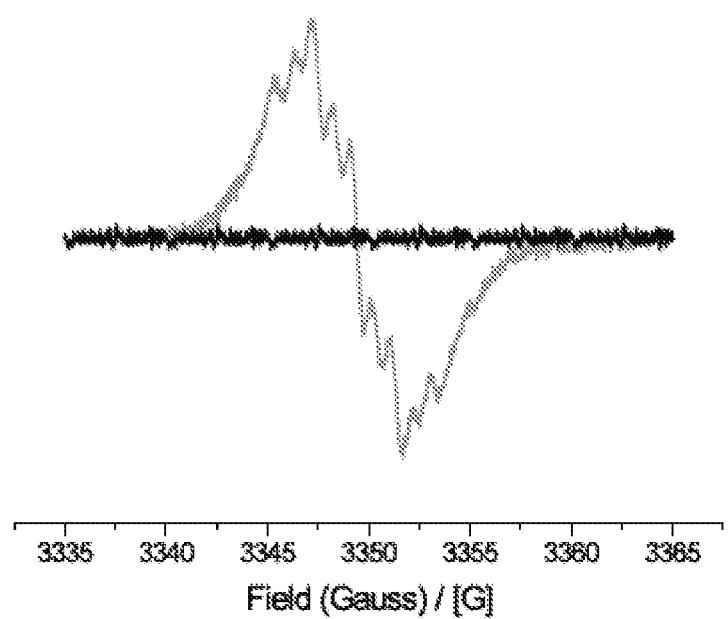
FIG. 10 is a representation of the data collected using the Electron Paramagnetic Resonance (EPR) spectroscopy procedure set forth in Example 14 for reagent N1.

FIG. 10 shows the EPR spectrum of N1 (1 mM/DMF) in the absence of F⁻ ion (dark trace), in presence of 1 equiv of F⁻ (medium trace), and in presence of 30 equiv of F⁻ (light trace) at room temperature. The medium spectrum shows a hyperfine splitting pattern, indicating the formation of delocalized NDI.⁻ radical anion (g=2.0030).

Example 15

Demonstration of Fluoride Anion Sensing in Toothpastes

For the detection of F⁻ ion in toothpastes, small samples (1 gram) of each of two toothpastes (COLGATE anticavity fluoride toothpaste and ORAJEL toddler fluoride-free toothpaste) were extracted separately in 2 mL of aqueous DMSO. The COLGATE toothpaste contained 0.24% (w/v) NaF. Each resulting suspension was filtered to obtain colorless clear solution, which were separately added to 10 μM SR solutions.

To our delight, the colorless SR solution turned light orange and displayed the absorption spectrum of NDI.⁻ radical anion when it came into contact with the F⁻ containing toothpaste solution (COLGATE). On the other hand, the F⁻-free ORAJEL toothpaste did not change the spectrum of the receptor (overlapping green and black traces), demonstrating that receptor SR is an effective fluoride sensor in water containing media.

The results of this experiment are represented in FIG. 12, which demonstrates the detection F⁻ ion in toothpastes by SR (10 μM) in wet DMSO using UV/Vis spectroscopy. The black trace represents SR without toothpaste; the light trace, SR with anticavity adult toothpaste containing 0.24% NaF; and the medium trace, SR with F⁻ free toddler toothpaste.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

a compound of formula (III-K):
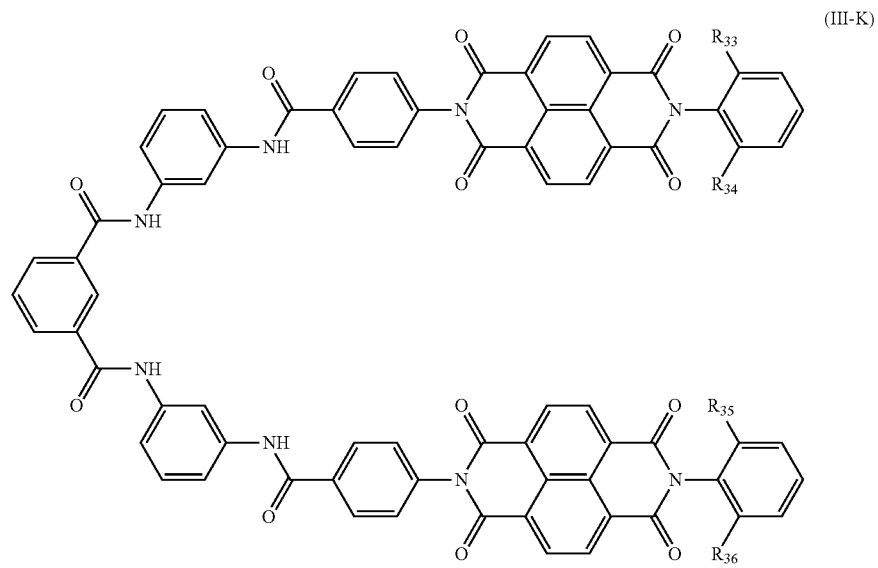
wherein $R_{33}$, $R_{34}$, $R_{35}$, and $R_{36}$ are each independently alkyl or alkyl ether;
a compound having the formula (SR):
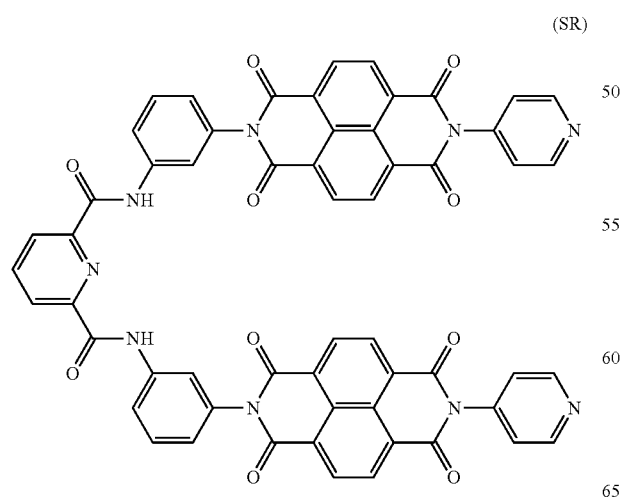

and a compound having the formula (LR):
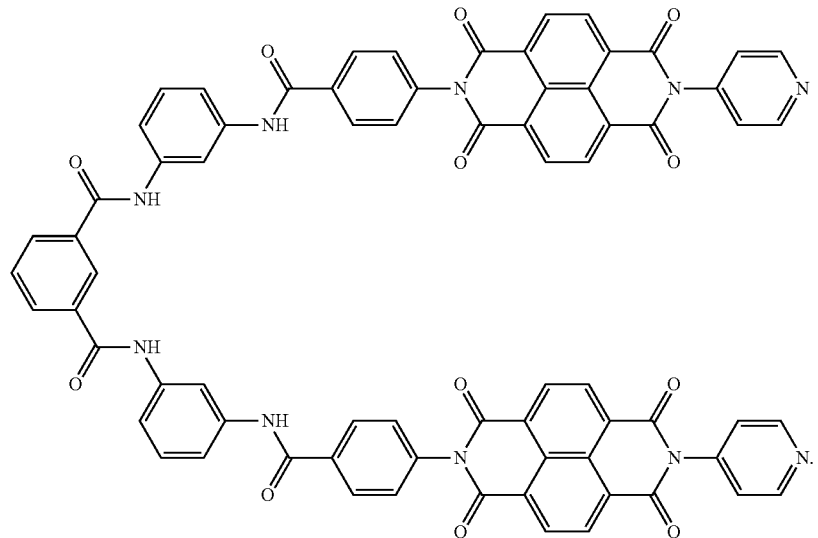

What is claimed is:

1. A method for detecting fluoride anion (F⁻) in a material comprising:
    contacting the material with a fluoride receptor reagent to form a complex involving anion-π interactions, wherein the fluoride receptor reagent comprises an N-aryl or heteroaryl derivative of 1,4,5,8-naphthalenediimide (NDI) having the formula (I):

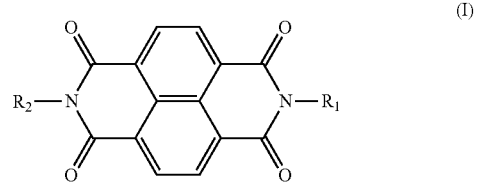

wherein $R_1$ comprises a substituted or unsubstituted aryl or heteroaryl moiety; and $R_2$ is independently a substituted or unsubstituted aryl or heteroaryl moiety, or $R_2$ comprises a second NDI moiety comprising a second NDI unit and having the formula:

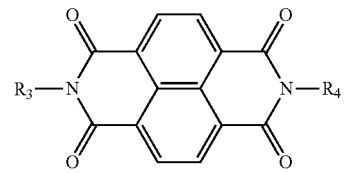

wherein $R_3$ is a linking group connecting the second NDI unit to the nitrogen atom of formula (I) and comprising a substituted or unsubstituted aryl or heteroaryl moiety; and $R_4$ is independently a substituted or unsubstituted aryl or heteroaryl moiety, and detecting the presence of fluoride anions as indicated by a colorimetric or fluorometric response.

2. The method of claim 1 wherein the fluoride receptor reagent has the formula (II):

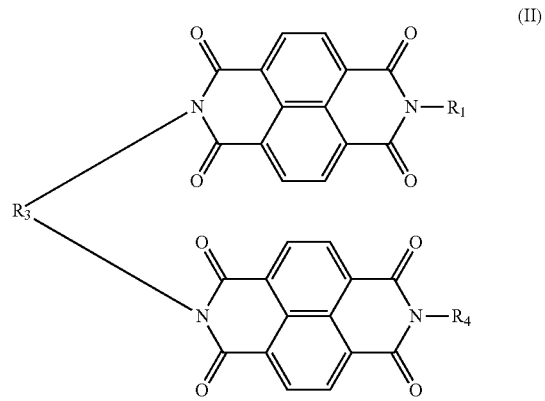

wherein $R_1$ and $R_4$ are each independently a substituted or unsubstituted aryl or heteroaryl moiety; and $R_3$ is a linking group comprising a substituted or unsubstituted aryl or heteroaryl moiety.

3. The method of claim 2 wherein the $R_3$ linking group comprises a pyridyl moiety.

4. The method of claim 3 wherein the fluoride receptor reagent has the formula (III):

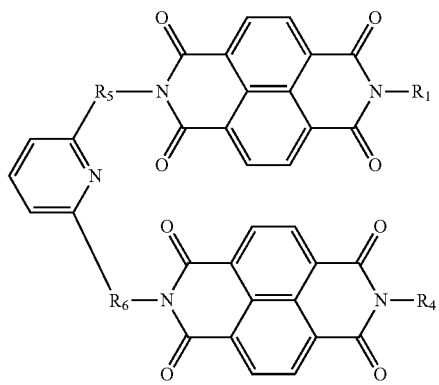

(III)

wherein $R_5$ and $R_6$ are intermediate linking groups, each intermediate linking group independently comprising a substituted or unsubstituted aryl or heteroaryl moiety.

5. The method of claim 4 wherein $R_5$ and $R_6$ each comprise an amide functional group bonded to the central pyridyl moiety.

6. The method of claim 1 wherein one or more of $R_1$, $R_2$, $R_3$ and $R_4$ are substituted aryl or heteroaryl-comprising moieties.

7. The method of claim 6 wherein the substituents on the one or more substituted aryl or heteroaryl-comprising moieties $R_1$, $R_2$, $R_3$ and $R_4$ are independently selected from the group consisting of halo, —OH, =O, —C(O)OH, —C(O)OR$_7$, —C(O)NR$_8$R$_9$, —CH$_2$NR$_8$R$_9$, nitro (—NO$_3$), sulfonate (—SO$_3^-$) hydrocarbyl and substituted hydrocarbyl, wherein $R_7$, $R_8$, and $R_9$ are each independently hydrocarbyl or substituted hydrocarbyl.

8. The method of claim 7 wherein the hydrocarbyl and substituted hydrocarbyl substituents are independently selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl and heteroarylalkyl.

9. The method of claim 1 wherein the fluoride receptor reagent is selected from the group consisting of:

a compound of formula (I-A):

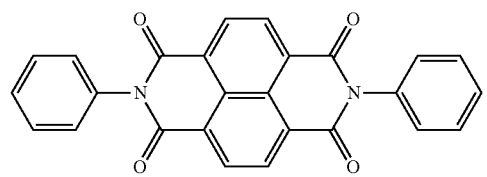

(I-A)

a compound of formula (I-B):

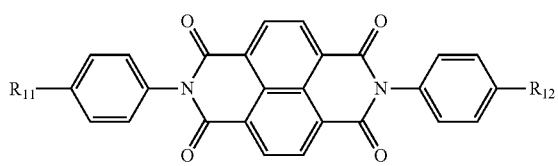

(I-B)

wherein $R_{11}$ and $R_{12}$ are each independently alkyl, alkyl ether, or nitro;

a compound of formula (I-C):

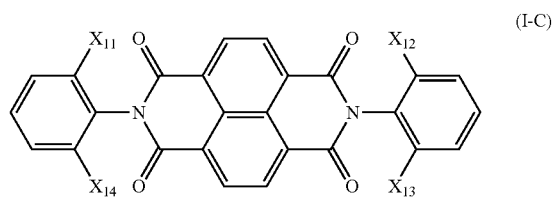

(I-C)

wherein $X_{11}$, $X_{12}$, $X_{13}$, and $X_{14}$ are each independently halo;

a compound of formula (I-D):

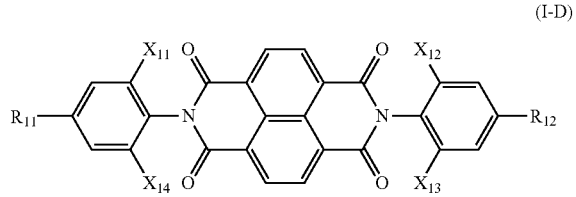

(I-D)

wherein $X_{11}$, $X_{12}$, $X_{13}$, and $X_{14}$ are each independently halo, and $R_{11}$ and $R_{12}$ are each independently alkyl, alkyl ether, or nitro;

a compound of formula (I-E):

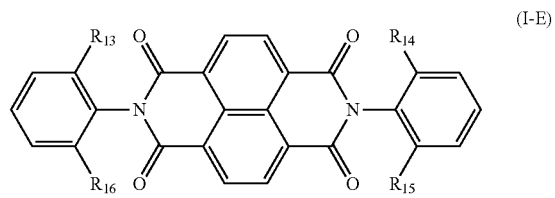

(I-E)

wherein $R_{13}$, $R_{14}$, $R_{15}$, and $R_{16}$ are each independently alkyl or alkyl ether;

and a compound of the formula (N1):

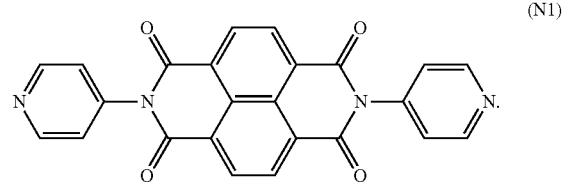 [SMILES: O=C1c2ccc3c4c(ccc(c24)C(=O)N1c1ccncc1)C(=O)N(c1ccncc1)C3=O]

(N1)

10. The method of claim 1 wherein the material is dissolved in a solvent prior to contacting the fluoride receptor reagent.

11. The method of claim 10 wherein the solvent is a polar aprotic solvents selected from the group consisting of dimethyl sulfoxide, dimethylformamide, dimethylacetamide, acetonitrile, acetone, and tetrahydrofuran.

12. The method of claim 11 wherein the polar aprotic solvent is dry.

13. The method of claim 1 wherein the fluoride receptor reagent is selected from the group consisting of:

a compound of formula (III-A):

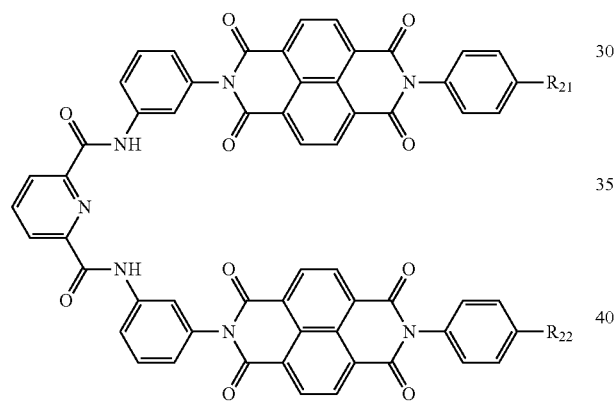

a compound of formula (III-B):

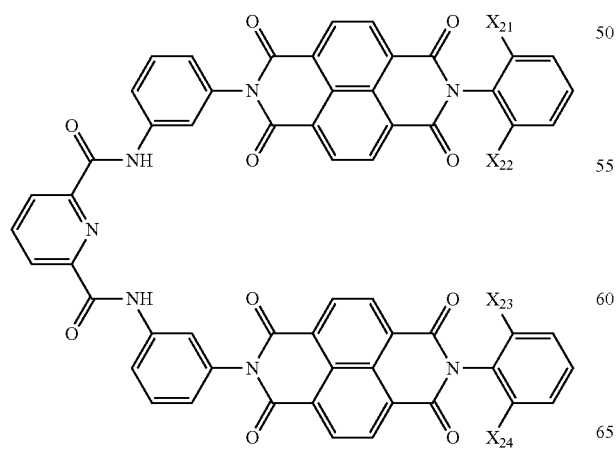

wherein $R_{21}$ and $R_{22}$ are each independently alkyl, alkyl ether, or nitro;

a compound of formula (III-C):

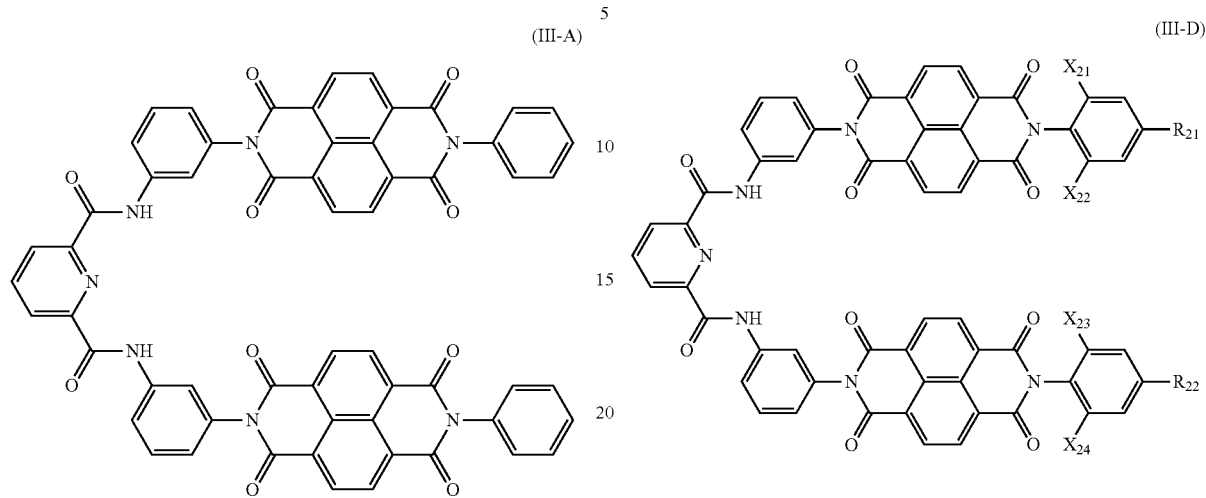

wherein $X_{21}$, $X_{22}$, $X_{23}$, and $X_{24}$ are each independently halo;

a compound of formula (III-D):

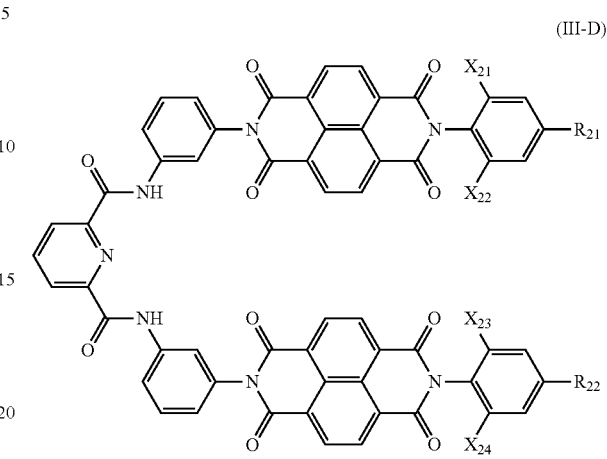

wherein $X_{21}$, $X_{22}$, $X_{23}$, and $X_{24}$ are each independently halo, and $R_{21}$ and $R_{22}$ are each independently alkyl, alkyl ether, or nitro;

a compound of formula (III-E):

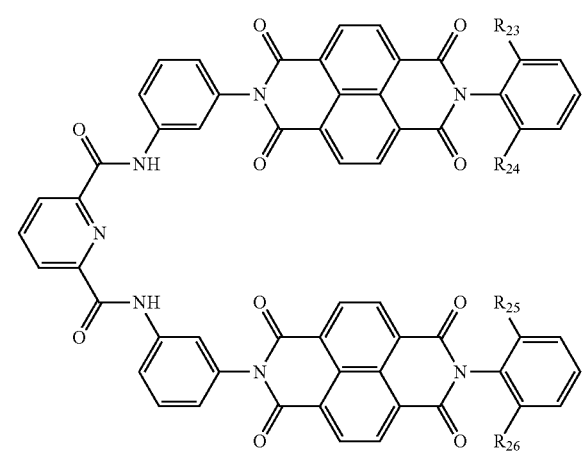

wherein $R_{23}$, $R_{24}$, $R_{25}$, and $R_{26}$ are each independently alkyl or alkyl ether;

a compound of formula (III-F):
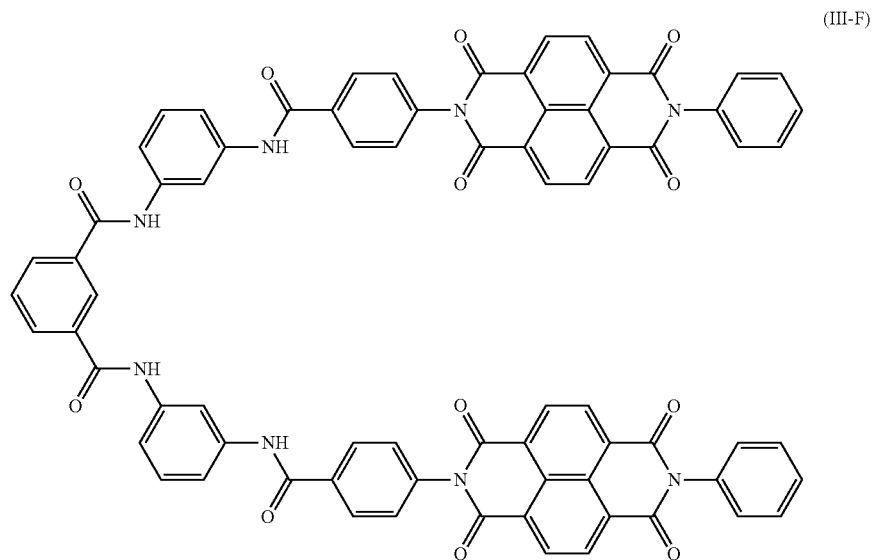 [SMILES: O=C(Nc1cccc(NC(=O)c2cccc(C(=O)Nc3cccc(NC(=O)c4ccc(N5C(=O)c6ccc7c8c(ccc(c68)C5=O)C(=O)N(c5ccccc5)C7=O)cc4)c3)c2)c1)c1ccc(N2C(=O)c3ccc4c5c(ccc(c35)C2=O)C(=O)N(c2ccccc2)C4=O)cc1]
a compound of formula (III-G):
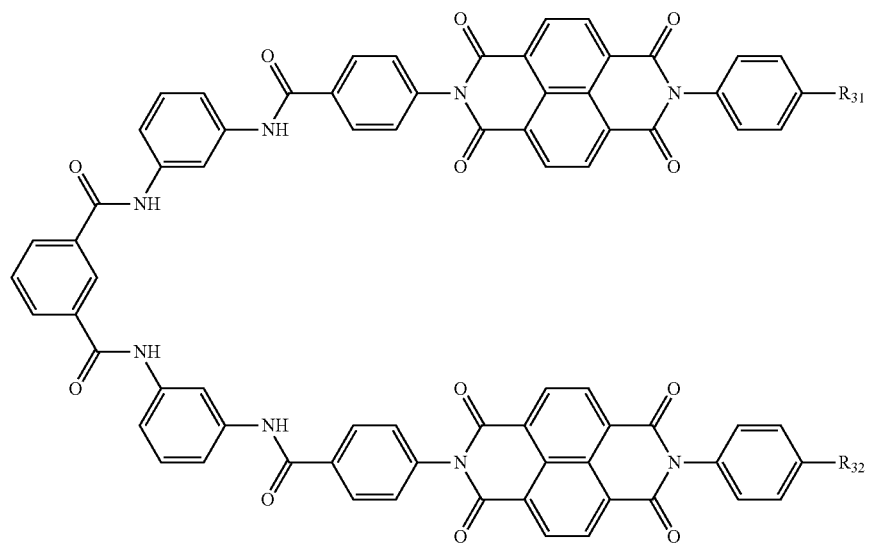
wherein $R_{31}$ and $R_{32}$ are each independently alkyl, alkyl ether, or nitro;

a compound of formula (III-H):
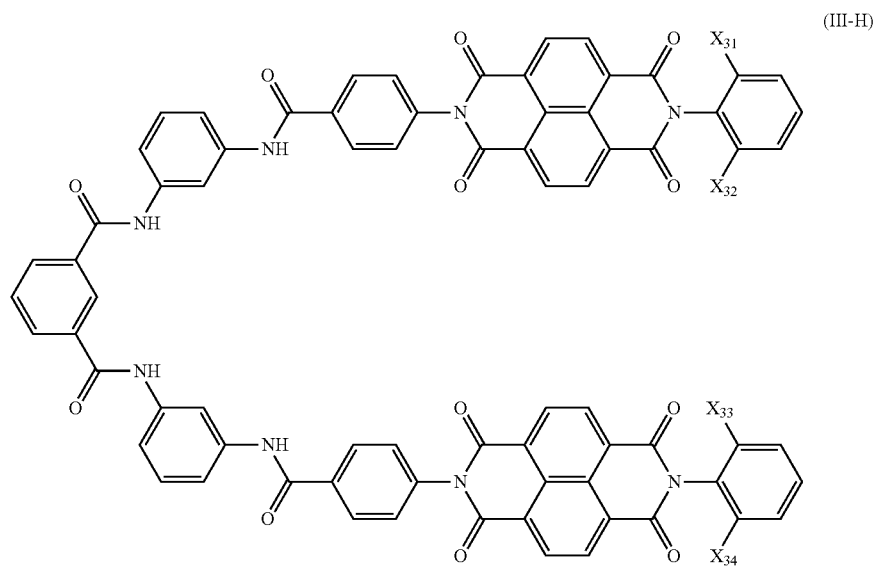
wherein $X_{31}$, $X_{32}$, $X_{33}$, and $X_{34}$ are each independently halo;
a compound of formula (III-J):
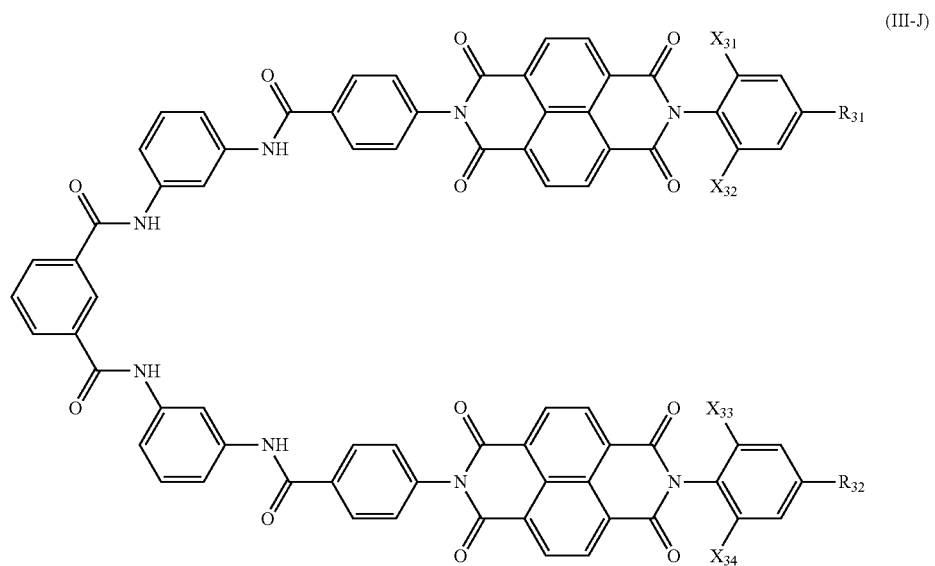
wherein $X_{31}$, $X_{32}$, $X_{33}$, and $X_{34}$ are each independently halo, and $R_{31}$ and $R_{32}$ are each independently alkyl, alkyl ether, or nitro;